United States Patent
Zeikus et al.

(10) Patent No.: US 7,198,933 B2
(45) Date of Patent: Apr. 3, 2007

(54) THERMOTOGA NEAPOLITANA XYLOSE ISOMERASE POLYPEPTIDES AND NUCLEIC ACIDS ENCODING SAME

(75) Inventors: J. Gregory Zeikus, Okemos, MI (US); Dinlaka Sriprapundh, Sausalito, CA (US); Claire Vieille, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 362 days.

(21) Appl. No.: 10/348,552

(22) Filed: Jan. 21, 2003

(65) Prior Publication Data

US 2003/0166172 A1    Sep. 4, 2003

Related U.S. Application Data

(60) Provisional application No. 60/350,930, filed on Jan. 23, 2002, provisional application No. 60/428,064, filed on Nov. 21, 2002.

(51) Int. Cl.
| | |
|---|---|
| *C12N 9/90* | (2006.01) |
| *C12N 1/12* | (2006.01) |
| *C12N 15/00* | (2006.01) |
| *C12P 21/06* | (2006.01) |
| *C07H 21/04* | (2006.01) |

(52) U.S. Cl. ............... 435/233; 435/4; 435/6; 435/69.1; 435/183; 536/23.2; 536/23.4; 536/23.5; 530/350

(58) Field of Classification Search ............ 435/4, 435/6, 69.1, 183, 200, 233, 252.3, 320.1; 530/350; 536/23.2, 23.4, 23.7
See application file for complete search history.

(56) References Cited

U.S. PATENT DOCUMENTS 5,656,497 A * 8/1997 Zeikus et al. ............ 435/320.1
5,935,837 A * 8/1999 Rasmussen ................ 435/233

* cited by examiner

*Primary Examiner*—Manjunath Rao
(74) *Attorney, Agent, or Firm*—Ian C. McLeod; Steven E. Merritt

(57) ABSTRACT

The present invention provides novel isolated polynucleotides encoding a novel xylose isomerases capable of catalyzing the conversion of glucose to fructose and nucleic acids encoding for such isomerase. The present invention also provides a method of producing the xylose isomerase enzymes employing DNA encoding for the enzymes, plasmids containing the DNA, and bacteria into which the plasmids have been inserted and which produce the enzymes.

16 Claims, 26 Drawing Sheets

FIG. 1.

FIG. 1(a). TNXI nucleotide sequence (ORF starting at 616 bp).

```
1                                                                              80
GTCGACGCAAAGGTCGTGACGGGTGGAAACATAAACGTTCAGCTGGGAACTGTGTCCTCGGCTGCTGTTGAAGGAACATA
81                                                                             160
CGTTATCGAAGTTGGACAATTCTCTGGAACGGTCACATCCGAGCTTGATGTCAAGATCCGCCGTTGTCCTCAGCACCCCT
161                                                                            240
TCCGTACACCCTGTCATCCTTCACAACGGGGATGAAGGGATCCGTTTCCCACAGCGAAAGATCCCCTGGTGGAACGGTGT
241                                                                            320
CTATGTGTGTCACTATCCACAATGTTTTGCTTCTGTCCCTGCCGGGAATGATTGCAAGCAGATTCGACCTCCAAATTCCG
321                                                                            400
TTCTGGTCTTTTGTGTCATGACGCTCAACAGTGTATCCCATCTTTTTGAGAAGTTCCTCCAGCCAGTCGGCCTTCTCTTT
401                                                                            480
CTCTCCAGGTCCACCGAAGACTGGATTCACCGAATTGATCGATATGAACCTTTTCAGCGAATCTACCATTTCGTCTTTCA
481                                                                            560
ATTCTTCTATCTTTCTTGTTATCTCCATCTGAAACACCTCCCAAGTACAAGTATATCTCTCCAAAAAAATATTTGAAATG
561                                                  ***                       640
ACCCCAGGGAATTTTATATAATTGATTGATAGAAAAAATTTAGGGAGGTGTTCACATGGCTGAATTCTTTCCAGAAATCC
641                                                                            720
CGAAAGTGCAGTTCGAAGGCAAAGAAAGCACAAATCCACTTGCGTTCAAGTTCTACGATCCAGAAGAGATCATCGACGGC
721                                                                            800
AAACCCCTCAAGGACCATCTGAAGTTCTCCGTTGCCTTCTGGCACACCTTCGTGAACGAGGGAAGGGATCCCTTCGGAGA
801                                                                            880
CCCAACGGCCGATCGTCCCTGGAACAGGTACACCGATCCCATGGACAAGGCTTTTGCAAGGGTGGACGCCCTTTTTGAAT
881                                                                            960
TCTGCGAAAAACTCAACATCGAGTACTTCTGCTTCCACGACAGAGACATCGCTCCCGAGGGAAAAACGCTGAGGGAGACA
961                                                                            1040
AACAAAATTTTGGACAAAGTAGTGGAGAGAATCAAAGAGAGAATGAAAGACAGCAACGTGAAGCTCCTCTGGGGTACTGC
1041                                                                           1120
AAACCTCTTTTCCCACCCAAGGTACATGCATGGTGCAGCGACAACCTGCAGTGCTGATGTTTTTGCGTACGCGGCCGCCC
1121                                                                           1200
AGGTGAAAAAAGCCCTTGAGATCACCAAAGAACTTGGAGGAGAAGGGTACGTCTTCTGGGGTGGAAGAGAAGGATACGAA
1201                                                                           1280
ACACTCCTCAACACGGACCTTGGATTCGAACTTGAAAACCTCGCCCGCTTCCTCAGAATGGCTGTGGATTATGCAAAAAG
1281                                                                           1360
GATCGGTTTCACCGGACAGTTCCTCATCGAACCAAAACCGAAAGAACCCACCAAACACCAGTACGACTTCGACGTTGCAA
1361                                                                           1440
CCGCCTATGCCTTCCTGAAGAGCCACGGTCTCGATGAATACTTCAAATTCAACATCGAGGCAAACCACGCCACACTCGCC
1441                                                                           1520
GGTCACACCTTCCAGCACGAACTGAGAATGGCAAGGATCCTTGGAAAACTCGGAAGCATCGATGCAAACCAGGGAGACCT
1521                                                                           1600
TCTTCTTGGATGGGACACCGATCAGTTCCCAACAAACGTCTACGATACAACCCTTGCAATGTACGAAGTGATAAAAGCGG
1601                                                                           1680
GAGGCTTCACAAAAGGTGGGCTCAACTTCGATGCGAAGGTGAGGAGGGCTTCTTACAAAGTGGAGGACCTCTTCATAGGG
1681                                                                           1760
CACATAGCGGGAATGGACACCTTTGCACTCGGTTTCAAGGTGGCATACAAACTCGTGAAGGATGGTGTTCTGGACAAATT
1761                                                                           1840
CATCGAAGAAAAGTACAGAAGTTTCAGGGAGGGCATTGGAAGGGACATCGTCGAAGGTAAAGTGGATTTTGAAAAACTTG
1841                                                                           1920
AAGAGTATATAATAGACAAAGAAACGATAGAACTTCCATCTGGAAAGCAAGAATACCTGGAAAGCCTCATCAACAGTTAC
1921                    ***                                                    2000
ATAGTGAAGACCATTCTGGAACTGAGGTGAAACAGAGTGTGAAGTTCTTGAATCTTCGAAGATTACTTCTTCTGGCACTG

ATTGCGGCTGGAATCTCAGTGATCATAGTCGTATCCAACCGGGAAAACAGGGTGAAATTTCCAGAAGGAGAGATTGTGAT
AACTGACGGAGAAAGATCTCTGAAACTTCGTGTCGAGATAGCGAACACTCCTTTTTTCGTTCGATCGGTCTGATGTACA
GAAAGAGCATCCCGGATGACTTCGGGATGCTCTTTGTTTTGAAGAAGATACAAGAAGCGGCTTCTGGATGAAGAACACC
TACGTTCCCCTCGAAATCGCCTTCATAGACAGAAACGGCATCGTATTTTCCATTCAGGAGATGGAGCCATGCGAAAAGA
ACCCTGCAAGGTTTACTACGCACCAAAGCCGTTCAGATACGCTCTTGAAGTGAAAAGAGGTTTTTTCGAAAGGCATGGAT
TTGGAGTGGGAAGCCGTGTCCTGATAGAAAAGTAGCGGTACTTTCAAACAAAAACGTATGGAATCTTCATCTTCTTTGCC
```

TCGTACATTCTCGAGTCAGCCATCTTCAGAAGTTCTTCTAGA

FIG.1(b). TNXI deduced amino acid sequence.

```
1                                                                              80
AEFFPEIPKVQFEGKESTNPLAFKFYDPEEIIDGKPLKDHLKFSVAFWHTFVNEGRDPFGDPTADRPWNRYTDPMDKAFA 81                                                                             160
RVDALFEFCEKLNIEYFCFHDRDIAPEGKTLRETNKILDKVVERIKERMKDSNVKLLWGTANLFSHPRYMHGAATTCSAD 161                                                                            240
VFAYAAAQVKKALEITKELGGEGYVFWGGREGYETLLNTDLGFELENLARFLRMAVDYAKRIGFTGQFLIEPKPKEPTKH 241                                                                            320
QYDFDVATAYAFLKSHGLDEYFKFNIEANHATLAGHTFQHELRMARILGKLGSIDANQGDLLLGWDTDQFPTNVYDTTLA 321                                                                            400
MYEVIKAGGFTKGGLNFDAKVRRASYKVEDLFIGHIAGMDTFALGFKVAYKLVKDGVLDKFIEEKYRSFREGIGRDIVEG 401                                                                            480
KVDFEKLEEYIIDKETIELPSGKQEYLESLINSYIVKTILELR******
```

FIG 1(c). Mutations to the native glucose isomerase gene.

| | | |
|---|---|---|
| TNXI V185T | | 185:GTC(Val)->ACC(Thr) |
| TNXI 3A2 | [V185T and L282P] | 185:GTC(Val)->ACC(Thr) |
| | | 282:CTG(Leu)->CCG(Pro) |
| TNXI 6H12 | [V185T and Y164D] | 185:GTC(Val)->ACC(Thr) |
| | | 164:TAC(Tyr)->GAC(Asp) |
| TNXI S1E10 | [V185T,Y164D,Y250C,L282P,R286M] | 185:GTC(Val)->ACC(Thr) |
| | | 164:TAC(Tyr)->GAC(Asp) |
| | | 250:TAT(Tyr)->TGT(Cys) |
| | | 282:CTG(Leu)->CCG(Pro) |
| | | 286:AGG(Arg)->ATG(Met) |
| TNXI S1H12 | [V185T,Y164D,L282P] | 185:GTC(Val)->ACC(Thr) |
| | | 164:TAC(Tyr)->GAC(Asp) |
| | | 282:CTG(Leu)->CCG(Pro) |

SEQ ID NO: 11

TNXI\1F1 (V185T/F186S/L282P) deduced amino acid sequence

```
1                                                                              80
AEFFPEIPKVQFEGKESTNPLAFKFYDPEEIIDGKPLKDHLKFSVAFWHTFVNEGRDPFGDPTADRPWNRYTDPMDKAFA 81                                                                             160
RVDALFEFCEKLNIEYFCFHDRDIAPEGKTLRETNKILDKVVERIKERMKDSNVKLLWGTANLFSHPRYMHGAATTCSAD 161                                                                            240
VFAYAAAQVKKALEITKELGGEGYTSWGGREGYETLLNTDLGFELENLARFLRMAVDYAKRIGFTGQFLIEPKPKEPTKH 241                                                                            320
QYDFDVATAYAFLKSHGLDEYFKFNIEANHATLAGHTFQHEPRMARILGKLGSIDANQGDLLLGWDTDQFPTNVYDTTLA 321                                                                            400
MYEVIKAGGFTKGGLNFDAKVRRASYKVEDLFIGHIAGMDTFALGFKVAYKLVKDGVLDKFIEEKYRSFREGIGRDIVEG 401                                                                            480
KVDFEKLEEYIIDKETIELPSGKQEYLESLINSYIVKTILELR******
```

FIGURE 19

SEQ ID NO:12

TNXI 1F1 nucleotide sequence (ORF starting at 616 bp)

```
1                                                                             80
GTCGACGCAAAGGTCGTGACGGGTGGAAACATAAACGTTCAGCTGGGAACTGTGTCCTCGGCTGCTGTTGAAGGAACATA
81                                                                            160
CGTTATCGAAGTTGGACAATTCTCTGGAACGGTCACATCCGAGCTTGATGTCAAGATCCGCCGTTGTCCTCAGCACCCCT
161                                                                           240
TCCGTACACCCTGTCATCCTTCACAACGGGGATGAAGGGATCCGTTTCCCACAGCGAAAGATCCCCTGGTGGAACGGTGT
241                                                                           320
CTATGTGTGTCACTATCCACAATGTTTTGCTTCTGTCCCTGCCGGGAATGATTGCAAGCAGATTCGACCTCCAAATTCCG
321                                                                           400
TTCTGGTCTTTTGTGTCATGACGCTCAACAGTGTATCCCATCTTTTTGAGAAGTTCCTCCAGCCAGTCGGCCTTCTCTTT
401                                                                           480
CTCTCCAGGTCCACCGAAGACTGGATTCACCGAATTGATCGATATGAACCTTTTCAGCGAATCTACCATTTCGTCTTTCA
481                                                                           560
ATTCTTCTATCTTTCTTGTTATCTCCATCTGAAACACCTCCCAAGTACAAGTATATCTCTCCAAAAAAATATTTGAAATG
561                                             ***                           640
ACCCCAGGGAATTTTATATAATTGATTGATAGAAAAAATTTAGGGAGGTGTTCACATGGCTGAATTCTTTCCAGAAATCC
                                                  A   E  F  F  P  E  I
641                                                                           720
CGAAAGTGCAGTTCGAAGGCAAAGAAAGCACAAATCCACTTGCGTTCAAGTTCTACGATCCAGAAGAGATCATCGACGGC
 P  K  V  Q  F  E  G  K  E  S  T  N  P  L  A  F  K  F  Y  D  P  E  E  I  I  D  G
721                                                                           800
AAACCCCTCAAGGACCATCTGAAGTTCTCCGTTGCCTTCTGGCACACCTTCGTGAACGAGGGAAGGGATCCCTTCGGAGA
  K  P  L  K  D  H  L  K  F  S  V  A  F  W  H  T  F  V  N  E  G  R  D  P  F  G  D
801                                                                           880
CCCCAACGGCCGATCGTCCCTGGAACAGGTACACCGATCCCATGGACAAGGCTTTTGCAAGGGTGGACGCCCTTTTTGAAT
   P  T  A  D  R  P  W  N  R  Y  T  D  P  M  D  K  A  F  A  R  V  D  A  L  F  E
881                                                                           960
TCTGCGAAAAACTCAACATCGAGTACTTCTGCTTCCACGACAGAGACATCGCTCCCGAGGGAAAAACGCTGAGGGAGACA
 F  C  E  K  L  N  I  E  Y  F  C  F  H  D  R  D  I  A  P  E  G  K  T  L  R  E  T
961                                                                           1040
AACAAAATTTTGGACAAAGTAGTGGAGAGAATCAAAGAGAGAATGAAAGACAGCAACGTGAAGCTCCTCTGGGGTACTGC
 N  K  I  L  D  K  V  V  E  R  I  K  E  R  M  K  D  S  N  V  K  L  L  W  G  T  A
1041                                                                          1120
AAACCTCTTTTCCCACCCAAGGTACATGCATGGTGCAGCGACAACCTGCAGTGCTGATGTTTTGCGTACGCGGCCGCCC
  N  L  F  S  H  P  R  Y  M  H  G  A  A  T  T  C  S  A  D  V  F  A  Y  A  A  A
1121                                                                          1200
AGGTGAAAAAAGCCCTTGAGATCACCAAAGAACTTGGAGGAGAAGGGTACACCTCCTGGGGTGGAAGAGAAGGATACGAA
 Q  V  K  K  A  L  E  I  T  K  E  L  G  G  E  G  Y  T  S  W  G  G  R  E  G  Y  E
1201                                                                          1280
ACACTCCTCAACACGGACCTTGGATTCGAACTTGAAAACCTCGCCCGCTTCCTCAGAATGGCTGTGGATTATGCAAAAAG
  T  L  L  N  T  D  L  G  F  E  L  E  N  L  A  R  F  L  R  M  A  V  D  Y  A  K  R
1281                                                                          1360
GATCGGTTTCACCGGACAGTTCCTCATCGAACCAAAACCGAAAGAACCCACCAAACACCAGTACGACTTCGACGTTGCAA
   I  G  F  T  G  Q  F  L  I  E  P  K  P  K  E  P  T  K  H  Q  Y  D  F  D  V  A
1361                                                                          1440
CCGCCTATGCCTTCCTGAAGAGCCACGGTCTCGATGAATACTTCAAATTCAACATCGAGGCAAACCACGCCACACTCGCC
```

FIGURE 20

```
1441                .             .              .              .          1520
GGTCACACCTTCCAGCACGAACCGAGAATGGCAAGGATCCTTGGAAAACTCGGAAGCATCGATGCAAACCAGGGAGACCT
   G  H  T  F  Q  H  E  P  R  M  A  R  I  L  G  K  L  G  S  I  D  A  N  Q  G  D  L

1521                .             .              .              .          1600
TCTTCTTGGATGGGACACCGATCAGTTCCCAACAAACGTCTACGATACAACCCTTGCAATGTACGAAGTGATAAAAGCGG
    L  L  G  W  D  T  D  Q  F  P  T  N  V  Y  D  T  T  L  A  M  Y  E  V  I  K  A

1601                .             .              .              .          1680
GAGGCTTCACAAAAGGTGGGCTCAACTTCGATGCGAAGGTGAGGAGGGCTTCTTACAAAGTGGAGGACCTCTTCATAGGG
   G  G  F  T  K  G  G  L  N  F  D  A  K  V  R  R  A  S  Y  K  V  E  D  L  F  I  G

1681                .             .              .              .          1760
CACATAGCGGGAATGGACACCTTTGCACTCGGTTTCAAGGTGGCATACAAACTCGTGAAGGATGGTGTTCTGGACAAATT
   H  I  A  G  M  D  T  F  A  L  G  F  K  V  A  Y  K  L  V  K  D  G  V  L  D  K  F

1761                .             .              .              .          1840
CATCGAAGAAAAGTACAGAAGTTTCAGGGAGGGCATTGGAAGGGACATCGTCGAAGGTAAAGTGGATTTTGAAAAACTTG
    I  E  E  K  Y  R  S  F  R  E  G  I  G  R  D  I  V  E  G  K  V  D  F  E  K  L .

1841                .             .              .              .          1920
AAGAGTATATAATAGACAAAGAAACGATAGAACTTCCATCTGGAAAGCAAGAATACCTGGAAAGCCTCATCAACAGTTAC
   E  E  Y  I  I  D  K  E  T  I  E  L  P  S  G  K  Q  E  Y  L  E  S  L  I  N  S  Y

1921                .          ***.             .              .          2000
ATAGTGAAGACCATTCTGGAACTGAGGTGAAACAGAGTGTGAAGTTCTTGAATCTTCGAAGATTACTTCTTCTGGCACTG
    I  V  K  T  I  L  E  L  R

ATTGCGGCTGGAATCTCAGTGATCATAGTCGTATCCAACCGGGAAAACAGGGTGAAATTTCCAGAAGGAGAGATTGTGAT
AACTGACGGAGAAAGATCTCTGAAACTTCGTGTCGAGATAGCGAACACTCCTTTTTTTCGTTCGATCGGTCTGATGTACA
GAAAGAGCATCCCGGATGACTTCGGGATGCTCTTTGTTTTGAAGAAGATACAAGAAGCGGCTTCTGGATGAAGAACACC
TACGTTCCCCTCGAAATCGCCTTCATAGACAGAAACGGCATCGTATTTTCCATTCAGGAGATGGAGCCATGCGAAAAGA
ACCCTGCAAGGTTTACTACGCACCAAAGCCGTTCAGATACGCTCTTGAAGTGAAAAGAGGTTTTTTCGAAAGGCATGGAT
TTGGAGTGGGAAGCCGTGTCCTGATAGAAAAGTAGCGGTACTTTCAAACAAAAACGTATGGAATCTTCATCTTCTTTGCC
TCGTACATTCTCGAGTCAGCCATCTTCAGAAGTTCTTCTAGA
```

TNXI 1F1   [V185T, F186S, and L282P]      185:GTC(Val)->ACC(Thr)
                                          186:TTC(Phe)->TCC(Ser)
                                          282:CTG(Leu)->CCG(Pro)

FIGURE 20 (Continued)

SEQUENCE LISTING

<160> NUMBER OF SEQ ID NOS: 12

<210> SEQ ID NO 1
<211> LENGTH: 2522
<212> TYPE: DNA
<213> ORGANISM: Thermotoga neapolitana

<400> SEQUENCE: 1

| | | | | | | |
|---|---|---|---|---|---|---|
| gtcgacgcaa | aggtcgtgac | gggtggaaac | ataaacgttc | agctgggaac | tgtgtcctcg | 60 |
| gctgctgttg | aaggaacata | cgttatcgaa | gttggacaat | tctctggaac | ggtcacatcc | 120 |
| gagcttgatg | tcaagatccg | ccgttgtcct | cagcacccct | tccgtacacc | ctgtcatcct | 180 |
| tcacaacggg | gatgaaggga | tccgtttccc | acagcgaaag | atcccctggt | ggaacggtgt | 240 |
| ctatgtgtgt | cactatccac | aatgttttgc | ttctgtccct | gccgggaatg | attgcaagca | 300 |
| gattcgacct | ccaaattccg | ttctggtctt | ttgtgtcatg | acgctcaaca | gtgtatccca | 360 |
| tcttttttgag | aagttcctcc | agccagtcgg | ccttctcttt | ctctccaggt | ccaccgaaga | 420 |
| ctggattcac | cgaattgatc | gatatgaacc | ttttcagcga | atctaccatt | tcgtctttca | 480 |
| attcttctat | ctttcttgtt | atctccatct | gaaacacctc | ccaagtacaa | gtatatctct | 540 |
| ccaaaaaaat | atttgaaatg | accccaggga | attttatata | attgattgat | agaaaaaatt | 600 |
| tagggaggtg | ttcacatggc | tgaattcttt | ccagaaatcc | cgaaagtgca | gttcgaaggc | 660 |
| aaagaaagca | caaatccact | tgcgttcaag | ttctacgatc | cagaagagat | catcgacggc | 720 |
| aaaccctca | aggaccatct | gaagttctcc | gttgccttct | ggcacacctt | cgtgaacgag | 780 |
| ggaagggatc | ccttcggaga | cccaacggcc | gatcgtccct | ggaacaggta | caccgatccc | 840 |
| atggacaagg | cttttgcaag | ggtggacgcc | cttttttgaat | tctgcgaaaa | actcaacatc | 900 |
| gagtacttct | gcttccacga | cagagacatc | gctcccgagg | gaaaaacgct | gagggagaca | 960 |
| aacaaaattt | tggacaaagt | agtggagaga | atcaaagaga | gaatgaaaga | cagcaacgtg | 1020 |
| aagctcctct | ggggtactgc | aaacctcttt | tcccacccaa | ggtacatgca | tggtgcagcg | 1080 |
| acaacctgca | gtgctgatgt | ttttgcgtac | gcggccgccc | agtgaaaaa | agcccttgag | 1140 |
| atcaccaaag | aacttggagg | agaagggtac | gtcttctggg | gtggaagaga | aggatacgaa | 1200 |
| acactcctca | acacggacct | tggattcgaa | cttgaaaacc | tcgcccgctt | cctcagaatg | 1260 |
| gctgtggatt | atgcaaaaag | gatcggtttc | accggacagt | tcctcatcga | accaaaaccg | 1320 |
| aaagaaccca | ccaaacacca | gtacgacttc | gacgttgcaa | ccgcctatgc | cttcctgaag | 1380 |
| agccacggtc | tcgatgaata | cttcaaattc | aacatcgagg | caaaccacgc | cacactcgcc | 1440 |
| ggtcacacct | tccagcacga | actgagaatg | gcaaggatcc | ttggaaaact | cggaagcatc | 1500 |
| gatgcaaacc | agggagacct | tcttcttgga | tgggacaccg | atcagttccc | aacaaacgtc | 1560 |
| tacgatacaa | cccttgcaat | gtacgaagtg | ataaagcgg | gaggcttcac | aaaaggtggg | 1620 |
| ctcaacttcg | atgcgaaggt | gaggagggct | tcttacaaag | tggaggacct | cttcataggg | 1680 |
| cacatagcgg | gaatggacac | cttttgcactc | ggtttcaagg | tggcatacaa | actcgtgaag | 1740 |
| gatggtgttc | tggacaaatt | catcgaagaa | aagtacagaa | gtttcaggga | gggcattgga | 1800 |
| agggacatcg | tcgaaggtaa | agtggatttt | gaaaaacttg | aagagtatat | aatagacaaa | 1860 |
| gaaacgatag | aacttccatc | tggaaagcaa | gaataccttgg | aaagcctcat | caacagttac | 1920 |
| atagtgaaga | ccattctgga | actgaggtga | acagagtgt | gaagttcttg | aatcttcgaa | 1980 |
| gattacttct | tctggcactg | attgcggctg | gaatctcagt | gatcatagtc | gtatccaacc | 2040 |

-continued

```
gggaaaacag ggtgaaattt ccagaaggag agattgtgat aactgacgga gaaagatctc   2100
tgaaacttcg tgtcgagata gcgaacactc cttttttttcg ttcgatcggt ctgatgtaca   2160
gaaagagcat cccggatgac ttcgggatgc tctttgtttt tgaagaagat acaagaagcg   2220
gcttctggat gaagaacacc tacgttcccc tcgaaatcgc cttcatagac agaaacggca   2280
tcgtattttc cattcaggag atggagccat gcgaaaaaga accctgcaag gtttactacg   2340
caccaaagcc gttcagatac gctcttgaag tgaaagaggg ttttttcgaa aggcatggat   2400
ttggagtggg aagccgtgtc ctgatagaaa agtagcggta ctttcaaaca aaaacgtatg   2460
gaatcttcat cttctttgcc tcgtacattc tcgagtcagc catcttcaga agttcttcta   2520
ga                                                                 2522
```

<210> SEQ ID NO 2
<211> LENGTH: 444
<212> TYPE: PRT
<213> ORGANISM: Thermotoga neapolitana

<400> SEQUENCE: 2

```
Met Ala Glu Phe Phe Pro Glu Ile Pro Lys Val Gln Phe Glu Gly Lys
 1               5                  10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
```

```
                 275                 280                 285
Leu Gly Lys Leu Gly Ser Ile Asp Ala Asn Gln Gly Asp Leu Leu Leu
    290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
                340                 345                 350

Phe Ile Gly His Ile Ala Gly Met Asp Thr Phe Ala Leu Gly Phe Lys
            355                 360                 365

Val Ala Tyr Lys Leu Val Lys Asp Gly Val Leu Asp Lys Phe Ile Glu
    370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
        435                 440

<210> SEQ ID NO 3
<211> LENGTH: 2522
<212> TYPE: DNA
<213> ORGANISM: Thermotoga neapolitana

<400> SEQUENCE: 3
gtcgacgcaa aggtcgtgac gggtggaaac ataaacgttc agctgggaac tgtgtcctcg    60
gctgctgttg aaggaacata cgttatcgaa gttggacaat tctctggaac ggtcacatcc   120
gagcttgatg tcaagatccg ccgttgtcct cagcacccct tccgtacacc ctgtcatcct   180
tcacaacggg gatgaaggga tccgtttccc acagcgaaag atcccctggt ggaacggtgt   240
ctatgtgtgt cactatccac aatgttttgc ttctgtccct gccgggaatg attgcaagca   300
gattcgacct ccaaattccg ttctggtctt tgtgtcatg acgctcaaca gtgtatccca   360 tcttttgag aagttcctcc agccagtcgg ccttctcttt ctctccaggt ccaccgaaga   420
ctggattcac cgaattgatc gatatgaacc ttttcagcga atctaccatt tcgtctttca   480
attcttctat ctttcttgtt atctccatct gaaacacctc ccaagtacaa gtatatctct   540
ccaaaaaaat atttgaaatg accccaggga attttatata attgattgat agaaaaaatt   600
tagggaggtg ttcacatggc tgaattcttt ccagaaatcc cgaaagtgca gttcgaaggc   660
aaagaaagca caaatccact tgcgttcaag ttctacgatc cagaagagat catcgacggc   720 aaaccctca aggaccatct gaagttctcc gttgccttct ggcacacctt cgtgaacgag   780
ggaagggatc ccttcggaga cccaacggcc gatcgtccct ggaacaggta caccgatccc   840
atggacaagg cttttgcaag ggtggacgcc ctttttgaat ctgcgaaaa actcaacatc   900 gagtacttct gcttccacga cagagacatc gctcccgagg gaaaaacgct gagggagaca   960
aacaaaattt tggacaaagt agtggagaga atcaaagaga gaatgaaaga cagcaacgtg  1020
aagctcctct ggggtactgc aaacctcttt tcccacccaa ggtacatgca tggtgcagcg  1080
acaacctgca gtgctgatgt ttttgcgtac gcggccgccc aggtgaaaaa agcccttgag  1140
atcaccaaag aacttggagg agaagggtac accttctggg gtggaagaga aggatacgaa  1200
```

-continued

```
acactcctca acacggacct tggattcgaa cttgaaaacc tcgcccgctt cctcagaatg    1260
gctgtggatt atgcaaaaag gatcggtttc accggacagt tcctcatcga accaaaaccg    1320
aaagaaccca ccaaacacca gtacgacttc gacgttgcaa ccgcctatgc cttcctgaag    1380
agccacggtc tcgatgaata cttcaaattc aacatcgagg caaccacgc cacactcgcc     1440
ggtcacacct tccagcacga accgagaatg caaggatcc ttggaaaact cggaagcatc     1500
gatgcaaacc agggagacct tcttcttgga tgggacaccg atcagttccc aacaaacgtc    1560
tacgatacaa cccttgcaat gtacgaagtg ataaaagcgg gaggcttcac aaaaggtggg    1620
ctcaacttcg atgcgaaggt gaggagggct tcttacaaag tggaggacct cttcataggg    1680
cacatagcgg gaatggacac ctttgcactc ggtttcaagg tggcatacaa actcgtgaag    1740
gatggtgttc tggacaaatt catcgaagaa aagtacagaa gtttcaggga gggcattgga    1800
agggacatcg tcgaaggtaa agtggatttt gaaaaacttg aagagtatat aatagacaaa    1860
gaaacgatag aacttccatc tggaaagcaa gaatacctgg aaagcctcat caacagttac    1920
atagtgaaga ccattctgga actgaggtga acagagtgt gaagttcttg aatcttcgaa     1980
gattacttct tctggcactg attgcggctg aatctcagt gatcatagtc gtatccaacc     2040
gggaaaacag ggtgaaattt ccagaaggag agattgtgat aactgacgga gaaagatctc    2100
tgaaacttcg tgtcgagata gcgaacactc cttttttcg ttcgatcggt ctgatgtaca     2160
gaaagagcat cccggatgac ttcgggatgc tctttgtttt tgaagaagat acaagaagcg    2220
gcttctggat gaagaacacc tacgttcccc tcgaaatcgc cttcatagac agaaacggca    2280
tcgtatttc cattcaggag atggagccat gcgaaaaaga accctgcaag gtttactacg    2340
caccaaagcc gttcagatac gctcttgaag tgaaaagagg tttttttcgaa aggcatggat   2400
ttggagtggg aagccgtgtc ctgatagaaa agtagcggta ctttcaaaca aaaacgtatg   2460
gaatcttcat cttctttgcc tcgtacattc tcgagtcagc catcttcaga agttcttcta   2520
ga                                                                    2522
```

<210> SEQ ID NO 4
<211> LENGTH: 444
<212> TYPE: PRT
<213> ORGANISM: Thermotoga neapolitana

<400> SEQUENCE: 4

```
Met Ala Glu Phe Phe Pro Glu Ile Pro Lys Val Gln Phe Glu Gly Lys
1               5                   10                  15
Glu Ser Thr Asn Pro Leu Ala Phe Lys Phe Tyr Asp Pro Glu Glu Ile
                20                  25                  30
Ile Asp Gly Lys Pro Leu Lys Asp His Leu Lys Phe Ser Val Ala Phe
            35                  40                  45
Trp His Thr Phe Val Asn Glu Gly Arg Asp Pro Phe Gly Asp Pro Thr
        50                  55                  60
Ala Asp Arg Pro Trp Asn Arg Tyr Thr Asp Pro Met Asp Lys Ala Phe
65                  70                  75                  80
Ala Arg Val Asp Ala Leu Phe Glu Phe Cys Glu Lys Leu Asn Ile Glu
                85                  90                  95
Tyr Phe Cys Phe His Asp Arg Asp Ile Ala Pro Glu Gly Lys Thr Leu
            100                 105                 110
Arg Glu Thr Asn Lys Ile Leu Asp Lys Val Val Glu Arg Ile Lys Glu
        115                 120                 125
```

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Gln Val Lys Lys Ala Leu Glu Ile
                165                 170                 175

Thr Lys Glu Leu Gly Gly Glu Gly Tyr Thr Phe Trp Gly Gly Arg Glu
            180                 185                 190

Gly Tyr Glu Thr Leu Leu Asn Thr Asp Leu Gly Phe Glu Leu Glu Asn
            195                 200                 205

Leu Ala Arg Phe Leu Arg Met Ala Val Asp Tyr Ala Lys Arg Ile Gly
210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Pro Arg Met Ala Arg Ile
            275                 280                 285

Leu Gly Lys Leu Gly Ser Ile Asp Ala Asn Gln Gly Asp Leu Leu Leu
290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
            355                 360                 365

Val Ala Tyr Lys Leu Val Lys Asp Gly Val Leu Asp Lys Phe Ile Glu
370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
435                 440

<210> SEQ ID NO 5
<211> LENGTH: 2522
<212> TYPE: DNA
<213> ORGANISM: Thermotoga neapolitana

<400> SEQUENCE: 5
gtcgacgcaa aggtcgtgac gggtggaaac ataaacgttc agctgggaac tgtgtcctcg      60
gctgctgttg aaggaacata cgttatcgaa gttggacaat tctctggaac ggtcacatcc     120
gagcttgatg tcaagatccg ccgttgtcct cagcacccct tccgtacacc ctgtcatcct     180
tcacaacggg gatgaaggga tccgtttccc acagcgaaag atcccctggt ggaacggtgt     240
ctatgtgtgt cactatccac aatgttttgc ttctgtccct gccgggaatg attgcaagca     300
gattcgacct ccaaattccg ttctggtctt ttgtgtcatg acgctcaaca gtgtatccca     360

-continued

```
tcttttttgag aagttcctcc agccagtcgg ccttctcttt ctctccaggt ccaccgaaga    420
ctggattcac cgaattgatc gatatgaacc ttttcagcga atctaccatt tcgtctttca    480
attcttctat ctttcttgtt atctccatct gaaacacctc ccaagtacaa gtatatctct    540
ccaaaaaaat atttgaaatg accccaggga attttatata attgattgat agaaaaaatt    600
tagggaggtg ttcacatggc tgaattcttt ccagaaatcc cgaaagtgca gttcgaaggc    660
aaagaaagca caaatccact tgcgttcaag ttctacgatc cagaagagat catcgacggc    720
aaacccctca aggaccatct gaagttctcc gttgccttct ggcacaccttt cgtgaacgag    780
ggaagggatc ccttcggaga cccaacggcc gatcgtccct ggaacaggta caccgatccc    840
atggacaagg cttttgcaag ggtggacgcc ctttttgaat tctgcgaaaa actcaacatc    900
gagtacttct gcttccacga cagagacatc gctcccgagg aaaaacgct gagggagaca    960
aacaaaattt tggacaaagt agtggagaga atcaaagaga aatgaaaga cagcaacgtg   1020
aagctcctct ggggtactgc aaacctcttt tcccacccaa ggtacatgca tggtgcagcg   1080
acaacctgca gtgctgatgt ttttgcggac gcggccgccc aggtgaaaaa agcccttgag   1140
atcaccaaag aacttggagg agaagggtac accttctggg gtggaagaga aggatacgaa   1200
acactcctca cacgaccct tggattcgaa cttgaaaacc tcgcccgctt cctcagaatg   1260
gctgtggatt atgcaaaaag gatcggtttc accggacagt tcctcatcga accaaaaccg   1320
aaagaaccca ccaaacacca gtacgacttc gacgttgcaa ccgcctatgc cttcctgaag   1380
agccacggtc tcgatgaata cttcaaattc aacatcgagg caaccacgc cacactcgcc   1440
ggtcacacct tccagcacga actgagaatg caaggatcc ttggaaaact cggaagcatc   1500
gatgcaaaacc agggagacct tcttcttgga tgggacaccg atcagttccc aacaaacgtc   1560
tacgatacaa cccttgcaat gtacgaagtg ataaaagcgg gaggcttcac aaaaggtggg   1620
ctcaacttcg atgcgaaggt gaggagggct tcttacaaag tggaggacct cttcataggg   1680
cacatagcgg gaatggacac ctttgcactc ggtttcaagg tggcatacaa actcgtgaag   1740
gatggtgttc tggacaaatt catcgaagaa agtacagaa gtttcaggga gggcattgga   1800
agggacatcg tcgaaggtaa agtggatttt gaaaaacttg aagagtatat aatagacaaa   1860
gaaacgatag aacttccatc tggaaagcaa gaataactgg aaagcctcat caacagttac   1920
atagtgaaga ccattctgga actgaggtga acagagtgt gaagttcttg aatcttcgaa   1980
gattacttct tctggcactg attgcggctg aatctcagt gatcatagtc gtatccaacc   2040
gggaaaacag ggtgaaattt ccagaaggag agattgtgat aactgacgga gaaagatctc   2100
tgaaacttcg tgtcgagata gcgaacactc ctttttttcg ttcgatcggt ctgatgtaca   2160
gaaagagcat cccggatgac ttcgggatgc tctttgtttt tgaagaagat acaagaagcg   2220
gcttctggat gaagaacacc tacgttcccc tcgaaatcgc cttcatagac agaaacggca   2280
tcgtatttc cattcaggag atggagccat gcgaaaaga accctgcaag gtttactacg   2340
caccaaagcc gttcagatac gctcttgaag tgaaaagagg tttttttcgaa aggcatggat   2400
ttggagtggg aagccgtgtc ctgatagaaa agtagcggta ctttcaaaca aaaacgtatg   2460
gaatcttcat cttcttttgcc tcgtacattc tcgagtcagc catcttcaga agttcttcta   2520
ga                                                                   2522
```

<210> SEQ ID NO 6
<211> LENGTH: 444
<212> TYPE: PRT

<213> ORGANISM: Thermotoga neapolitana

<400> SEQUENCE: 6

```
Met Ala Glu Phe Phe Pro Glu Ile Pro Lys Val Gln Phe Glu Gly Lys
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Asp Ala Ala Ala Gln Val Lys Lys Ala Leu Glu Ile
                165                 170                 175

Thr Lys Glu Leu Gly Gly Glu Gly Tyr Thr Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
    370                 375                 380

Glu Lys Tyr Arg Ser Phe Arg Glu Gly Ile Gly Arg Asp Ile Val Glu
385                 390                 395                 400
```

-continued

Gly Lys Val Asp Phe Glu Lys Leu Glu Glu Tyr Ile Ile Asp Lys Glu
            405                 410                 415

Thr Ile Glu Leu Pro Ser Gly Lys Gln Glu Tyr Leu Glu Ser Leu Ile
        420                 425                 430

Asn Ser Tyr Ile Val Lys Thr Ile Leu Glu Leu Arg
        435                 440

<210> SEQ ID NO 7
<211> LENGTH: 2522
<212> TYPE: DNA
<213> ORGANISM: Thermotoga neapolitana

<400> SEQUENCE: 7

| | | |
|---|---|---|
| gtcgacgcaa aggtcgtgac gggtggaaac ataaacgttc agctgggaac tgtgtcctcg | 60 |
| gctgctgttg aaggaacata cgttatcgaa gttggacaat tctctggaac ggtcacatcc | 120 |
| gagcttgatg tcaagatccg ccgttgtcct cagcacccct tccgtacacc ctgtcatcct | 180 |
| tcacaacggg gatgaaggga tccgtttccc acagcgaaag atccctggt ggaacggtgt | 240 |
| ctatgtgtgt cactatccac aatgttttgc ttctgtccct gccgggaatg attgcaagca | 300 |
| gattcgacct ccaaattccg ttctggtctt ttgtgtcatg acgctcaaca gtgtatccca | 360 |
| tcttttgag aagttcctcc agccagtcgg ccttctcttt ctctccaggt ccaccgaaga | 420 |
| ctggattcac cgaattgatc gatatgaacc ttttcagcga atctaccatt tcgtctttca | 480 |
| attcttctat ctttcttgtt atctccatct gaaacacctc ccaagtacaa gtatatctct | 540 |
| ccaaaaaaat atttgaaatg accccaggga attttatata attgattgat agaaaaaatt | 600 |
| tagggaggtg ttcacatggc tgaattcttt ccagaaatcc cgaaagtgca gttcgaaggc | 660 |
| aaagaaagca caaatccact tgcgttcaag ttctacgatc cagaagagat catcgacggc | 720 |
| aaacccctca aggaccatct gaagttctcc gttgccttct ggcacacctt cgtgaacgag | 780 |
| ggaagggatc ccttcggaga cccaacggcc gatcgtccct ggaacaggta caccgatccc | 840 |
| atggacaagg cttttgcaag ggtggacgcc cttttgaat tctgcgaaaa actcaacatc | 900 |
| gagtacttct gcttccacga cagagacatc gctcccgagg gaaaaacgct gagggagaca | 960 |
| aacaaaattt tggacaaagt agtggagaga atcaaagaga gaatgaaaga cagcaacgtg | 1020 |
| aagctcctct gggtactgc aaacctctt tcccacccaa ggtacatgca tggtgcagcg | 1080 |
| acaacctgca gtgctgatgt tttgcggac gcggccgccc aggtgaaaaa agcccttgag | 1140 |
| atcaccaaag aacttggagg agaagggtac accttctggg gtggaagaga aggatacgaa | 1200 |
| acactcctca cacggacct tggattcgaa cttgaaaacc tcgcccgctt cctcagaatg | 1260 |
| gctgtggatt atgcaaaaag gatcggtttc accggacagt tcctcatcga ccaaaaccg | 1320 |
| aaagaaccca ccaaacacca gtacgacttc gacgttgcaa ccgcctatgc cttcctgaag | 1380 |
| agccacggtc tcgatgaata cttcaaattc aacatcgagg caaccacgc cacactcgcc | 1440 |
| ggtcacacct tccagcacga accgagaatg gcaaggatcc ttggaaaact cggaagcatc | 1500 |
| gatgcaaacc aggagacct tcttcttgga tgggacaccg atcagttccc aacaaacgtc | 1560 |
| tacgatacaa cccttgcaat gtacgaagtg ataaagcgg gaggcttcac aaaaggtggg | 1620 |
| ctcaacttcg atgcgaaggt gaggagggct tcttacaaag tggaggacct cttcataggg | 1680 |
| cacatagcgg gaatggacac ctttgcactc ggtttcaagg tggcatacaa actcgtgaag | 1740 |
| gatggtgttc tggacaaatt catcgaagaa agtacagaa gtttcaggga gggcattgga | 1800 |
| agggacatcg tcgaaggtaa agtggatttt gaaaacttg aagagtatat aatagacaaa | 1860 |

-continued

```
gaaacgatag aacttccatc tggaaagcaa gaatacctgg aaagcctcat caacagttac    1920
atagtgaaga ccattctgga actgaggtga acagagtgt gaagttcttg aatcttcgaa    1980
gattacttct tctggcactg attgcggctg aatctcagt gatcatagtc gtatccaacc    2040
gggaaaacag ggtgaaattt ccagaaggag agattgtgat aactgacgga gaaagatctc    2100
tgaaacttcg tgtcgagata gcgaacactc ctttttttcg ttcgatcggt ctgatgtaca    2160
gaaagagcat cccggatgac ttcgggatgc tctttgtttt tgaagaagat acaagaagcg    2220
gcttctggat gaagaacacc tacgttcccc tcgaaatcgc cttcatagac agaaacggca    2280
tcgtatttc cattcaggag atggagccat gcgaaaaaga accctgcaag gtttactacg    2340
caccaaagcc gttcagatac gctcttgaag tgaaagagg ttttttcgaa aggcatggat    2400
ttggagtggg aagccgtgtc ctgatagaaa agtagcggta ctttcaaaca aaaacgtatg    2460
gaatcttcat cttctttgcc tcgtacattc tcgagtcagc catcttcaga agttcttcta    2520
ga                                                                   2522
```

<210> SEQ ID NO 8
<211> LENGTH: 444
<212> TYPE: PRT
<213> ORGANISM: Thermotoga neapolitana

<400> SEQUENCE: 8

```
Met Ala Glu Phe Phe Pro Glu Ile Pro Lys Val Gln Phe Glu Gly Lys
  1               5                  10                  15

Glu Ser Thr Asn Pro Leu Ala Phe Lys Phe Tyr Asp Pro Glu Glu Ile
             20                  25                  30

Ile Asp Gly Lys Pro Leu Lys Asp His Leu Lys Phe Ser Val Ala Phe
         35                  40                  45

Trp His Thr Phe Val Asn Glu Gly Arg Asp Pro Phe Gly Asp Pro Thr
     50                  55                  60

Ala Asp Arg Pro Trp Asn Arg Tyr Thr Asp Pro Met Asp Lys Ala Phe
 65                  70                  75                  80

Ala Arg Val Asp Ala Leu Phe Glu Phe Cys Glu Lys Leu Asn Ile Glu
                 85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Asp Ala Ala Gln Val Lys Lys Ala Leu Glu Ile
                165                 170                 175

Thr Lys Glu Leu Gly Gly Glu Gly Tyr Thr Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255
```

```
His Gly Leu Asp Glu Tyr Phe Lys Phe Asn Ile Glu Ala Asn His Ala
            260                 265                 270

Thr Leu Ala Gly His Thr Phe Gln His Glu Pro Arg Met Ala Arg Ile
            275                 280                 285

Leu Gly Lys Leu Gly Ser Ile Asp Ala Asn Gln Gly Asp Leu Leu Leu
            290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
            355                 360                 365

Val Ala Tyr Lys Leu Val Lys Asp Gly Val Leu Asp Lys Phe Ile Glu
            370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
            435                 440

<210> SEQ ID NO 9
<211> LENGTH: 2522
<212> TYPE: DNA
<213> ORGANISM: Thermotoga neapolitana

<400> SEQUENCE: 9
gtcgacgcaa aggtcgtgac gggtggaaac ataaacgttc agctgggaac tgtgtcctcg      60
gctgctgttg aaggaacata cgttatcgaa gttggacaat tctctggaac ggtcacatcc     120
gagcttgatg tcaagatccg ccgttgtcct cagcacccct tccgtacacc ctgtcatcct     180
tcacaacggg gatgaaggga tccgtttccc acagcgaaag atcccctggt ggaacggtgt     240
ctatgtgtgt cactatccac aatgttttgc ttctgtccct gccgggaatg attgcaagca     300
gattcgacct ccaaattccg ttctggtctt ttgtgtcatg acgctcaaca gtgtatccca     360
tcttttttgag aagttcctcc agccagtcgg ccttctcttt ctctccaggt ccaccgaaga     420
ctggattcac cgaattgatc gatatgaacc ttttcagcga atctaccatt tcgtctttca     480
attcttctat ctttcttgtt atctccatct gaaacacctc ccaagtacaa gtatatctct     540
ccaaaaaaat atttgaaatg accccaggga attttatata attgattgat agaaaaaatt     600
tagggaggtg ttcacatggc tgaattcttt ccagaaatcc gaaagtgcag gttcgaaggc     660
aaagaaagca caaatccact tgcgttcaag ttctacgatc cagaagagat catcgacggc     720
aaaccccctca aggaccatct gaagttctcc gttgccttct ggcacacctt cgtgaacgag     780
ggaagggatc ccttcggaga cccaacggcc gatcgtccct ggaacaggta caccgatccc     840
atggacaagg cttttgcaag ggtggacgcc cttttttgaat tctgcgaaaa actcaacatc     900
gagtacttct gcttccacga cagagacatc gctcccgagg gaaaaacgct gagggagaca     960
aacaaaattt tggacaaagt agtggagaga atcaaagaga gaatgaaaga cagcaacgtg    1020
```

-continued

```
aagctcctct ggggtactgc aaacctcttt tcccacccaa ggtacatgca tggtgcagcg   1080
acaacctgca gtgctgatgt ttttgcggac gcggccgccc aggtgaaaaa agcccttgag   1140
atcaccaaag aacttggagg agaagggtac accttctggg gtggaagaga aggatacgaa   1200
acactcctca acacggacct tggattcgaa cttgaaaacc tcgcccgctt cctcagaatg   1260
gctgtggatt atgcaaaaag gatcggtttc accggacagt tcctcatcga accaaaaccg   1320
aaagaaccca ccaaacacca gtacgacttc gacgttgcaa ccgcctgtgc cttcctgaag   1380
agccacggtc tcgatgaata cttcaaattc aacatcgagg caaaccacgc cacactcgcc   1440
ggtcacacct tccagcacga accgagaatg caatgatcc ttggaaaact cggaagcatc    1500
gatgcaaacc agggagacct tcttcttgga tgggacaccg atcagttccc aacaaacgtc   1560
tacgatacaa cccttgcaat gtacgaagtg ataaaagcgg gaggcttcac aaaaggtggg   1620
ctcaacttcg atgcgaaggt gaggagggct tcttacaaag tggaggacct cttcataggg   1680
cacatagcgg gaatggacac cttttgcactc ggtttcaagg tggcatacaa actcgtgaag   1740
gatggtgttc tggacaaatt catcgaagaa agtacagaa gtttcaggga gggcattgga    1800
agggacatcg tcgaaggtaa agtggatttt gaaaaacttg aagagtatat aatagacaaa   1860
gaaacgatag aacttccatc tggaaagcaa gaatacctgg aaagcctcat caacagttac   1920
atagtgaaga ccattctgga actgaggtga acagagtgt gaagttcttg aatcttcgaa    1980
gattacttct tctggcactg attgcggctg aatctcagt gatcatagtc gtatccaacc    2040
gggaaaacag ggtgaaattt ccagaaggag agattgtgat aactgacgga gaaagatctc   2100
tgaaacttcg tgtcgagata gcgaacactc cttttttttcg ttcgatcggt ctgatgtaca   2160
gaaagagcat cccggatgac ttcgggatgc tctttgtttt tgaagaagat acaagaagcg   2220
gcttctggat gaagaacacc tacgttcccc tcgaaatcgc cttcatagac agaaacggca   2280
tcgtattttc cattcaggag atggagccat gcgaaaaaga accctgcaag gtttactacg   2340
caccaaagcc gttcagatac gctcttgaag tgaaagagg ttttttcgaa aggcatggat    2400
ttggagtggg aagccgtgtc ctgatagaaa agtagcggta ctttcaaaca aaaacgtatg   2460
gaatcttcat cttctttgcc tcgtacattc tcgagtcagc catcttcaga agttcttcta   2520
ga                                                                  2522
```

<210> SEQ ID NO 10
<211> LENGTH: 444
<212> TYPE: PRT
<213> ORGANISM: Thermotoga neapolitana

<400> SEQUENCE: 10

```
Met Ala Glu Phe Phe Pro Glu Ile Pro Lys Val Gln Phe Glu Gly Lys
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
```

```
                100                 105                 110
Arg Glu Thr Asn Lys Ile Leu Asp Lys Val Val Glu Arg Ile Lys Glu
            115                 120                 125

Arg Met Lys Asp Ser Asn Val Lys Leu Leu Trp Gly Thr Ala Asn Leu
        130                 135                 140

Phe Ser His Pro Arg Tyr Met His Gly Ala Thr Thr Cys Ser Ala
145                 150                 155                 160

Asp Val Phe Ala Asp Ala Ala Gln Val Lys Lys Ala Leu Glu Ile
                165                 170                 175

Thr Lys Glu Leu Gly Gly Glu Gly Tyr Thr Phe Trp Gly Gly Arg Glu
        180                 185                 190

Gly Tyr Glu Thr Leu Leu Asn Thr Asp Leu Gly Phe Glu Leu Glu Asn
            195                 200                 205

Leu Ala Arg Phe Leu Arg Met Ala Val Asp Tyr Ala Lys Arg Ile Gly
        210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Cys Ala Phe Leu Lys Ser
                245                 250                 255

His Gly Leu Asp Glu Tyr Phe Lys Phe Asn Ile Glu Ala Asn His Ala
        260                 265                 270

Thr Leu Ala Gly His Thr Phe Gln His Glu Pro Arg Met Ala Met Ile
    275                 280                 285

Leu Gly Lys Leu Gly Ser Ile Asp Ala Asn Gln Gly Asp Leu Leu Leu
        290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
    370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
        435                 440

<210> SEQ ID NO 11
<211> LENGTH: 443
<212> TYPE: PRT
<213> ORGANISM: Thermotoga neapolitana

<400> SEQUENCE: 11

Ala Glu Phe Phe Pro Glu Ile Pro Lys Val Gln Phe Glu Gly Lys Glu
1               5                   10                  15

Ser Thr Asn Pro Leu Ala Phe Lys Phe Tyr Asp Pro Glu Glu Ile Ile
            20                  25                  30
```

```
Asp Gly Lys Pro Leu Lys Asp His Leu Lys Phe Ser Val Ala Phe Trp
        35                  40                  45

His Thr Phe Val Asn Glu Gly Arg Asp Pro Phe Gly Asp Pro Thr Ala
        50                  55                  60

Asp Arg Pro Trp Asn Arg Tyr Thr Asp Pro Met Asp Lys Ala Phe Ala
65                  70                  75                  80

Arg Val Asp Ala Leu Phe Glu Phe Cys Glu Lys Leu Asn Ile Glu Tyr
                85                  90                  95

Phe Cys Phe His Asp Arg Asp Ile Ala Pro Glu Gly Lys Thr Leu Arg
                100                 105                 110

Glu Thr Asn Lys Ile Leu Asp Lys Val Val Glu Arg Ile Lys Glu Arg
            115                 120                 125

Met Lys Asp Ser Asn Val Lys Leu Leu Trp Gly Thr Ala Asn Leu Phe
        130                 135                 140

Ser His Pro Arg Tyr Met His Gly Ala Ala Thr Thr Cys Ser Ala Asp
145                 150                 155                 160

Val Phe Ala Tyr Ala Ala Ala Gln Val Lys Lys Ala Leu Glu Ile Thr
                165                 170                 175

Lys Glu Leu Gly Gly Glu Gly Tyr Thr Ser Trp Gly Gly Arg Glu Gly
                180                 185                 190

Tyr Glu Thr Leu Leu Asn Thr Asp Leu Gly Phe Glu Leu Glu Asn Leu
            195                 200                 205

Ala Arg Phe Leu Arg Met Ala Val Asp Tyr Ala Lys Arg Ile Gly Phe
        210                 215                 220

Thr Gly Gln Phe Leu Ile Glu Pro Lys Pro Lys Glu Pro Thr Lys His
225                 230                 235                 240

Gln Tyr Asp Phe Asp Val Ala Thr Ala Tyr Ala Phe Leu Lys Ser His
                245                 250                 255

Gly Leu Asp Glu Tyr Phe Lys Phe Asn Ile Glu Ala Asn His Ala Thr
                260                 265                 270

Leu Ala Gly His Thr Phe Gln His Glu Pro Arg Met Ala Arg Ile Leu
        275                 280                 285

Gly Lys Leu Gly Ser Ile Asp Ala Asn Gln Gly Asp Leu Leu Leu Gly
290                 295                 300

Trp Asp Thr Asp Gln Phe Pro Thr Asn Val Tyr Asp Thr Thr Leu Ala
305                 310                 315                 320

Met Tyr Glu Val Ile Lys Ala Gly Gly Phe Thr Lys Gly Gly Leu Asn
                325                 330                 335

Phe Asp Ala Lys Val Arg Arg Ala Ser Tyr Lys Val Glu Asp Leu Phe
                340                 345                 350

Ile Gly His Ile Ala Gly Met Asp Thr Phe Ala Leu Gly Phe Lys Val
            355                 360                 365

Ala Tyr Lys Leu Val Lys Asp Gly Val Leu Asp Lys Phe Ile Glu Glu
        370                 375                 380

Lys Tyr Arg Ser Phe Arg Glu Gly Ile Gly Arg Asp Ile Val Glu Gly
385                 390                 395                 400

Lys Val Asp Phe Glu Lys Leu Glu Glu Tyr Ile Ile Asp Lys Glu Thr
                405                 410                 415

Ile Glu Leu Pro Ser Gly Lys Gln Glu Tyr Leu Glu Ser Leu Ile Asn
            420                 425                 430

Ser Tyr Ile Val Lys Thr Ile Leu Glu Leu Arg
        435                 440
```

-continued

<210> SEQ ID NO 12
<211> LENGTH: 2522
<212> TYPE: DNA
<213> ORGANISM: Thermotoga neapolitana

<400> SEQUENCE: 12

| | | | | | |
|---|---|---|---|---|---|
| gtcgacgcaa | aggtcgtgac | gggtggaaac | ataaacgttc | agctgggaac | tgtgtcctcg | 60 |
| gctgctgttg | aaggaacata | cgttatcgaa | gttggacaat | tctctggaac | ggtcacatcc | 120 |
| gagcttgatg | tcaagatccg | ccgttgtcct | cagcacccct | tccgtacacc | ctgtcatcct | 180 |
| tcacaacggg | gatgaaggga | tccgtttccc | acagcgaaag | atccctggt | ggaacggtgt | 240 |
| ctatgtgtgt | cactatccac | aatgtttgc | ttctgtccct | gccgggaatg | attgcaagca | 300 |
| gattcgacct | ccaaattccg | ttctggtctt | tgtgtcatg | acgctcaaca | gtgtatccca | 360 |
| tcttttgag | aagttcctcc | agccagtcgg | ccttctcttt | ctctccaggt | ccaccgaaga | 420 |
| ctggattcac | cgaattgatc | gatatgaacc | ttttcagcga | atctaccatt | tcgtctttca | 480 |
| attcttctat | ctttcttgtt | atctccatct | gaaacacctc | ccaagtacaa | gtatatctct | 540 |
| ccaaaaaaat | atttgaaatg | accccaggga | atttatata | attgattgat | agaaaaaatt | 600 |
| tagggaggtg | ttcacatggc | tgaattcttt | ccagaaatcc | cgaaagtgca | gttcgaaggc | 660 |
| aaagaaagca | caaatccact | tgcgttcaag | ttctacgatc | cagaagagat | catcgacggc | 720 |
| aaacccctca | aggaccatct | gaagttctcc | gttgccttct | ggcacacctt | cgtgaacgag | 780 |
| ggaagggatc | ccttcggaga | cccaacggcc | gatcgtccct | ggaacaggta | caccgatccc | 840 |
| atggacaagg | cttttgcaag | ggtggacgcc | ctttttgaat | tctgcgaaaa | actcaacatc | 900 |
| gagtacttct | gcttccacga | cagagacatc | gctcccgagg | gaaaaacgct | gagggagaca | 960 |
| aacaaaattt | tggacaaagt | agtggagaga | tcaaagaga | gaatgaaaga | cagcaacgtg | 1020 |
| aagctcctct | ggggtactgc | aaacctcttt | tcccacccaa | ggtacatgca | tggtgcagcg | 1080 |
| acaacctgca | gtgctgatgt | ttttgcgtac | gcggccgccc | aggtgaaaaa | agcccttgag | 1140 |
| atcaccaaag | aacttggagg | agaagggtac | acctcctggg | gtggaagaga | aggatacgaa | 1200 |
| acactcctca | cacgacctt | ggattcgaa | cttgaaaacc | tcgcccgctt | cctcagaatg | 1260 |
| gctgtggatt | atgcaaaaag | gatcggtttc | accggacagt | tcctcatcga | accaaaaccg | 1320 |
| aaagaaccca | ccaaacacca | gtacgacttc | gacgttgcaa | ccgcctatgc | cttcctgaag | 1380 |
| agccacggtc | tcgatgaata | cttcaaattc | aacatcgagg | caaaccacgc | cacactcgcc | 1440 |
| ggtcacacct | tccagcacga | accgagaatg | gcaaggatcc | ttggaaaact | cggaagcatc | 1500 |
| gatgcaaacc | agggagacct | tcttcttgga | tgggacaccg | atcagttccc | aacaaacgtc | 1560 |
| tacgatacaa | cccttgcaat | gtacgaagtg | ataaaagcgg | gaggcttcac | aaaaggtggg | 1620 |
| ctcaacttcg | atgcgaaggt | gaggagggct | tcttacaaag | tggaggacct | cttcataggg | 1680 |
| cacatagcgg | gaatggacac | ctttgcactc | ggtttcaagg | tggcatacaa | actcgtgaag | 1740 |
| gatggtgttc | tggacaaatt | catcgaagaa | aagtacagaa | gtttcaggga | gggcattgga | 1800 |
| agggacatcg | tcgaaggtaa | agtggatttt | gaaaaacttg | aagagtatat | aatagacaaa | 1860 |
| gaaacgatag | aacttccatc | tggaaagcaa | gaatacctgg | aaagcctcat | caacagttac | 1920 |
| atagtgaaga | ccattctgga | actgaggtga | acagagtgt | gaagttcttg | aatcttcgaa | 1980 |
| gattacttct | tctggcactg | attgcggctg | gaatctcagt | gatcatagtc | gtatccaacc | 2040 |
| gggaaaacag | ggtgaaattt | ccagaaggag | agattgtgat | aactgacgga | gaaagatctc | 2100 |
| tgaaacttcg | tgtcgagata | gcgaacactc | cttttttcg | ttcgatcggt | ctgatgtaca | 2160 |

-continued

```
gaaagagcat cccggatgac ttcgggatgc tctttgtttt tgaagaagat acaagaagcg    2220
gcttctggat gaagaacacc tacgttcccc tcgaaatcgc cttcatagac agaaacggca    2280
tcgtattttc cattcaggag atggagccat gcgaaaaaga accctgcaag gtttactacg    2340
caccaaagcc gttcagatac gctcttgaag tgaaaagagg ttttttcgaa aggcatggat    2400
ttggagtggg aagccgtgtc ctgatagaaa agtagcggta ctttcaaaca aaaacgtatg    2460
gaatcttcat cttctttgcc tcgtacattc tcgagtcagc catcttcaga agttcttcta    2520
ga                                                                   2522
```

THERMOTOGA NEAPOLITANA XYLOSE ISOMERASE POLYPEPTIDES AND NUCLEIC ACIDS ENCODING SAME

CROSS-REFERENCE TO RELATED APPLICATIONS

This application claims priority to provisional applications Ser. No. 60/350,930, filed Jan. 23, 2002 and Ser. No. 60/428,064, filed Nov. 21, 2002.

GOVERNMENT RIGHTS

This invention was made with government support under Grant Nos. BES9809964 and 0115754 awarded by the National Science Foundation. The government has certain rights in the invention.

FIELD OF THE INVENTION

The invention relates to nucleic acids and polypeptides encoding xylose isomerases, as well as vectors, host cells, antibodies and recombinant methods for producing the polypeptides and polynucleotides.

BACKGROUND OF THE INVENTION

The recent expansion of the world market for High Fructose Corn Syrup (HFCS) makes potential improvements in HFCS production that would result from increased isomerization yields, increased cost effectiveness and elimination of non-enzymatic browning (Maillard browning reaction) by-products considerable. HFCS producing industries are interested in a highly stable xylose (glucose) isomerase that is active at about 60° C. and slightly acidic pH instead of at neutral or slightly basic pH. A thermo-acid-stable xylose (glucose) isomerase would be used to eliminate the onset of by-products of browning reactions and increase the time between biocatalyst replacements.

Xylose isomerase (XI) converts D-xylose to D-xylulose in vivo and also catalyzes the conversion of D-glucose to D-fructose in vitro. This latter activity is used in industry for the production of high fructose corn syrup (HFCS). XI is one of the largest volume commercial enzymes used today. Typically, the pH optima of commercially available glucose isomerases range from about 7.5 to about 9.0. This range limits the reaction temperature used in the industrial glucose isomerization process to around 60° C. due to the formation of browning products by non-enzymatic reactions between reducing sugars and proteins at higher temperatures and alkaline pHs. Thermostable XIs with neutral or slightly acidic pH optima have a potential for industrial applications with the advantages of faster reaction rates, higher fructose concentrations at equilibrium, higher process stability, decreased viscosity of substrate and product streams, and fewer problems with by-product formation.

Numerous and intensive site-directed mutagenesis studies have been performed to improve enzyme catalysts. Despite these efforts, no generally applicable rules have been established to develop acid-stable or thermostable enzyme catalysts. Besides, rules for engineering protein stability and activity by rational design are likely to be protein-specific, and any such design effort would need to be guided by detailed structural information. Directed evolution, on the other hand, has proved to be useful for modifying enzymes in the absence of such knowledge.

An ideal XI suitable for use in the HFCS industry should meet the following conditions: (a) it should function under acidic conditions (pH of about 6 or less) to avoid browning reactions; (b) it should function under higher reaction temperatures than current commercial XIs and lower reaction temperatures than thermophilic xylose isomerases' optimal temperature for activity, that is, from about 60° C. to about 80° C.; and (c) it should retain high stability at high temperature.

It would require enormous effort, time, and structural knowledge to use a site-directed mutagenesis approach to try to engineer such an enzyme. Directed evolution has proved to be useful for modifying enzymes in the absence of structural knowledge (Kuchner and Arnold, 1997). In directed evolution, the process of natural evolution is accelerated in a test tube for selecting proteins with the desired properties (Moore and Maranas, 2000).

A basic protocol for directed evolution starts with the creation of a library of mutated genes encoding for the protein of interest, usually by means of error-prone PCR (also known as random mutagenesis). Once created, these genes are then ligated into an expression vector and transformed into suitable bacterial cells. A screening procedure is then applied to isolate the few transformants containing mutated genes that encode for proteins with improved properties. Proteins with different properties can be recombined using a DNA shuffling approach (Stemmer, 1994 and Zhao and Arnold, 1997).

U.S. Pat. Nos. 5,219,751, 5,268,280, 5,656,497, and 5,935,837, which are hereby incorporated by reference in their entirety, disclose glucose isomerases obtained from *Thermotoga maritima* and *Thermotoga neapolitana*. However, these patents do not disclose DNA constructs encoding enzymes that are capable of preparing D-fructose by enzymatically treating D-glucose with the xylose isomerase at a lower reaction temperature (from about 45° C. to about 100° C.) and under acidic conditions (pH of about 5.2 to about 7.0) to obtain a syrup containing up to about 60–65% D-fructose.

Vieille et al., Appl. Environ. Microbiol. 1995 61 (5) 1867–1875, describe a gene derived from a strain of *Thermotoga neapolitana*, encoding a xylose isomerase, which consists of 444 amino acid residues, and has a calculated molecular weight of 50,892.

Previous attempts have been made to obtain thermostable xylose isomerases, either by site-directed mutagenesis of moderately thermostable xylose isomerases, or by screening highly thermophilic organisms for xylose isomerase activity. However, none of those attempts have resulted in commercially useful xylose isomerases that allow processing of sugars at a reduced temperature.

Therefore, it would be advantageous to have a xylose isomerase with enhanced stability, activity, and utility and an efficient method of producing that enzyme in quantity.

Objects

It is an object of the present invention to disclose a novel xylose isomerase ("XI").

It is a further object to disclose a method of producing the enzyme employing DNA encoding for the enzymes, plasmids containing the DNA, and bacteria into which the plasmids have been inserted and which produce the enzyme.

It is a still further object to disclose a method of making fructose using the novel xylose isomerase.

The present invention relates to a xylose isomerase, which is obtained from the microorganism *Thermotoga neapolitana* and nucleic acids encoding for such isomerase. The enzyme has the amino acid sequence of SEQ ID NO:4, SEQ ID NO:6, SEQ ID NO:8, SEQ ID NO:10 or SEQ ID NO:11. Preferably, the enzyme has the amino acid sequence SEQ ID NO:4, which is:

```
TNX1 3A2 (V185T,L282P)
MAEFFPEIPK VQFEGKESTN PLAFKFYDPE EIIDGKPLKD HLKFSVAFWH TFVNEGRDPF
60

GDPTADRPWN RYTDPMDKAF ARVDALFEFC EKLNIEYFCF HDRDIAPEGK TLRETNKILD
120

KVVERIKERM KDSNVKLLWG TANLFSHPRY MHGAATTCSA DVFAYAAAQV KKALEITKEL
180

GGEGYTFWGG REGYETLLNT DLGFELENLA RFLRMAVDYA KRIGFTGQFL IEPKPKEPTK
240

HQYDFDVATA YAFLKSHGLD EYFKFNIEAN HATLAGHTFQ HEPRMARILG KLGSIDANQG
300

DLLLGWDTDQ FPTNVYDTTL AMYEVIKAGG FTKGGLNFDA KVRRASYKVE DLFTGHIAGM
360

DTFALGFKVA YKLVKDGVLD KEIEEKYRSF REGIGRDIVE GKVDFEKLEE YIIDKETIEL
420

PSGKQEYLES LINSYIVKTI LELR
444
```

The preferred enzyme has the amino acid sequence SEQ ID NO:11, which is:

```
TNXI 1F1 (V185T/F186S/L282P)deduced amino acid sequence

1           .           .           .           .           .           .           .           80
AEFFPEIPKVQFEGKESTNPLAFKFYDPEEIIDGKPLKDHLKFSVAFWHTFVNEGRDPFGDPTADRPWNRYTDPMDKAFA

81          .           .           .           .           .           .           .           160
RVDALFEFCEKLNIEYFCFHDRDIAPEGKTLRETNKILDKVVERIKERMKDSNVKLLWGTANLFSHPRYMHGAATTCSAD

161         .           .           .           .           .           .           .           240
VFAYAAAQVKKALEITKELGGEGYTSWGGREGYETLLNTDLGFELENLARFLRMAVDYAKRIGFTGQFLIEPKPKEPTKH

241         .           .           .           .           .           .           .           320
QYDFDVATAYAFLKSHGLDEYFKFNIEANHATLAGHTFQHEPRMARILGKLGSIDANQGDLLLGWDTDQFPTNVYDTTLA

321         .           .           .           .           .           .           .           400
MREVIKAGGFTKGGLNFDAKVRRASYKVEDLFIGHIAGMDTFALGFKVAYKLVKDGVLDKFIEEKYRSFREGIGRDIVEG

401         .           .           .           .           .           .           .           480
KVDFEKLEEYIIDKETIELPSGKQEYLESLINSYIVKTILELR*******
```

This is TNX1F1 (V185T, F186S, L282P) or SEQ ID NO:11 (FIG. 19).

The preferred method of the present invention for producing the enzyme, comprises, isolating and purifying xylose isomerase gene, partially digesting the DNA with a restriction enzyme, ligating the DNA into a plasmid vector, transforming the E. coli with the ligation mixture, growing the E. coli and isolating the enzyme from the E. coli.

The novel isolated xylose isomerase gene has the nucleotide sequence of SEQ ID NO:3, SEQ ID NO:5, SEQ ID NO:7, or SEQ ID NO:9. Preferably, the novel isolated xylose isomerase gene has the nucleotide sequence of SEQ ID NO:3. The nucleotide sequence SEQ ID NO:3 is:

```
TNX1 3A2 (V185T,L282P)
gtcgacgcaa aggtcgtgac gggtggaaac ataaacgttc agctgggaac tgtgtcctcg
60 gctgctgttg aaggaacata cgttatcgaa gttggacaat tctctggaac ggtcacatcc
120 gagcttgatg tcaagatccg ccgttgtcct cagcacccct tccgtacacc ctgtcatcct
180 tcacaacggg gatgaaggga tccgtttccc acagcgaaag atccctggt ggaacggtgt
240 ctatgtgtgt cactatccac aatgttttgc ttctgtccct gccgggaatg attgcaagca
300
```

-continued

```
gattcgacct ccaaattccg ttctggtctt ttgtgtcatg acgctcaaca gtgtatccca    360 tcttttgag aagttcctcc agccagtcgg ccttctcttt ctctccaggt ccaccgaaga    420
ctggattcac cgaattgatc gatatgaacc ttttcagcga atctaccatt tcgtctttca    480
attcttctat ctttcttgtt atctccatct gaaacacctc ccaagtacaa gtatatctct    540
ccaaaaaaat atttgaaatg accccaggga attttatata attgattgat agaaaaaatt    600
tagggaggtg ttcacatggc tgaattcttt ccagaaatcc gaaagtgca gttcgaaggc     660 aaagaaagca caaatccact tgcgttcaag ttctacgatc cagaagagat catcgacggc    720 aaaccccctca aggaccatct gaagttctcc gttgccttct ggcacacctt cgtgaacgag   780 gaagggatc ccttcggaga cccaacggcc gatcgtccct ggaacaggta caccgatccc     840
atggacaagg cttttgcaag ggtggacgcc ctttttgaat tctgcgaaaa actcaacatc    900
gagtacttct gcttccacga cagagacatc gctcccgagg gaaaaacgct gagggagaca    960
aacaaaattt tggacaaagt agtggagaga atcaaagaga gaatgaaaga cagcaacgtg    1020
aagctcctct ggggtactgc aaacctcttt tcccacccaa ggtacatgca tggtgcagcg    1080
acaacctgca gtgctgatgt ttttgcgtac gcggccgccc aggtgaaaaa agcccttgag    1140
atcaccaaag aacttggagg agaagggtac accttctggg gtggaagaga aggatacgaa    1200
acactcctca acacggacct tggattcgaa cttgaaaacc tcgcccgctt cctcagaatg    1260
gctgtggatt atgcaaaaag gatcggtttc accggacagt tcctcatcga accaaaaccg    1320
aaagaaccca ccaaacacca gtacgacttc gacgttgcaa ccgcctatgc cttcctgaag    1380
agccacggtc tcgatgaata cttcaaattc aacatcgagg caaaccacgc cacactcgcc    1440
ggtcacacct tccagcacga accgagaatg gcaaggatcc ttggaaaact cggaagcatc    1500
gatgcaaacc agggagacct tcttcttgga tgggacaccg atcagttccc aacaaacgtc    1560
tacgatacaa cccttgcaat gtacgaagtg ataaaagcgg gaggcttcac aaaaggtggg    1620
ctcaacttcg atgcgaaggt gaggagggct tcttacaaag tggaggacct cttcataggg    1680
cacatagcgg gaatggacac ctttgcactc ggtttcaagg tggcatacaa actcgtgaag    1740
gatggtgttc tggacaaatt catcgaagaa agtacagaa gtttcaggga gggcattgga    1800
agggacatcg tcgaaggtaa agtggatttt gaaaaacttg aagagtatat aatagacaaa    1860
```

-continued

```
gaaacgatag aacttccatc tggaaagcaa gaatacctgg aaagcctcat caacagttac
1920 atagtgaaga ccattctgga actgaggtga aacagagtgt gaagttcttg aatcttcgaa
1980 gattacttct tctggcactg attgcggctg aatctcagt gatcatagtc gtatccaacc
2040 gggaaaacag ggtgaaattt ccagaaggag agattgtgat aactgacgga gaaagatctc
2100 tgaaacttcg tgtcgagata gcgaacactc cttttttcg ttcgatcggt ctgatgtaca
2160 gaaagagcat cccggatgac ttcgggatgc tctttgtttt tgaagaagat acaagaagcg
2220 gcttctggat gaagaacacc tacgttcccc tcgaaatcgc cttcatagac agaaacggca
2280 tcgtattttc cattcaggag atggagccat gcgaaaaaga accctgcaag gtttactacg
2340 caccaaagcc gttcagatac gctcttgaag tgaaaagagg ttttttcgaa aggcatggat
2400 ttggagtggg aagccgtgtc ctgatagaaa agtagcggta ctttcaaaca aaaacgtatg
2460 gaatcttcat cttctttgcc tcgtacattc tcgagtcagc catcttcaga agttcttcta
2520
```

The nucleotide sequence of SEQ ID NO:12 is:

```
TNXI 1F1 nucleotide sequence (ORF starting at 616 bp)
1          .         .         .         .         .         .         .         .   80
GTCGACGCAAAGGTCGTGACGGGTGGAAACATAAACGTTCAGCTGGGAACTGTGTCCTCGGCTGCTGTTGAAGGAACATA 81         .         .         .         .         .         .         .         .   160
CGTTATCGPAGTTGGACAATTCTCTGGAACGGTCACATCCGAGCTTGATGTCAAGATCCGCCGTTGTCCTCAGCACCCCT 161        .         .         .         .         .         .         .         .   240
TCCGTACACCCTGTCATCCTTCACAACGGGGATGAGGGATCCGTTTCCCACAGCGAAGATCCCCTGGTGGAACGGTGT 241        .         .         .         .         .         .         .         .   320
CTATGTGTGTCACTATCCACAATGTTTTGCTTCTGTCCCTGCCGGGAATGATTGCAAGCAGATTCGACCTCCAAATTCCG 321        .         .         .         .         .         .         .         .   400
TTCTGGTTTTTGTGTCATGACGCTCAACAGTGTATCCCATCTTTTTGAGAAGTTCCTCCAGCCAGTCGGCCTTCTCTTT 401        .         .         .         .         .         .         .         .   480
CTCTCCAGGTCCACCGAAGACTGGATTCACCGAATTGATCGATATGAACCTTTTCAGCGAATCTACCATTTCGTCTTTCA 481        .         .         .         .         .         .         .         .   560
ATTCTTCTATCTTTCTTGTTATCTCCATCTGAAACACCTCCCAAGTACAAGTATATCTCTCCAAAAAAATATTTGAAATG 561        .         .         .         .         .       ***.         .            640
ACCCCAGGGAATTTTATATAATTGATTGATAGAAAAAATTTAGGGAGGTGTTCACATGGCTGAATTCTTTCCAGAAATCC
                                                         A   E   F   F   P   E   I 641        .         .         .         .         .         .         .         .   720
CGAAAGTGCAGTTCGAAGGCAAAGAAAGCACAAATCCACTTGCGTTCAAGTTCTACGATCCAGAAGAGATCATCGACGGC
 P   K   V   Q   K   E   G   K   E   S   T   N   P   L   A   F   K   F   Y   D   P   E   E   I   I   D   G 721        .         .         .         .         .         .         .         .   800
AAACCCCTCAAGGACCATCTGAAGTTCTCCGTTGCCTTCTGGCACACCTTCGTGAACGAGGGAAGGGATCCCTTCGGAGA
  K   P   L   K   D   H   L   K   F   S   V   A   F   W   H   T   F   V   N   H   G   R   D   P   F   G   D 801        .         .         .         .         .         .         .         .   880
CCCAACGGCCGATCGTCCCTGGAACAGGTACACCGATCCCATGGACAAGGCTTTTGCAAGGGTGGACGCCGTTTTTGAAT
   P   T   A   D   R   P   W   N   R   Y   T   D   P   M   D   K   A   F   A   R   V   D   A   L   F   E 881        .         .         .         .         .         .         .         .   960
TCTGCGAAAAACTCAACATCGAGTACTTCTGCTTCCPCGACAGAGACATCGCTCCCGAGGGAAAAACGCTGAGGGAGACA
```

-continued

```
           F  C  E  K  L  N  I  E  Y  F  C  F  H  D  R  D  I  A  P  H  G  K  T  L  R  E  T

961          .           .           .           .           .           .           .           .      1040
AACAAAATTTTGGACAAAGTAGTGGAGAGAATCAAAGAGAGAATGAAAGACAGCAAGGTGAAGCTCCTCTGGGGTACTGC
  N  K  I  L  D  K  V  V  E  R  I  K  E  R  M  K  D  S  N  V  K  L  L  W  G  T  A

1041         .           .           .           .           .           .           .           .      1120
AAACCTCTTTTCCCACCCAAGGTACATGCATGGTGCAGCGACAACCTGCAGTGCTGATGTTTTTGCGTACGCGGCCGCCC
   N  L  F  S  H  P  R  Y  M  H  G  A  A  T  T  C  S  A  D  V  F  A  Y  A  A  A

1121         .           .           .           .           .           .           .           .      1200
AGGTGAAAAGCCCTTGAGATCACCAAGAACTTGGAGGAGAAGGGTACACCTCCTGGGGTGGAAGAGAAGGATACGAA
  Q  V  K  K  A  L  E  I  T  K  E  L  G  G  E  G  Y  T  S  W  G  G  R  E  G  Y  E

1201         .           .           .           .           .           .           .           .      1280
ACACTCCTCAACACGGACCTTGGATTCGAACTTGAAAACCTCGCCCGCTTCCTCAGAATGGCTGTGGATTATGCAAAAAG
  T  L  L  N  T  O  L  G  F  E  L  H  N  L  A  R  F  L  R  M  A  V  D  Y  A  K  R

1281         .           .           .           .           .           .           .           .      1360
GATCGGTTTCACCGGACAGTTCCTATCGAACCAAAACCGAAAGAACCCACCAACACCAGTACGACTTCGACGTTGCAA
   I  G  F  T  G  Q  F  L  I  H  P  K  P  K  E  P  T  K  H  Q  Y  O  F  D  V  A

1361         .           .           .           .           .           .           .           .      1440
CCGCCTATGCCTTCCTGAAGAGCCACGGTCTCGATGAATACTTCAAATTCAACATCGAGGCAACCACGCCACACTCGCC

1441         .           .           .           .           .           .           .           .      1520
GGTCACACCTTCCAGCACGAACCGAGAATGGCAAGGATCCTTGGAAAACTGGAAGCATCGATGCAAACCAGGGAGACCT
  G  H  T  F  Q  H  E  P  R  M  A  R  I  L  G  K  L  G  S  I  D  A  N  Q  G  D  L

1521         .           .           .           .           .           .           .           .      1600
TCTTCTTGGATGGGACACCGATCAGTTCCCAACAAACGTCTACGATACAACCCTTGCAATGTACGAAGTGATAAAAGCGG
   L  L  G  W  D  T  D  Q  F  P  T  N  V  Y  D  T  T  L  A  M  Y  E  V  I  K  A

1601         .           .           .           .           .           .           .           .      1680
GAGGCTTCACAAGGTGGGTCAACTTCGATGGGAAGGTGAGGAGGGCTTCTTACAAAGTGGAGGACCTCTTCATAGGG
  G  G  F  T  K  G  G  L  H  F  D  A  K  V  R  R  A  S  Y  K  V  E  D  L  F  I  G

1681         .           .           .           .           .           .           .           .      1760
CACTAGCGGGAATGGACACCTTTGCACTCGGTTTCAAGGTGGCATACACTCGTGAAGGATGGTGTTCTGGACAAATT
   H  I  A  G  M  D  T  F  A  L  G  F  K  V  A  Y  K  L  V  K  D  G  V  L  D  K  F

1761         .           .           .           .           .           .           .           .      1840
CATCGAAGAAAAGTACAGAAGTTCAGGGAGGGCATTGGAAGGGACATCGTCGAAGGTAAAGTGGATTTTGAAAAACTTG
    I  E  E  K  Y  R  S  F  R  E  G  I  G  R  D  I  V  E  G  K  V  D  F  E  K  L

1841         .           .           .           .           .           .           .           .      1920
AAGAGTATATAATAGACAAGAAACGATAGAACTTCCATCTGGAAAGCAAGAATACCTGGAAAGCCTCATCAACAGTTAC
  E  E  Y  I  I  D  K  E  T  I  E  L  P  S  G  K  Q  E  Y  L  E  S  L  I  H  S  Y

1921         .           .     ***   .           .           .           .           .      2000
ATAGTGAAGACCATTCGGAACTGAGGTGAAACAGAGTGTGAAGTTCTTGAATCTTCGAAGATTACTTCTTCTGGCACTG
   I  V  K  T  I  L  E  L  R

ATTGCGGCTGGAATCTCAGTGATCATAGTCGTATCCAACCGGGAAAACAGGGTGAAATTTCCAGAAGGAGAGATTGTGAT
AACTGACGGAGAAAGATCTCTGAAACTTCGTGTCAGATAGCGAACACTCCTTTTTTTCGTTCGATCGGTCTGATGTACA
GAAAGAGCATCCCGGATGACTTCGGGATGCTCTTTGTTTTTGAAGAAGATACAAGAAGCGGCTTCTGGATGAAGAACACC
TACGTTCCCCTCGAAATCGCCTTCATAGACAGAAACGGCATCGTATTTTCCATTCAGGAGATGGAGCCATGCGAAAAGA
ACCCTGCAAGGTTTACTACGCACCAAAGCCGTTCAGATACGCTCTTGAAGTGAAAAGAGGTTTTTTCGAAAGGCATGGAT
TTGGAGTGGGAAGCCGTGTCCTGATAGAAAAGTAGCGGTACTTTCAAACAAAAACGTATGGAATCTTCATCTTCTTTGCC
TCGTACATTCTCGAGTCAGCCATCTTCAGAAGTTCTTCTAGA

TNXI 1F1 [V185T, F186S, and     185:GTC(Val)→ACC(Thr)
L282P]
                                186:TTC (Phe)→TCC (Ser)
                                282:CTG (Leu)→CCG (Pro)
```

The novel recombinant plasmid comprises a compatible vector containing the DNA sequence of SEQ ID NO:3, SEQ ID NO:5, SEQ ID NO:7, or SEQ ID NO:9 or SEQ ID NO:12. A compatible vector is one into which the gene can be inserted and which can be introduced into a suitable host for production of the enzyme.

The preferred method of preparing D-fructose comprises enzymatically treating D-glucose with the xylose isomerase of the present invention at a temperature of about 45° C. to about 100° C. at a pH of about 5.2 to about 8.0 to obtain a syrup containing up to about 50 to about 60% D-fructose.

The achievement of the above and other objects and advantages of the present invention will be apparent to those skilled in the art from the description of the drawings, the preferred embodiment and the experimental work.

In one aspect, the invention provides a purified polypeptide that includes an amino acid sequence at least 80% identical to amino acids 2–444 of SEQ ID NO:4, SEQ ID NO:6, SEQ ID NO:8, or SEQ ID NO:10. A preferred polypeptide is an amino acid sequence at least 95% identical to amino acids 2–444 of SEQ ID NO:4, SEQ ID NO:6, SEQ ID NO:8, SEQ ID NO:10 or SEQ ID NO:11.

In another aspect, the invention provides an isolated nucleic acid molecule encoding an XI polypeptide. In preferred embodiments, the encoded polypeptide comprising an amino acid sequence at least 80% identical to amino acids 2–444 of SEQ ID NO:4, SEQ ID NO:6, SEQ ID NO:8, SEQ ID NO:10 or SEQ ID NO:12.

A preferred nucleic acid encodes a polypeptide that includes an amino acid sequence at least 95% identical to amino acids 2–444 of SEQ ID NO:4, SEQ ID NO:6, SEQ ID NO:8, SEQ ID NO:10 or SEQ ID NO:11.

The invention also includes an oligonucleotide that includes a portion of an XI encoding nucleic acid. For example, the oligonucleotide can be at least 10 nucleotides in length and include at least nine contiguous nucleotides of SEQ ID NO:3, SEQ ID NO:5, SEQ ID NO:7, SEQ ID NO:9 or SEQ ID NO:12.

Also provided by the invention is a vector that includes an XI encoding nucleic acid. The vector can include, e.g., a nucleic acid encoding an XI polypeptide that includes an amino acid sequence at least 80% identical to amino acids 2–444 of SEQ ID NO:4, SEQ ID NO:6, SEQ ID NO:8, SEQ ID NO:10 or SEQ ID NO:11. In a further aspect, the invention includes a cell that includes the XI nucleic acid-containing vector.

In a further aspect, the invention provides an antibody that selectively binds to an XI polypeptide, e.g., a polypeptide that includes an amino acid sequence at least 80% identical to amino acids 2–444 of SEQ ID NO:4, SEQ ID NO:6, SEQ ID NO:8, SEQ ID NO:10 or SEQ ID NO:11. The antibody can be a polyclonal antibody or a monoclonal antibody. In some embodiments, the antibody neutralizes the isomerase activity of an XI polypeptide.

The invention also includes a method of producing an XI polypeptide by culturing a cell that includes an XI-encoding nucleic acid under conditions allowing for expression of the polypeptide encoded by the XI nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 shows (a) a representation of the TNXI xylose isomerase clone nucleotide sequence (SEQ ID NO:3; ORF starting at 616 bp); (b) a representation of the TNXI xylose isomerase clone deduced encoded amino acid sequence (SEQ ID NO:4); and (c) mutations to the native glucose isomerase gene.

FIG. 5B is a graph showing Ln (specific activity) versus 1/Temperature. All linear regressions had $r^2$ values above 0.97.

(FIG. 17A at 80° C. and FIG. 17B at 60° C.

FIG. 19 is the deduced amino acid sequence (SEQ ID NO:11) of TNXI 1F1.

FIG. 20 is the DNA sequence (SEQ ID NO:12) which encodes TNXI 1F1.

DETAILED DESCRIPTION OF THE INVENTION

Figure 2:
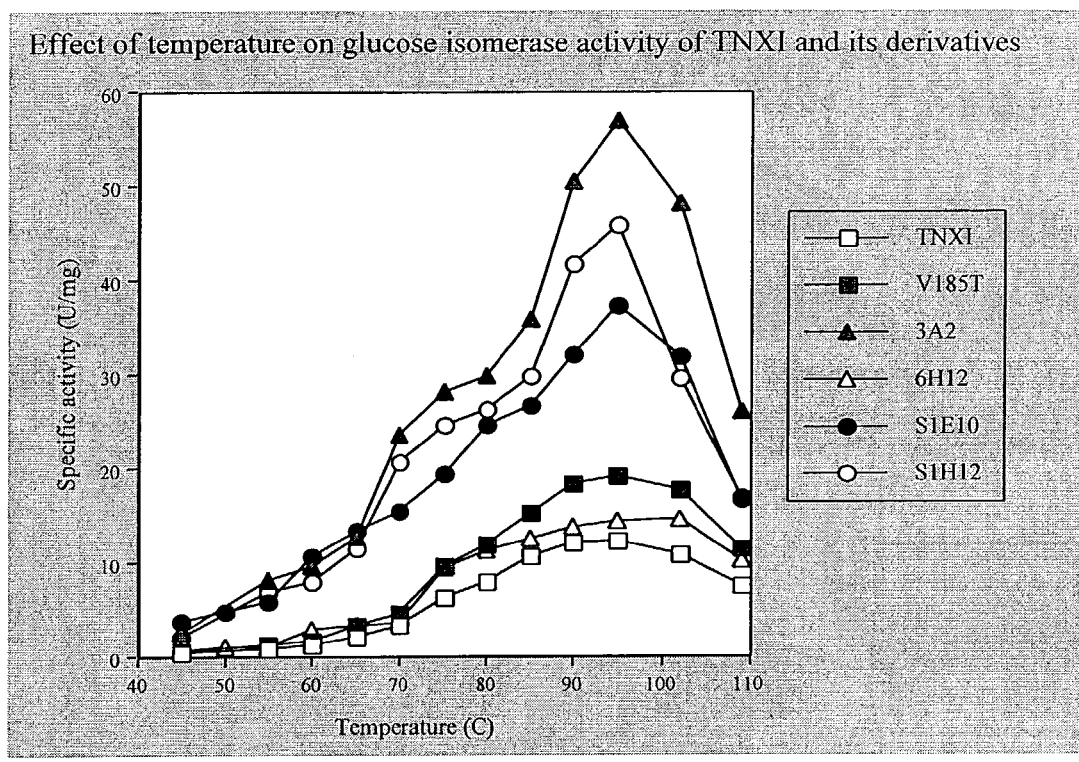
FIG. 2 is a graph showing the effect of temperature on glucose isomerase activity of TNXI and its derivatives.

The invention provides nucleic acids encoding novel polypeptides with improved xylose isomerase activity.

Nucleic acids and polypeptides according to the invention are referred to herein as "XI" nucleic acids and polypeptides. The nucleic acids of the invention include those that encode an XI polypeptide or protein. As used herein, the terms polypeptide and protein are interchangeable.

By "improved properties" as used herein in connection with the present glucose isomerase enzymes, we mean higher conversion performance and/or improved stability, especially heat stability, relative to the corresponding wild-type enzymes. In addition, increased stability at different pH as such or in combination with enhanced thermostability is considered with the term "improved properties".

In some embodiments, an XI nucleic acid encodes a mature XI polypeptide. As used herein, a "mature" form of a polypeptide or protein described herein relates to the product of a naturally occurring polypeptide or precursor form or preprotein. The naturally occurring polypeptide, precursor or proprotein includes, by way of nonlimiting example, the full-length gene product, encoded by the corresponding gene. Alternatively, it may be defined as the polypeptide, precursor or preprotein encoded by an open reading frame described herein. A preferred mature polypeptide includes amino acids 2–444 of SEQ ID NO:4. It should be understood by those skilled in the art that various leader sequences may be used so long as the functioning peptide can be formed.

In some embodiments, the product "mature" form arises as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus, a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

In the present specification both the three letter and the one letter code for amino acids is used. This code is explained in the following Table 1:

TABLE 1

| Alanine | Ala | A; | Leucine | Leu | L |
| Arginine | Arg | R; | Lysine | Lys | K |
| Asparagine | Asn | N; | Methionine | Met | M |
| Aspartic acid | Asp | D; | Phenylalanine | Phe | F |
| Cysteine | Cys | C; | Proline | Pro | P |
| Glutamic acid | Glu | E; | Serine | Ser | S |
| Glutamine | Gln | Q; | Tryptophan | Trp | W |
| Histidine | His | H; | Tyrosine | Tyr | Y |
| Isoleucine | Ile | I; | Valine | Val | V |
| Threonine | Thr | T | Glycine | Gly | G |

Among the XI nucleic acids is the nucleic acid whose sequence is provided in SEQ ID NO:3, SEQ ID NO:5, SEQ ID NO:7 or SEQ ID NO:9, or a fragment thereof. Additionally, the invention includes mutant or variant nucleic acids of SEQ ID NO:3, SEQ ID NO:5, SEQ ID NO:7 OR SEQ ID NO:9, or a fragment thereof, any of whose bases may be changed from the corresponding bases shown in SEQ ID NO:3, SEQ ID NO:5, SEQ ID NO:7 or SEQ ID NO:9, while still encoding a protein that substantially maintains its XI-like activities. The invention further includes the complement of the nucleic acid sequence of SEQ ID NO:3, SEQ ID NO:5, SEQ ID NO:7 or SEQ ID NO:9, including fragments, derivatives, analogs and homologs thereof. The invention additionally includes nucleic acids or nucleic acid fragments, or complements thereto, whose structures include chemical modifications.

Sequence analysis of the plasmid carrying the XI gene reveals an insert size of 1335 bps. bases. The cDNA sequence includes an open reading frame that extends from nucleotide 616 to 1950 (SEQ ID NO:3, SEQ ID NO:5, SEQ ID NO:7 and SEQ ID NO:9). The amino acid sequence deduced from this cDNA specifies a 444 amino acid protein. An open reading frame encoding a 444 amino acid protein (SEQ ID NO:4, SEQ ID NO:6, SEQ ID NO:8 and SEQ ID NO:10) is present. The initiation codon (ATG) includes nucleotides 616–618 and the termination codon (TGA) includes nucleotides 1948–1950. The termination or stop codons can comprise any of the sequences TAA, TAG or TGA.

One aspect of the invention pertains to isolated nucleic acid molecules that encode XI proteins or biologically active portions thereof. Also included are nucleic acid fragments sufficient for use as hybridization probes to identify XI-encoding nucleic acids (e.g., XI mRNA) and fragments for use as polymerase chain reaction (PCR) primers for the amplification or mutation of XI nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated XI nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

"Probes" refer to nucleic acid sequences of variable length, preferably at least about 10 nucleotides (nt), but can be about 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

A nucleic acid molecule of the present invention, e.g., a nucleic acid molecule having the nucleotide sequence of SEQ ID NO:3, SEQ ID NO:5, SEQ ID NO:7 or SEQ ID NO:9, or a complement thereof, can be isolated using standard molecular biology techniques and the sequence information provided herein. Using all or a portion of the nucleic acid sequence of SEQ ID NO:3, SEQ ID NO:5, SEQ ID NO:7 or SEQ ID NO:9, as a hybridization probe, XI nucleic acid sequences can be isolated using standard hybridization and cloning techniques.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to XI nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:3, SEQ ID NO:5, SEQ ID NO:7 OR SEQ ID NO:9, or a portion of this nucleotide sequence. A nucleic acid molecule that is complementary to the nucleotide sequence shown in SEQ ID NO:3, SEQ ID NO:5, SEQ ID NO:7 or SEQ ID NO:9 is one that is sufficiently complementary to the nucleotide sequence shown in SEQ ID NO:3, SEQ ID NO:5, SEQ ID NO:7 or SEQ ID NO:9 that it can bind with few or no mismatches to the nucleotide sequence shown in SEQ ID NO:3, SEQ ID NO:5, SEQ ID NO:7 or SEQ ID NO:9, thereby forming a stable duplex.

As used herein, the term "complementary" refers to Watson-Crick or Hoogsteen base pairing between nucleotide units of a nucleic acid molecule, and the term "bind" or "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

A nucleic acid molecule of the invention may include only a portion of the nucleic acid sequence of SEQ ID NO:3, SEQ ID NO:5, SEQ ID NO:7 or SEQ ID NO:9, e.g., a fragment that can be used as a probe or primer, or a fragment encoding a biologically active portion of XI. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 96%, 97%, 98%, or even 99% identity (with a preferred identity of 80–99%) over a nucleic acid or amino acid sequence of identical size or when compared to an aligned sequence in which the alignment is done by a computer homology program known in the art. Derivatives or analogs of the nucleic acids or proteins of the invention also include, but are not limited to, molecules comprising regions that are substantially homologous to the nucleic acids or proteins of the invention, in various embodiments, by at least about 70%, 80%, 85%, 90%, 95%, 96%, 97%, 98%, or even 99% identity (with a preferred identity of 80–99%) over a an amino acid sequence whose encoding nucleic acid is capable of hybridizing to the complement of a sequence encoding the aforementioned proteins under stringent, moderately stringent, or low stringent conditions.

"Homologous nucleic acid sequences" or "homologous amino acid sequences," or variations thereof, refer to sequences characterized by a homology at the nucleotide level or amino acid level as discussed above. Homologous nucleotide sequences encode those sequences coding for isoforms of an XI polypeptide. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions (see below) in SEQ ID NO:4, SEQ ID NO:6, SEQ ID NO:8, or SEQ ID NO:10, as well as a polypeptide having XI activity.

The nucleotide sequence determined from the cloning of the XI gene allows for the generation of probes and primers designed for use in identifying and/or cloning XI homologues in other cell types, e.g., from other tissues, as well as XI homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, or more consecutive sense strand nucleotide sequence of SEQ ID NO:3, SEQ ID NO:5, SEQ ID NO:7 or SEQ ID NO:9, or an anti-sense strand nucleotide sequence of SEQ ID NO:3, SEQ ID NO:5, SEQ ID NO:7 or SEQ ID NO:9, or of a naturally occurring mutant of SEQ ID NO:3, SEQ ID NO:5, SEQ ID NO:7 or SEQ ID NO:9.

Probes based on the XI nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells that misexpress an XI protein, such as by measuring a level of an XI-encoding nucleic acid in a sample of cells e.g., detecting XI mRNA levels or determining whether a genomic XI gene has been mutated or deleted.

A "polypeptide having a biologically active portion of XI" refers to polypeptides exhibiting activity similar, but not necessarily identical to, an activity of a polypeptide of the present invention, including mature forms, as measured in a particular biological assay, with or without dose dependency.

A nucleic acid fragment encoding a "biologically active portion of XI" can be prepared by isolating a portion of SEQ ID NO:3, SEQ ID NO:5, SEQ ID NO:7 or SEQ ID NO:9, that encodes a polypeptide having an XI biological activity (biological activities of the XI proteins are described below), expressing the encoded portion of XI protein (e.g., by recombinant expression in vitro) and assessing the activity of the encoded portion of XI.

XI Variants

The invention further encompasses nucleic acid molecules that differ from the nucleotide sequences shown in SEQ ID NO:3, SEQ ID NO:5, SEQ ID NO:7 or SEQ ID NO:9, due to the degeneracy of the genetic code. These nucleic acids thus encode the same XI protein as that encoded by the nucleotide sequence shown in SEQ ID NO:3, SEQ ID NO:5, SEQ ID NO:7 or SEQ ID NO:9, e.g., the polypeptide of SEQ ID NO:4, SEQ ID NO:6, SEQ ID NO:8, or SEQ ID NO:10, respectively.

In addition to the XI nucleotide sequence shown in SEQ ID NO:3, SEQ ID NO:5, SEQ ID NO:7 or SEQ ID NO:9, it will be appreciated by those skilled in the art that DNA sequence polymorphisms that lead to changes in the amino acid sequences of XI may exist within a population. As used herein, the terms "gene" and "recombinant gene" refer to nucleic acid molecules comprising an open reading frame encoding an XI protein, preferably a mammalian XI protein. Such natural allelic variations can typically result in 1–5% variance in the nucleotide sequence of the XI gene. Any and all such nucleotide variations and resulting amino acid polymorphisms in XI that are the result of natural allelic variation and that do not alter the functional activity of XI are intended to be within the scope of the invention.

Moreover, nucleic acid molecules encoding XI proteins from other species, and thus that have a nucleotide sequence that differs from the native sequence of SEQ ID NO:3, SEQ ID NO:5, SEQ ID NO:7 or SEQ ID NO:9, are intended to be within the scope of the invention. Nucleic acid molecules corresponding to natural allelic variants and homologues of the XI cDNAs of the invention can be isolated based on their homology to the XI nucleic acids disclosed herein using the cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:3, SEQ ID NO:5, SEQ ID NO:7 or SEQ ID NO:9. In another embodiment, the nucleic acid is at least 10, 25, 50, 100, or more nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least about 60% homologous to each other typically remain hybridized to each other.

Homologs (i.e., nucleic acids encoding XI proteins derived from other species) or other related sequences (e.g., paralogs) can be obtained by low, moderate or high stringency hybridization with all or a portion of the particular sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are occupied at equilibrium. Stringent conditions may also be achieved with the addition of destabilizing agents, such as formamide.

Stringent conditions are known to those skilled in the art. Preferably, the conditions are such that sequences at least about 65%, 70%, 75%, 85%, 90%, 95%, 96%, 97%, 98%, or 99% homologous to each other typically remain hybridized to each other. An isolated nucleic acid molecule of the invention that hybridizes under stringent conditions to the sequence of SEQ ID NO:3, SEQ ID NO:5, SEQ ID NO:7 or SEQ ID NO:9, corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:3, SEQ ID NO:5, SEQ ID NO:7 or SEQ ID NO:9, or fragments, analogs or derivatives thereof, under conditions of moderate stringency is provided.

In a third embodiment, a nucleic acid that is hybridizable to the nucleic acid molecule comprising the nucleotide sequence of SEQ ID NO:3, SEQ ID NO:5, SEQ ID NO:7 or SEQ ID NO:9, or fragments, analogs or derivatives thereof, under conditions of low stringency, is provided.

The present invention also relates to a DNA sequence, which is derived from a strain of *Thermotoga*. In the context of this invention this term also covers DNA sequences that are obtainable from a strain of *Thermotoga*, but which have been introduced into a different organism, from which a gene encoding the xylose isomerase may be obtained.

In a more preferred embodiment, the DNA sequence of the invention is derived from a strain of *Thermotoga maritima*, a strain of *Thermotoga elfii*, or a strain of *Thermotoga neapolitana*.

Conservative Mutations

In addition to naturally-occurring allelic variants of the XI sequence, the skilled artisan will further appreciate that changes can be introduced by mutation into the nucleotide sequence of SEQ ID NO:3, SEQ ID NO:5, SEQ ID NO:7 or SEQ ID NO:9, thereby leading to changes in the amino acid sequence of the encoded XI protein, without altering the functional ability of the XI protein. For example, nucleotide substitutions leading to amino acid substitutions at "non-essential" amino acid residues can be made in the sequence of SEQ ID NO:3, SEQ ID NO:5, SEQ ID NO:7 or SEQ ID NO:9. A "non-essential" amino acid residue is a residue that can be altered from the wild-type sequence of XI without altering the biological activity, whereas an "essential" amino acid residue is required for biological activity. For example, amino acid residues that are conserved among the XI proteins of the present invention, are predicted to be particularly unamenable to alteration.

Another aspect of the invention pertains to nucleic acid molecules encoding XI proteins that contain changes in amino acid residues that are not essential for activity. Such XI proteins differ in amino acid sequence from SEQ ID NO:4, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:4, SEQ ID NO:6, SEQ ID NO:8, or SEQ ID NO:10. Preferably, the protein encoded by the nucleic acid is at least about 80% homologous to SEQ ID NO:4, SEQ ID NO:6, SEQ ID NO:8, or SEQ ID NO:10, more preferably at least about 90%, 95%, 96%, 97%, 98%, and most preferably at least about 99% homologous to SEQ ID NO:4, SEQ ID NO:6, SEQ ID NO:8, or SEQ ID NO:10.

An isolated nucleic acid molecule encoding an XI protein homologous to the protein of SEQ ID NO:4, SEQ ID NO:6, SEQ ID NO:8, or SEQ ID NO:10 can be created by introducing one or more nucleotide substitutions, additions or deletions into the nucleotide sequence of SEQ ID NO:3, SEQ ID NO:5, SEQ ID NO:7 or SEQ ID NO:9, such that one or more amino acid substitutions, additions or deletions are introduced into the encoded protein.

Mutations can be introduced into the nucleotide sequence of SEQ ID NO:3, SEQ ID NO:5, SEQ ID NO:7 or SEQ ID NO:9 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in XI is replaced with another amino acid residue from the same side chain family. Alternatively, in another embodiment, mutations can be introduced randomly along all or part of an XI coding sequence, such as by saturation mutagenesis, and the resultant mutants can be screened for XI biological activity to identify mutants that retain activity. Following mutagenesis of SEQ ID NO:3, SEQ ID NO:5, SEQ ID NO:7 or SEQ ID NO:9 the encoded protein can be expressed by any recombinant technology known in the art and the activity of the protein can be determined.

In one embodiment, a mutant XI protein can be assayed for (1) the ability to form protein:protein interactions with other XI proteins, other cell-surface proteins, or biologically active portions thereof; (2) complex formation between a mutant XI protein and an XI receptor; (3) the ability of a mutant XI protein to bind to an intracellular target protein or biologically active portion thereof; (e.g., avidin proteins); (4) the ability to bind XI protein; or (5) the ability to specifically bind an anti-XI protein antibody.

Antisense XI Nucleic Acids

Another aspect of the invention pertains to isolated antisense nucleic acid molecules that are hybridizable to or complementary to the nucleic acid molecule comprising the nucleotide sequence of SEQ ID NO:3, SEQ ID NO:5, SEQ ID NO:7 or SEQ ID NO:9, or fragments, analogs or derivatives thereof An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, or more nucleotides or an entire XI coding strand, or to only a portion thereof. Nucleic acid molecules encoding fragments, homologs, derivatives and analogs of an XI protein of SEQ ID NO:4, SEQ ID NO:6, SEQ ID NO:8, or SEQ ID NO:10, or antisense nucleic acids complementary to an XI nucleic acid sequence of SEQ ID NO:3, SEQ ID NO:5, SEQ ID NO:7 or SEQ ID NO:9 are additionally provided.

In one embodiment, an antisense nucleic acid molecule is antisense to a "coding region" of the coding strand of a nucleotide sequence encoding XI. The term "coding region" refers to the region of the nucleotide sequence comprising codons which are translated into amino acid residues (e.g., the protein coding region of XI corresponds to SEQ ID NO:4, SEQ ID NO:6, SEQ ID NO:8, or SEQ ID NO:10). In another embodiment, the antisense nucleic acid molecule is antisense to a "noncoding region" of the coding strand of a nucleotide sequence encoding XI. The term "noncoding region" refers to 5' and 3' sequences that flank the coding region that are not translated into amino acids (i.e., also referred to as 5' and 3' untranslated regions).

Given the coding strand sequences encoding XI disclosed herein (e.g., SEQ ID NO:3, SEQ ID NO:5, SEQ ID NO:7 or SEQ ID NO:9), antisense nucleic acids of the invention can be designed according to the rules of Watson and Crick or Hoogsteen base pairing. The antisense nucleic acid molecule can be complementary to the entire coding region of XI mRNA, but more preferably is an oligonucleotide that is antisense to only a portion of the coding or noncoding region of XI mRNA. For example, the antisense oligonucleotide can be complementary to the region surrounding the translation start site of XI mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide or a chimeric RNA-DNA analogue.

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

Nucleic Acid Arrays

The present invention further provides nucleic acid detection kits, such as arrays or microarrays of nucleic acid molecules that are based on the sequence information provided in FIG. 1 (SEQ ID NOS:1). As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 4–60 nucleotides in length, more preferably 5–30 nucleotides in length, and most preferably about 10–25 nucleotides in length. For a certain type of microarray or detection kit, it may be preferable to use oligonucleotides that are only 4–18 nucleotides in length.

Using such arrays, the present invention provides methods to identify the expression of the XI proteins/peptides of the present invention. Such assays will typically involve arrays comprising many genes, at least one of which is a gene of the present invention and or alleles of the XI gene of the present invention.

XI Polypeptides

The present invention provides isolated peptide and protein molecules that consist of, consist essentially of, or comprise the amino acid sequences of the XI peptides disclosed in the FIG. 1, (encoded by the nucleic acid molecule shown in FIG. 1), as well as all obvious variants of these peptides that are within the art to make and use. Some of these variants are described in detail below.

An XI polypeptide of the invention includes the XI-like protein whose sequence is provided in SEQ ID NO:4, SEQ ID NO:6, SEQ ID NO:8, or SEQ ID NO:10. The invention also includes a mutant or variant protein any of whose residues may be changed from the corresponding residue shown in SEQ ID NO:4, SEQ ID NO:6, SEQ ID NO:8, or SEQ ID NO:10 while still encoding a protein that maintains its XI-like activities and physiological functions, or a functional fragment thereof. In some embodiments, up to 20% or more of the residues may be so changed in the mutant or variant protein. In some embodiments, the XI polypeptide according to the invention is a mature polypeptide.

One aspect of the invention pertains to isolated XI proteins, and biologically active portions thereof, or derivatives, fragments, analogs or homologs thereof. Also provided are polypeptide fragments suitable for use as immunogens to raise anti-XI antibodies. In one embodiment, native XI proteins can be isolated from cells or tissue sources by an appropriate purification scheme using standard protein purification techniques. In another embodiment, XI proteins are produced by recombinant DNA techniques. Alternative to recombinant expression, an XI protein or polypeptide can be synthesized chemically using standard peptide synthesis techniques.

"XI protein" or "XI polypeptide" refer to a protein or polypeptide encoded by the XI locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. "Native" proteins or polypeptides refer to proteins or polypeptides recovered from a source occurring in nature.

"Protein modifications or fragments" are provided by the present invention for XI polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art.

Besides substantially full-length polypeptides, the present invention provides for biologically active fragments of the polypeptides. Significant biological activities include ligand-binding, immunological activity and other biological activities characteristic of XI polypeptides. Immunological activities include both immunogenic function in a target immune system, as well as sharing of immunological epitopes for binding, serving as either a competitor or substitute antigen for an epitope of the XI protein. As used herein, "epitope" refers to an antigenic determinant of a polypeptide. An epitope could comprise three amino acids in a spatial conformation that is unique to the epitope. Generally, an epitope consists of at least five such amino acids, and more usually consists of at least 6–10 such amino acids. Methods of determining the spatial conformation of such amino acids are known in the art.

The present invention also provides for fusion polypeptides, comprising XI polypeptides and fragments. Homologous polypeptides may be fusions between two or more XI polypeptide sequences or between the sequences of XI and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor. Fusion proteins will typically be made by either recombinant nucleic acid methods or may be chemically synthesized.

A "purified" protein or biologically active portion thereof is substantially free of cellular material or other contaminating proteins from the cell or tissue source from which the XI protein is derived, or substantially free from chemical precursors or other chemicals when chemically synthesized. The language "substantially free of cellular material" includes preparations of XI protein in which the protein is separated from cellular components of the cells from which it is isolated or recombinantly produced. In one embodiment, the language "substantially free of cellular material" includes preparations of XI protein having less than about 30% (by dry weight) of non-XI protein (also referred to herein as a "contaminating protein"), more preferably less than about 20% of non-XI protein, still more preferably less than about 10% of non-XI protein, and most preferably less than about 5% non-XI protein. When the XI protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of XI protein in which the protein is separated from chemical precursors or other chemicals that are involved in the synthesis of the protein. In one embodiment, the language "substantially free of chemical precursors or other chemicals" includes preparations of XI protein having less than about 30% (by dry weight) of chemical precursors or non-XI chemicals, more preferably less than about 20% chemical precursors or non-XI chemicals, still more preferably less than about 10% chemical precursors or non-XI chemicals, and most preferably less than about 5% chemical precursors or non-XI chemicals.

Biologically active portions of an XI protein include peptides comprising amino acid sequences sufficiently homologous to or derived from the amino acid sequence of the XI protein, e.g., the amino acid sequence shown in SEQ ID NO:4, SEQ ID NO:6, SEQ ID NO:8, or SEQ ID NO:10 that include fewer amino acids than the full length XI proteins, and exhibit at least one activity of an XI protein. Typically, biologically active portions comprise a domain or motif with at least one activity of the XI protein. A biologically active portion of an XI protein can be a polypeptide that is, for example, 10, 25, 50, 100 or more amino acids in length.

A biologically active portion of an XI protein of the present invention may contain at least one of the above-identified domains conserved between the XI proteins. Moreover, other biologically active portions, in which other regions of the protein are deleted, can be prepared by recombinant techniques and evaluated for one or more of the functional activities of a native XI protein.

In an embodiment, the XI protein has an amino acid sequence shown in SEQ ID NO:4, SEQ ID NO:6, SEQ ID NO:8, or SEQ ID NO:10. In other embodiments, the XI protein is substantially homologous to SEQ ID NO:4, SEQ ID NO:6, SEQ ID NO:8, or SEQ ID NO:10 and retains the functional activity of the protein of SEQ ID NO:4, SEQ ID NO:6, SEQ ID NO:8, or SEQ ID NO:10, yet differs in amino acid sequence due to natural allelic variation or mutagenesis, as described in detail below. Accordingly, in another embodiment, the XI protein is a protein that comprises an amino acid sequence at least about 45% homologous to the amino acid sequence of SEQ ID NO:4, SEQ ID NO:6, SEQ ID NO:8, or SEQ ID NO:10 and retains the functional activity of the XI proteins of SEQ ID NO:4, SEQ ID NO:6, SEQ ID NO:8, or SEQ ID NO:10.

The isolated XI peptide can be purified from cells that naturally express it, purified from cells that have been altered to express it (recombinant), or synthesized using known protein synthesis methods. For example, a nucleic acid molecule encoding the XI peptide is cloned into an expression vector, the expression vector introduced into a host cell and the protein expressed in the host cell. The protein can then be isolated from the cells by an appropriate purification scheme using standard protein purification techniques. Accordingly, the present invention provides proteins that consist of the amino acid sequences provided in SEQ ID NO:4, SEQ ID NO:6, SEQ ID NO:8, or SEQ ID NO:10, for example, proteins encoded by the transcript/cDNA nucleic acid sequences shown in SEQ ID NO:3, SEQ ID NO:5, SEQ ID NO:7 or SEQ ID NO:9.

The present invention further provides proteins that consist essentially of the amino acid sequences provided in SEQ ID NO:4, SEQ ID NO:6, SEQ ID NO:8, or SEQ ID NO:10, for example, proteins encoded by the transcript/cDNA nucleic acid sequences shown in SEQ ID NO:3, SEQ ID NO:5, SEQ ID NO:7 or SEQ ID NO:9. A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in SEQ ID NO:4, SEQ ID NO:6, SEQ ID NO:8, or SEQ ID NO:10, for example, proteins encoded by the transcript/cDNA nucleic acid sequences shown in SEQ ID NO:3, SEQ ID NO:5, SEQ ID NO:7 or SEQ ID NO:9. A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the XI peptides of the present invention are the naturally occurring mature proteins.

The present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the XI peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The nucleic acid and protein sequences of the present invention can further be used as a "query sequence" to perform a search against sequence databases to, for example, identify other family members or related sequences. Full-length pre-processed forms, as well as mature processed forms, of proteins that comprise one of the peptides of the present invention can readily be identified as having complete sequence identity to one of the XI peptides of the present invention as well as being encoded by the same genetic locus as the XI peptide provided herein.

Paralogs of an XI peptide can readily be identified as having some degree of significant sequence homology/identity to at least a portion of the XI peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to an XI peptide encoding nucleic acid molecule under moderate to stringent conditions as more fully described below.

Orthologs of an XI peptide can readily be identified as having some degree of significant sequence homology/identity to at least a portion of the XI peptide as well as being encoded by a gene from another organism. Preferred orthologs will be isolated from mammals, preferably primates, for the development of therapeutic targets and agents. Such orthologs will be encoded by a nucleic acid sequence that will hybridize to an XI peptide encoding nucleic acid molecule under moderate to stringent conditions, as more fully described below, depending on the degree of relatedness of the two organisms yielding the proteins.

Variants of the XI peptides of the present invention can readily be generated using recombinant techniques. Such variants include, but are not limited to deletions, additions and substitutions in the amino acid sequence of the XI peptide. For example, one class of substitutions is conserved amino acid substitution. Such substitutions are those that substitute a given amino acid in an XI peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr.

The present invention further provides fragments of the XI peptides, in addition to proteins and peptides that comprise and consist of such fragments.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, are well known in the art.

Accordingly, the XI peptides of the present invention also encompass derivatives or analogs in which a substituted amino acid residue is not one encoded by the genetic code, in which a substituent group is included, in which the mature XI peptide is fused with another compound, such as a compound to increase the half-life of the XI peptide (for example, polyethylene glycol), or in which the additional amino acids are fused to the mature XI peptide, such as a leader or secretory sequence or a sequence for purification of the mature XI peptide or a pro-protein sequence.

Chimeric and Fusion Proteins

The invention also provides XI chimeric or fusion proteins. As used herein, an XI "chimeric protein" or "fusion protein" comprises an XI polypeptide operatively linked to a non-XI polypeptide. An "XI polypeptide" refers to a polypeptide having an amino acid sequence corresponding to XI, whereas a "non-XI polypeptide" refers to a polypeptide having an amino acid sequence corresponding to a protein that is not substantially similar to the XI protein, e.g., a protein that is different from the XI protein and that is derived from the same or a different organism. Within an XI fusion protein the XI polypeptide can correspond to all or a portion of an XI protein. In one embodiment, an XI fusion protein comprises at least one biologically active portion of an XI protein. In another embodiment, an XI fusion protein comprises at least two biologically active portions of an XI protein. Within the fusion protein, the term "operatively linked" is intended to indicate that the XI polypeptide and the non-XI polypeptide are fused in-frame to each other. The non-XI polypeptide can be fused to the N-terminus or C-terminus of the XI polypeptide.

For example, in one embodiment an XI fusion protein comprises an XI polypeptide operably linked to either an extracellular domain of a second protein, i.e., non-XI protein, or to the transmembrane and intracellular domain of a second protein, i.e., non-XI protein. Such fusion proteins can be further utilized in screening assays for compounds that modulate XI activity (such assays are described in detail below).

In another embodiment, the fusion protein is a GST-XI fusion protein in which the XI sequences are fused to the C-terminus of the GST (i.e., glutathione S-transferase) sequences. Such fusion proteins can facilitate the purification of recombinant XI.

In another embodiment, the fusion protein is an XI—immunoglobulin fusion protein in which the XI sequences comprising one or more domains are fused to sequences derived from a member of the immunoglobulin protein family.

An XI chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers.

XI Antibodies

Also included in the invention are antibodies to XI proteins, or fragments of XI proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab}$, and $F_{(ab)2}$ fragments, and an $F_{ab}$ expression library.

An isolated XI-related protein of the invention may be used as an antigen, or a portion or fragment thereof, and additionally can be used as an immunogen to generate antibodies that immunospecifically bind the antigen, using standard techniques for polyclonal and monoclonal antibody preparation. The full-length protein or mature portion (e.g. amino acids 2–444 of SEQ ID NO:4, SEQ ID NO:6, SEQ ID NO:8, or SEQ ID NO:10) can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:4, SEQ ID NO:6, SEQ ID NO:8, or SEQ ID NO:10, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

A protein of the invention, or a derivative, fragment, analog, homolog or ortholog thereof, may be utilized as an immunogen in the generation of antibodies that immunospecifically bind these protein components. Various procedures known within the art may be used for the production of polyclonal or monoclonal antibodies directed against a protein of the invention, or against derivatives, fragments, analogs homologs or orthologs thereof.

XI Recombinant Expression Vectors and Host Cells

Another aspect of the invention pertains to vectors, preferably expression vectors, containing a nucleic acid encoding an XI protein, or derivatives, fragments, analogs or homologs thereof. As used herein, the term "vector" refers to a nucleic acid molecule capable of transporting another nucleic acid to which it has been linked. With this aspect of the invention, the vector includes a plasmid, single or double stranded phage, a single or double stranded RNA or DNA viral vector, or artificial chromosome, such as a BAC, PAC, YAC, or MAC. The invention provides vectors for the maintenance (cloning vectors) or vectors for expression (expression vectors) of the nucleic acid molecules. The vectors can function in prokaryotic or eukaryotic cells or in both (shuttle vectors).

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., XI proteins, mutant forms of XI proteins, fusion proteins, etc.).

The regulatory sequences to which the nucleic acid molecules described herein can be operably linked include promoters for directing mRNA transcription. Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda PR or PL promoters or the *E. coli* lac, trp or tac promoters.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

The recombinant expression vectors of the invention can be designed for expression of XI proteins in prokaryotic or eukaryotic cells. Alternatively, the recombinant expression vector can be transcribed and translated in vitro, for example using T7 promoter regulatory sequences and T7 polymerase.

In another embodiment, the XI expression vector is a yeast expression vector. Examples of vectors for expression in yeast *Saccharomyces cerivisae* include pYepSec1, pMFa, pJRY88, pYES2, and picZ.

In yet another embodiment, a nucleic acid of the invention is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus, and simian virus 40.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to XI mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, XI protein can be expressed in bacterial cells such as *E. coli*, insect cells, yeast or mammalian cells (such as human, Chinese hamster ovary cells (CHO) or COS cells). Other suitable host cells are known to those skilled in the art. Vector DNA can be introduced into prokaryotic or eukaryotic cells via conventional transformation or transfection techniques.

A host cell of the invention, such as a prokaryotic or eukaryotic host cell in culture, can be used to produce (i.e., express) XI protein. Accordingly, the invention further provides methods for producing XI protein using the host cells of the invention. In one embodiment, the method comprises culturing the host cell of invention (into which a recombinant expression vector encoding XI protein has been introduced) in a suitable medium such that XI protein is produced. In another embodiment, the method further comprises isolating XI protein from the medium or the host cell.

The host cell into which the DNA construct or the recombinant vector of the invention is introduced may be any cell that is capable of producing the present enzyme and includes bacteria, yeast, fungi and higher eukaryotic cells.

Examples of bacterial host cells which, on cultivation, are capable of producing the enzyme of the invention include gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, and gram-negative bacteria such as *Escherichia coli*. The transformation of the bacteria may be effected by protoplast transformation, electroporation, conjugation, or by using competent cells in a manner known per se.

When expressing the enzyme in a bacteria such as *E. coli*, the enzyme may be retained in the cytoplasm, typically as insoluble granules (known as inclusion bodies), or it may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacteria such as a strain of *Bacillus* or a strain of *Streptomyces*, the enzyme may be retained in the cytoplasm, or it may be directed to the extracellular medium by a bacterial secretion sequence. In the latter case, the enzyme may be recovered from the medium by conventional isolation techniques, as also described below.

Examples of bacterial host cells that on cultivation are capable of producing the enzyme of the invention include fungal host cells such as yeast's and filamentous fungi. In particular, the host cell may be a strain of *Trichoderma*, in particular a strain of *Trichoderma harzianum* or *Trichoderma reesei*, a strain of *Aspergillus*, in particular a strain of *Aspergillus oryzae* or *Aspergillus niger*.

Fungal cells may be transformed by a process involving protoplast formation and transformation of the protoplasts followed by regeneration of the cell wall in a manner known per se.

The host cell may also be a yeast cell, preferably a strain of Saccharomyces, in particular *Saccharomyces cerevisiae, Saccharomyces kluyveri* or *Saccharomyces uvarum*, a strain of *Schizosaccharomyces sp.*, in particular *Schizosaccharomyces pombe*, a strain of *Hansenula sp.*, a strain of *Pichia sp.*, a strain of *Yarrowia sp.*, in particular *Yarrowia lipolytica*, or a strain of *Kluyveromyces sp.*, in particular *Kluyveromyces lactis*.

Methods of Producing Xylose Isomerase

In another aspect, the present invention provides a method of producing an isolated or purified xylose isomerase.

As defined herein, an isolated or purified xylose isomerase is a xylose isomerase preparation essentially free of other non-xylose isomerase polypeptides, e.g., at least about 60% pure, preferably about 80% pure, more preferred about 90% pure, and most preferred about 95% pure, as determined by SDS-PAGE.

According to one embodiment of the invention, a suitable host cell, which has been transformed with a DNA sequence encoding the enzyme, is cultured under conditions permitting the production of the enzyme, and the resulting enzyme is recovered from the culture by extracting from the cells.

When an expression vector comprising the DNA sequence of the invention is transformed into a heterologous host cell, it is possible to enable heterologous recombinant production of the enzyme of the invention. This makes possible to obtain a highly purified xylose isomerase enzyme composition, characterized by being free from homologous impurities.

As defined herein, homologous impurities covers impurities, in particular polypeptides, originating from the homologous cell from which the DNA sequence of the invention was originally derived.

In the present invention the homologous cell may e.g. be a strain of *Thermotoga maritima*, a strain of *Thermotoga elfii* or a strain of *Thermotoga neapolitana*.

The medium used to culture the transformed host cells may be any conventional medium suitable for growing the host cells in question. The expressed xylose isomerase may extracted from the cells and may be recovered therefrom by well-known procedures including separating the cells from the medium by centrifugation or filtration, breaking cells (releasing cell contents) by means of French Press, precipitating proteinaceous components of the medium by means of a salt such as ammonium sulfate, followed by chromatographic procedures such as ion exchange chromatography, affinity chromatography, or the like.

INDUSTRIAL APPLICATIONS

The xylose isomerase obtained by the method of the invention may find application in industrial processes conventionally involving the action of isomerization enzymes, in particular glucose isomerization processes.

By employing the enzyme of the invention in a one-step glucose isomerization process, the reaction temperature is generally in the range of from about 45 to about 130° C. Preferably, the temperature is at least about 50° C., more preferably at least about 55° C. and most preferably at least about 60° C. Preferably, the temperature is at most about 100° C., more preferably at most about 90° C. and most preferably at most about 80° C. In the most preferred embodiment, the reaction temperature is maintained in the range of from about 60 to about 80° C.

In another preferred embodiment, the xylose isomerase may be applied in a two step glucose isomerization process. In this process, the first step of the isomerization is carried out as a conventional isomerization process, employing either a conventional isomerization enzyme or the xylose isomerase of the invention, to produce a high fructose syrup containing from about 40 to 50% fructose. In the second step, the end product from the first step is subjected to isomerization at elevated temperatures, i.e., from 45 to 130° C., and at a pH of from about 3.5 to about 8, by employing the xylose isomerase of the invention, to produce a high fructose syrup containing from about 50 to 60% fructose. In the most preferred embodiment, the reaction temperature is maintained in the range of from about 60 to about 80° C. at a pH of from about 5.2 to about 7.

Other isomerization conditions can be as for conventional isomerization processes. The reaction time can be in the range of 10 seconds to 5 hours, depending on the isomerization temperature, specific activity of the enzyme preparation employed, etc. The isomerization pH affects enzyme activity, stability and by-product formation. The isomerization pH should be in the range of from 3.5 to 8. Preferably, the pH is at least about 4.5 more preferably at least about 5.0 and most preferably at least about 5.2. Preferably, the pH is at most about 9.0, more preferably at most about 8.0 and most preferably at most about 7.0. By-product formation due to glucose and fructose decomposition increases at higher pH levels.

The feed syrup dry substance content (DS) influences the rate of fructose formation. Too high a DS level results in lower apparent enzyme activity. On the other hand, too dilute a syrup will lead to a lower optimum substrate/enzyme ratio and increased risk of microbial infection. The feed liquor should contain from 20 to 65% w/w dry substance glucose. Preferably, the w/w dry substance glucose is at least about 25%, more preferably at least about 30%, and most preferably at least about 35%. Preferably, the w/w dry substance glucose is at most about 60%, more preferably at most about 55%, and most preferably at most about 50%. In the most preferred embodiment, the feed liquor should contain from about 35 to about 50% w/w dry substance glucose.

The concentration of monosaccharides in the feed syrup should be as high as possible in order to obtain the maximum isomerization rate. With a low monosaccharide concentration in the feed syrup the isomerization temperature must be elevated in order to attain a given fructose concentration.

For optimal performance of the isomerization process, the xylose isomerase of the invention can be immobilized. The isomerization process of the invention can then be carried out as a continuous, fixed-bed reactor process. In addition to the convenience of continuous operation, the fixed-bed process permits a short reaction time thereby minimizing by-product formation. The enzyme can be immobilized by methods known in the art to produce xylose isomerase preparations with acceptable high unit activities.

In another preferred embodiment, the xylose isomerase is used in the presence of a bivalent cation such as $Mg^{2+}$, $Co^{2+}$, $Mn^{2+}$ or a combination of these cations.

The invention will be further illustrated in the following non-limiting examples.

EXAMPLES

The invention is further illustrated in the following examples, which are not intended to be in any way limiting to the scope of the invention as claimed.

Examples 1 to 4

Experimental

For the present invention, error-prone PCR using the Taq DNA polymerase is used to create a library of plasmids containing a mutated TNXI Val186Thr gene. The resulting mutated plasmids are transformed into *E. coli* HB101(DE3) cells (XI deficient strain) which are created using a λDE3 lysogenation kit (Novagen), and then plated on LB agar containing Ampicillin. A typical screening procedure involves the following steps:

---

Pick single transformant colonies into 24 well plates containing about 2 ml LB + Amp in each well
⇓
Incubate overnight at about 37° C. on a shaker at about 175 rpm
⇓
Spin down cell pellets at about 2000 rpm for approximately 10 min.; discard supernatant
⇓
Re-suspend cell pellets in about 200 µl of buffer A (MOPS + Co + Mg)
⇓

-continued

Add approximately 40 µL 1% lysozyme and incubate at about 37° C. for approximately 1 hour.
⇓
Apply at least 3 cycles of freeze/thaw treatment to break cells
⇓
Collect supernatants by centrifugation at about 2000 rpm for about 10 min.
⇓
Screen for activity at pH of about 5.2 (at about 80° C.) and pH of about 7 (at about 60° C.)

---

After the first round of error-prone PCR, screening 1,000 transformant clones (in 96 well plates and confirmed assay in bigger volume) yielded 11 clones that are at least 30% more active than TNXI Val186Thr in both conditions (pH about 5.2 at about 80° C. and pH about 7 at about 60° C.). They are designated as 1B2, 3A2, 6G6, 6H12, 8A5, 8D1, 8G1, 8H1, 10F6 10H2, 10H5 (The first number is the plate number, the letter and second number are position of the well on the plate).

Of these clones, 3A2 and 6H12 are the most active transformants with approximately 80% more activity in both conditions. If 3A2 or 6H12 is used as a template to parent the next round of error prone PCR and the remaining 11 clones are discarded, this might also result in discarding the positive mutations by those clones. So, instead of wasting these clones, a DNA shuffling technique is applied to these genes to select the one positive clone that results from a combination of positive mutations to the parent in the next round of error prone PCR. These genes are subjected to DNA shuffling and a general procedure for such a technique follows:

---

Amplify genes using PCR with primers flanking NdeI and HindIII sites
⇓
Run the PCR products on agarose gel, cut them out, and gene cleaned
⇓
Digest all genes with DNaseI at about 15° C. for approximately 2 min. to generate about
50 base pair fragments
⇓
Reassemble fragments without primers using Pfu DNA polymerase
⇓
Amplify reassembled genes by PCR using primers
⇓
Obtain a single band at correct size on agarose gel; cut and gene cleaned
⇓
Clone into plasmids and transformed into *E. coli* HB101(DE3)
⇓
Screen for mutants with improved activity in both conditions

---

After screening 1,000 clones of shuffling mutants, 2 clones (S1H12 and S1E10) were found to have much more activity at both pH of about 5.2 (80° C.) and pH of about 7 (60° C.) than 3A2 and 6H12. Based on crude extract assay starting from 5 ml culture, S1H12 is 94% and 88% more active than 3A2 at pH of about 5.2 (80° C.) and pH 7 of about (60° C.), respectively. S1E10 is 96% and 80% more active at about pH 5.2 (80° C.) and about pH 7 (60° C.), respectively. But when pure enzymes are analyzed, the specific activity of these two shuffled clones is not as high as that of TNXI 3A2.

Genes encoding these 2 shuffled clones, S1H12 and S1E10, were mixed together equally to parent the second round of error prone PCR. A few clones looked to be more active than S1E10, but confirmation assays in both crude extracts from 5 ml and 100 ml cultures revealed that these clones are, in fact, clones with intermediate activity between S1H12 and S1E10.

Optimum temperature and pH curves have been done on purified enzymes of 2 first round random mutants (3A2 and 6H12), 2 shuffled clones (S1H12 and S1E10), wild-type TNXI, and TNXI V186T. The curves are shown in FIGS. 1 and 2.

The results are summarized below:

The specific activity of the TNXI 3A2 (V186T/L283P) at 2 screening conditions, pH of about 5.2 (at about 80° C.) and pH of about 7.0 (at about 60° C.), is between 3.7–5.5 fold higher than the parental TNXI V186T.

With 3.7 and 5.5 fold increases in activity on glucose at a pH of about 5.2 (at about 80° C.) and a pH of about 7 (at about 60° C.), respectively, compared to TNXI V186T, mutant 3A2 is the best mutant enzyme obtained during the first round of error-prone PCR.

TNXI 3A2 at about 60° C. is 51% as active as TNXI V186T is at its optimum temperature (about 95° C.). It is also 67% as active at a pH of about 5.2 as TNXI V186T is at its optimum pH (about 7.0).

DNA sequencing to determine what changes occur to these mutations has also been completed. The resulting amino acid substitutions found are as follows:

| 3A2: | Leu283→Pro (preferred clone) |
|------|------------------------------|
| 6H12: | Tyr165→Asp |
| S1H12: | Tyr165→Asp and Leu283→Pro |
| S1E10: | Tyr165→Asp; Tyr251→Cys; Leu283→Pro; and Arg287→Met |

Structural Analysis of Mutation Sites

The four mutations found in the S1E10 shuffled mutant are not in the active site of TNXI. In fact, they are located in α-helical structures surrounding the β-barrel active site with their side-chains pointing outward (see FIG. 3). Not being bound by theory, below are some observations and speculation for each mutation:

1) L283P (Leu283→Pro) (preferred clone)
   This residue is located at the surface of a monomer and at the interface of subunit B and D (or A and C) dimer.
   Whenever Pro occurs in a peptide chain, it interrupts the α-helix and creates a kink or bend. (Lehninger, 1970)
   Neither Leu nor Pro side-chain can form H-bond with neighboring residues. Such a substitution would result in a change in local structure due to bending of the α-helix.
   If such is not the case, the substitution would then result in less bulk (since the Leu side-chain is bigger than the Pro) in local region and create more space for movement during catalysis.
2) Y165D (Tyr165→Asp)
   This residue is located at the surface of a monomer and at the interface of subunits B and D (or A and C) dimer.
   Tyr165 side-chain OH group forms H-bonds (<3 Å apart) with Glu108 and Arg 149 side-chains.
   Substitution of Tyr with Asp residue results in disruption of H-bond patterns (and might also create more space) that would make the region more flexible.
   The Asp residue side-chain is negatively charged at pH>3.86 but it appears that no other neighboring residues are close enough to interact with it.
3) Y251C (Tyr251→Cys)
   This residue is located at the surface of a monomer and at the interface of subunit B and D (or A and C) dimer.
   The Tyr251 side-chain —OH group does not appear to form H-bonds with other residues.
   Substitution of Tyr with a Cys residue does not disrupt any local interaction.
   There are differences between sizes of the side-chains. The Cys side-chain is smaller than the Tyr side chain. Thus the substitution creates more space for the enzyme at the interface, which may facilitate movement during catalysis.
4) R287M (Arg287→Met)
   This residue is located at the surface of a monomer and at the interface of subunit B and D (or A and C) dimer.
   The Arg287 side-chain NH1 group forms a H-bond with the Glu324 side-chain OE1 group.
   Substitution of Arg with Met results in disruption of this H-bond and, since Met side-chain is smaller than Arg side-chain, it also creates space in the region.
   The effect of this mutation would be quite similar to that of Y 165D mentioned above.

Example 5

The *Thermotoga neapolitana* xylose isomerase (TNXI) is extremely thermostable and highly active at 95° C. and above. Its mutant derivative, TNXI V185T, was the most active type II XI previously reported, with a catalytic efficiency ($k_{cat}/K_M$) of 25.1 $S^{-1}$ $mM^{-1}$ toward glucose at 80° C. (pH 7.0). To further optimize this enzyme's potential industrial utility, two rounds of random mutagenesis and low temperature/low pH activity screening were performed using the TNXI V185T-encoding gene as the template. Mutants TNXI 3A2 (V185T/L282P) and 1F1 (V185T/L282P/F186S) (FIG. 19 SEQ ID NO:11; and DNA SEQ ID NO:12 FIG. 20) were obtained after rounds one and two of random mutagenesis, respectively. TNXI 1F1 was more active than 3A2, which in turn was more active than TNXI V185T at all temperatures and pHs tested. TNXI 3A2 and 1F1 high activities at low temperatures were due to significantly lower activation energies (57 and 44 kJ/mole, respectively) than that of TNXI and V185T (87 kJ/mole). Although 3A2 was more active than TNXI and V185T, its kinetic stability (based on the enzymes' half lives in different incubation conditions) was inferior to those of TNXI V185T possibly due to unfavorable van der Waal contacts of Pro282's pyrrolidine ring with neighboring mainchain atoms. This would in turn lead to conformational changes and eventually destabilize the enzyme. Unlike TNXI 3A2, 1F1 is more kinetically stable than TNXI and TNXI V185T. 1F1's enhanced stability is thought to be a result of additional H-bond formation between Ser186's sidechain and the neighboring L229 residue's mainchain structure. This, in turn, strengthens local conformation and the affinity of E231 co-ordination with the structural metal, hence restoring the thermostability lost in 3A2. We showed here that low temperature/low pH activity of a hyperthermostable enzyme could be enhanced without costs to extreme stability by directed enzyme evolution.

Xylose isomerase (XI) (EC.5.3.1.5) is an intracellular enzyme found in bacteria that can utilize xylose as a carbon substrate for growth (Chen, 1980). Due to its ability to use glucose as substrate and convert it to fructose, XI is often referred to as glucose isomerase, and it is widely used in the industrial production of high fructose corn syrup (HFCS) (Meng et al., 1993; Bhosale et al., 1996). XI is one of the three highest tonnage value enzymes, amylase and protease being the other two (Bhosale et al., 1996). Most industrially used XIs are isolated from mesophilic organisms (e.g., *Streptomyces* spp. and *Actinoplanes* spp.). The reaction temperature used in the current industrial glucose isomerization process is limited to 60° C. because of by-product and color formations that occur at high temperature and alkaline pH, and because the isomerases themselves are not highly thermostable (Lee and Zeikus, 1991; Vieille and Zeikus, 2000). Thermostable XIs with neutral or slightly acidic pH optima have a potential for industrial applications. Such enzymes would allow for faster reaction rates, higher fructose concentrations at equilibrium, higher process stability, decreased viscosity of substrate and product streams, and reduced by-products formation (Lee and Zeikus, 1991; Vieille and Zeikus, 2000).

The XI from the hyperthermophile *Thermotoga neapolitana* (TNXI) has been studied extensively in our laboratory. The gene encoding TNXI (xylA) was cloned, sequenced, and overexpressed in *Escherichia coli* (Vieille et al., 1995). TNXI's active site was engineered by site-directed mutagenesis to increase its activity on glucose (Sriprapundh et al., 2000). The TNXI Val185Thr (V185T) mutant derivative is more active, more glucose-efficient, and as stable as the wild-type TNXI. It is also the most active type II XI ever reported. Although TNXI V185T is highly thermostable and highly active at 97° C., it is very poorly active (10% of maximal activity) at the current industrial isomerization temperature (60° C.) and it requires a neutral pH for optimal activity.

Rules for engineering protein activity and stability by rational design are likely to be protein-specific, and any such design effort would require prior detailed structural information. Numerous and intensive site-directed mutagenesis studies have probed this issue. Despite these efforts, considerable disagreement remains over which forces dominate stabilization mechanisms, and no generally applicable rules have been established (Giver et al., 1998; Vieille and Zeikus, 2001). Although protein chemists continue to elucidate the relationships between the sequence, structure, and function of proteins, the extensive knowledge that is necessary for the application of rational engineering approaches is available for only a tiny fraction of known enzymes. Directed evolution, on the other hand, has proved to be useful for modifying enzymes in the absence of such knowledge (Kuchner and Arnold, 1997). In directed evolution, the process of natural evolution is accelerated in a test tube for selecting proteins with the desired properties (Moore and Maranas, 2000). A typical experimental cycle of directed evolution begins with the creation of a library of mutated genes. Among the methods that introduce mutations randomly along the entire length of a gene (Leung et al., 1989, Stemmer, 1994, Zhao and Arnold, 1997, Shao et al., 1998, Zhao et al., 1998, and Ostermeier et al., 1999), error-prone PCR has been used the most extensively. The mutated genes are then ligated into an expression vector and transformed into suitable bacterial cells. A screening procedure is next employed to identify the few transformants expressing proteins/enzymes with improved properties. Random mutagenesis and screening are repeated several times depending on the extent to which the properties of the protein should be altered and on the effects of mutations observed in each generation. Interest in engineering enzymes using directed evolution has grown significantly in the past few years. It has been used to increase enzyme thermostability, activity on novel substrates, substrate specificity, and enantioselectivity. For example, six generations of random mutagenesis, recombination, and screening stabilized *Bacillus subtilis* p-nitrobenzyl esterase significantly (>14° C. increase in $T_m$) without compromising its catalytic activity at lower temperature (Giver et al., 1998).

Here we use the TNXI V185T-encoding gene as the template for directed evolution to develop an enzyme active at 60° C. and acidic pH. We show that activity can be increased significantly at low temperature and acidic pH without cost to the enzyme thermal stability.

Materials and Methods

Random mutagenesis: Random mutations were introduced into the TNXI V185T-encoding gene cloned between the NdeI and HindIII restriction sites of pET23a(+). PCR was performed with primers 5'-CGACTCACTATAGG-GAGAC-3' and 5'-GGTGGTGCTCGAGTGCG-3' encoding sequences upstream of the NdeI site and downstream of the HindIII, respectively, in pET23a(+). The reaction mixture contained 100 ng plasmid DNA, 50 pmol of each primer, 50 mM KCl, 10 mM Tris-HCl (pH 8.3), 1.5 mM MgCl$_2$, 0.4 mM dCTP, 0.4 mM dTTP, 0.08 mM dATP, 0.08 mM dGTP, and 2.5 Units Taq DNA polymerase (Roche, Nutley, N.J.) in a 50 μl reaction volume. Cycling parameters were 36 cycles of 95° C. for 45 see, 50° C. for 45 sec, and 72° C. for 3 min. Amplification of the 1.4-kb product was checked by running a small aliquot of the reaction on a 1% agarose gel. The PCR product was purified using the Geneclean III kit (Bio101, Carlsbad, Calif.) and cloned back into the NdeI and HindIII sites of pET23a(+) using standard molecular biological techniques (Ausubel et al, 1993). For the second round of random mutagenesis, the gene encoding TNXI 3A2 was used as the template.

Construction of a mutant library: The plasmids resulting from random mutagenesis were transformed into electrocompetent *E. coli* HB101(DE3) cells (XI-deficient) created using the λDE3 lysogenation kit (Novagen, Madison, Wis.). Transformants were plated on Luria-Bertani (LB) agar containing 100 μg/ml ampicillin. After 16 hr of growth, single colonies were picked with sterile toothpicks and transferred into 24-well plates, each well containing 2 ml of LB plus 100 μg/ml ampicillin. Plates were then incubated overnight at 37° C. on a shaker at 175 rpm to allow for cell growth. One hundred fifty microliters of each culture were transferred to sterile 96-well plates. These plates were used to quantify bacterial growth by reading the bacterial suspensions' $OD_{595}$ in a microplate reader (Dynatech, McLean, Va.), before being stored at 4° C. to save the original cultures. The rest of the cultures was pelleted by centrifugation at 1,000 g for 10 min and resuspended in 200 μl of 50 mM MOPS (pH 7.0) containing mM MgSO$_4$ and 0.5 mM CoCl$_2$ (i.e., buffer A). Bacterial suspensions were incubated with 50 μl of a 1% lysozyme solution at 37° C. for 1 hr before being subjected to 3 freeze/thaw cycles (5 min in a dry ice-ethanol bath and 5 min in a 50° C. water bath) to break the cells and release the enzymes into the supernatant. Cell-free crude extracts were then obtained by centrifugation at 1,000 g for 10 min and stored at 4° C. for further use.

Screening the mutant library for increased activity on glucose at 60° C. and low pH: The crude extracts were assayed for glucose isomerization in two conditions: 60° C. (pH 7.0) and 80° C. (pH 5.2). Assays were performed in microtiter plates with 150 μl of 100 mM MOPS (pH 7.0) or 100 mM sodium acetate (pH 5.2) containing 1 mM CoCl$_2$, 0.4 mM glucose, and 10 μl of crude extract. The plates were incubated at 60° C. (pH 7.0) or 80° C. (pH 5.2) for 10 min and placed on ice to stop the reactions. The fructose produced was assayed using the resorcinol-ferric ammonium sulfate-hydrochloric acid method (Schenk and Bisswanger, 1998). Ten microliters of each reaction were transferred to a new set of microtiter plates and mixed with 40 µl of distilled water and 150 µl of a freshly prepared 1:1 mixture (v/v) of solution A (0.05% resorcinol in ethanol) and solution B (0.216 g of $FeNH_4(SO_4)_2 \cdot 12H_2O$ in 1L HCl). The plates were incubated in an 80° C. water bath for 30 min to develop the color. The $OD_{490}$ was measured with a microplate reader (Dynatech) with 0–2.5 mM fructose as standards. A crude extract of HB101(DE3)pET23a(+) was used as the negative control on each plate. Crude extracts of HB101(DE3) expressing TNXI V185T and TNXI 3A2 were the positive controls in mutagenesis rounds one and two, respectively. Mutants with potentially higher activity on glucose than the positive control were selected on the basis of increases in both $OD_{490}$ and $OD_{490}/OD_{595}$ relative to the positive controls in the two rounds of mutagenesis. Mutants showing increased activity were screened a second time using crude extracts prepared from 5 ml cultures. These crude extracts were prepared as described above, before being heat-treated at 80° C. for 15 min and centrifuged.

Oligonucleotide synthesis and DNA sequencing: PCR primers were synthesized by the Macromolecular Structure Facility, Department of Biochemistry and Molecular Biology at MSU. DNA sequences were determined either manually using the Thermosequenase kit (USB, Cleveland, Ohio) or automatically at the MSU Genomics Technology Support Facility.

Protein Purification: Recombinant enzymes were purified as described (Vieille et al., 1995), followed by an additional ion-exchange chromatography step. Partially purified enzymes were applied to. a Q-Sepharose column (2.5×15 cm) equilibrated with buffer A, and enzymes were eluted using a 500 ml linear 0–300 mM NaCl gradient in buffer A. The pooled fractions from the Q-Sepharose column were concentrated in a stirred ultrafiltration cell (30 kDa MW cut-off) (Amicon, Beverly, Mass.) and dialyzed twice against buffer A. Concentrated, homogenous enzymes were dispensed and stored frozen at −70° C.

Glucose isomerase assays: TNXI and its mutants were assayed routinely with glucose as the substrate. The enzyme (1–1.5 mg/ml) was incubated in 100 mM MOPS (pH 7.0) [or 100 mM sodium acetate (pH 5.5)] containing 1 mM $CoCl_2$ and 0.4 M glucose at 80° C. for 10 min. The reaction was stopped by transferring the tube to an ice bath. The amount of fructose produced was determined by the resorcinol-ferric ammonium sulfate-hydrochloric acid method (Schenk and Bisswanger, 1998). To determine the effect of temperature on activity, the enzymes were incubated in the reaction mixture at the temperatures of interest in a heated water (45–95° C.) or oil bath (95–110° C.) for 10 min. The effect of pH on activity was determined using the routine assay described above except that the MOPS buffer was substituted with 100 mM sodium acetate (pH 4.3–5.8), 100 mM PIPES (pH 6.1–7.0), or 100 mM EPPS (pH 7.2–8.1). All pHs were adjusted at room temperature, and the $\Delta pKa/\Delta t$'s for acetate, PIPES, and EPPS (0,−0.0085, and −0.011, respectively) (USB, Cleveland, Ohio) were taken into account for the results. To determine the kinetic parameters, assays were performed in 50 mM MOPS (pH 7.0) containing 10–1,500 mM glucose and 1 mM $CoCl_2$. One unit of glucose isomerase activity is defined as the amount of enzyme that produces 1 µmol of fructose per minute under the assay conditions.

Thermal inactivation assays: To obtain the apo-enzymes (metal-free enzymes), the purified enzymes were incubated overnight at 4° C. in 50 mM MOPS (pH 7.0) containing 10 mM EDTA. They were then dialyzed twice against 50 mM MOPS (pH 7.0) containing 2 mM EDTA, and they were finally dialyzed twice against 50 mM MOPS (pH 7.0) without EDTA. $CoCl_2$ (0.5 mM) was added to the apo-enzymes and equilibrated at 4° C. overnight before thermoinactivation assays. The time course of irreversible thermoinactivation was measured by incubating the enzymes (0.1–0.2 mg/ml) in either 10 mM MOPS (pH 7.0) or 10 mM sodium acetate (pH 5.5) at various temperatures for different periods of time in a heated water bath. Residual glucose isomerase activity was measured at 80° C. as described above. The first order rate constant, k, of irreversible thermoinactivation was obtained by linear regression in semi-log coordinates. Enzyme half-lives were calculated from the equation: $t_{(1/2)} = \ln 2/k$.

Differential Scanning Calorimetry (DSC): DSC experiments were performed on a Nanocal differential scanning calorimeter (Calorimetry Sciences Corp., Provo, Utah) using a scan rate of 1° C./min. Samples were scanned from 25° C. to 100° C. The apo-enzymes were scanned against 50 mM MOPS (pH 7.0). Enzymes containing both $Mg^{2+}$ and $Co^{2+}$ were dialyzed against buffer A, then scanned against the dialysis buffer as control.

Analysis of three-dimensional (3D) structures of TNXI and its variants: Enzymes were visualized on an IRIS-4D25 computer (Silicon Graphics Computer System, Mountain View, Calif.) using the INSIGHT II graphic program (Biosym Technologies, San Diego, Calif.). The TNXI pdb file (#1A0E) was obtained from the Protein Data Bank (www.rcsb.org/pdb).

Results

Construction of mutant TNXI libraries and screening for activity on glucose at low temperature and low pH: TNXI V185T is optimally active at 95° C. –97° C., but its activity at 60° C. does not exceed 10% of its optimal activity (Sriprapundh et al., 2000). It retains only 20% of its optimal activity at pH 5.2. To increase this enzyme's activity at 60° C. and at acidic pH, and to gain insight into the factors determining the effects of temperature and pH on activity, we subjected the TNXI V185T-encoding gene to sequential random mutagenesis and to low temperature/low pH activity screening. Random mutations were introduced into the gene by error-prone PCR. The PCR conditions used were suggested to yield an average of 1–2 mutations per gene, conditions deemed optimal for the improvement of specific properties by mutagenesis and screening (Arnold and Moore, 1997). After the first round of random mutagenesis, 1,000 transformants were screened for their activity on glucose at low temperature (60° C., pH 7.0) and at low pH (pH 5.2, 80° C.). Thirty mutants were identified that showed significantly higher activity (>30% increase) than TNXI V185T in both screening conditions. The phenotype of these mutants was tested again with heat-treated crude extracts prepared from 5 ml cultures. Higher activity on glucose was confirmed in only eleven out of the thirty crude extracts. XI expression level in these eleven crude extracts was checked by SDS-PAGE. Ten crude extracts showed higher XI content than the TNXI V185T control (data not shown). These ten mutants were discarded. The remaining mutant, TNXI 3A2, was purified to homogeneity. Once it was verified that TNXI 3A2 was significantly more active than TNXI V185T at 60° C. and at pH 5.2, the gene encoding TNXI 3A2 was used as the template in a second round of error-prone PCR and activity screening at low temperature and low pH. A library of ~1,500 transformants was screened using TNXI 3A2 as the positive control. A single mutant, TNXI 1F1, showed 80% and 40% increases in activity on glucose at 80° C. (pH 5.2) and 60° C. (pH 7.0), respectively, based on assays with heat-treated crude extracts. TNXI 3A2 and 1F1 were then purified to homogeneity. Their catalytic properties were studied in function of temperature and pH, and their thermostability was determined.

Effects of temperature and pH on TNXI 3A2 and 1F1 activities: The effect of temperature on 3A2 and 1F1 glucose isomerase activities is shown in FIG. 1A in comparison to the activities of TNXI and TNXI V185T. Both 3A2 and 1F1 show significantly higher specific activity on glucose than TNXI and TNXI V185T at all temperatures. At their optimal temperatures of activity (i.e., 90° C. for 1F1 and 95° C. for 3A2), both mutants are ~3-fold more active than TNXI V185T. Activation energies ($E_a$'s) for activity on glucose were calculated from the linear regressions shown in FIG. 1B, using the equation $A=A_0 e^{-Ea/RT}$. Whereas TNXI V185T shows the same activation energy as TNXI (i.e., 87 kJ/mole), 3A2 and 1F1 show significantly decreased Ea's (57 and 44 kJ/mole, respectively). These lower Ea's explain why 3A2 and 1F1 are as much as 7.3 and 12.3 times more active, respectively, than TNXI at 60° C., but only 4.2 and 4.8 times more active, respectively, than TNXI at 90° C.

The effect of pH on the activities of TNXI and its mutant derivatives is shown in FIG. 2. 3A2 and 1F1 show significantly increased specific activity on glucose compared to TNXI and TNXI V185T over the entire active pH range. The activity increase is so significant that 3A2 and 1F1 are more active at pH 5.5 than TNXI and TNXI V185T are at pH 7.0.

Kinetic parameters of TNXI 3A2 and 1F1: The kinetic parameters on glucose of TNXI V185T, 3A2, and 1F1 were compared in different conditions of temperature and pH (Table 1). In all conditions tested, TNXI 3A2 and 1F1 showed higher $K_M$ and $V_{max}$ values than TNXI V185T did. At pH 7.0 (both at 60° C. and 80° C.), TNXI 3A2 and 1F1's $V_{max}$ values increased more significantly than their $K_M$'s for glucose, yielding important increases in catalytic efficiencies (up to 2.3 fold for 1F1 at 60° C. [pH 7.0]). At 80° C. (pH 5.5), the increases in TNXI 3A2 and 1F1's $V_{max}$'s do not compensate for the major increases in their $K_M$ for glucose (i.e., 3.0 fold for 3A2 and 4.6 fold for 1F1). In these conditions, TNXI 3A2 and 1F1 show catalytic efficiencies that are approximately half that of TNXI V185T. At 60° C. (pH 5.5), TNXI 3A2's increase in $V_{max}$ does not compensate for a poor glucose affinity (high $K_M$), resulting in a lower catalytic efficiency than that of TNXI V185T. Unlike TNXI 3A2, 1F1 has a higher catalytic efficiency on glucose than TNXI V185T does due to a dramatic increase (5 fold) in its $V_{max}$ that surpasses the increases in its $K_M$ (3.7 fold) in these conditions. Its 5-fold increase in $V_{max}$ makes 1F1 a 1.7 fold more active enzyme at 60° C. (pH 5.5) than TNXI V185T is at 80° C. (pH 7.0).

Figure 3:
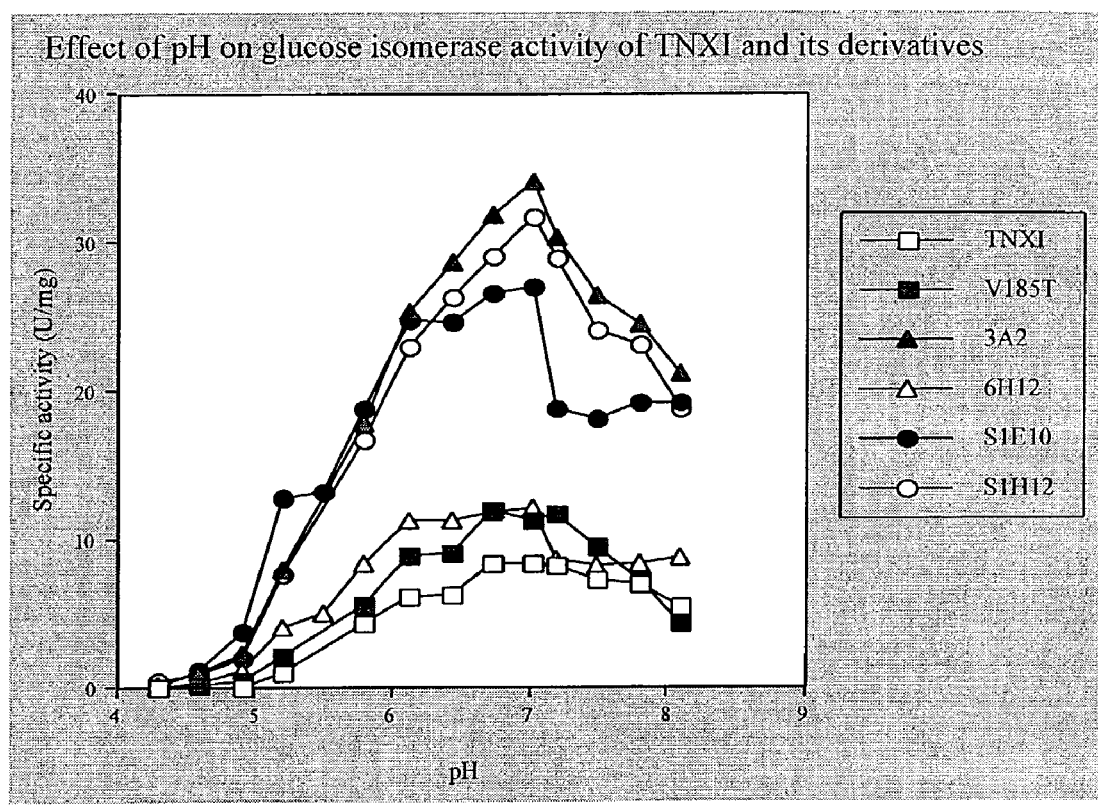
FIG. 3 is a graph showing the effect of pH on glucose isomerase activity of TNXI and its derivatives.

Thermal stability of TNXI 3A2 and 1F1: To determine whether the mutations present in 3A2 and 1F1 affected the kinetic stability of the mutated enzymes, the residual activities of 3A2 and 1F1 were measured after heat treatment at 80° C. (pH 7.0) and 80° C. (pH 5.5) for various lengths of time (FIG. 3). Stability experiments performed with the metal-free enzymes in 10 mM MOPS (pH 7.0) containing 0.5 mM $CoCl_2$ showed that 3A2 and 1F1 (with $t_{1/2}$ of 4.5 hr and 6.7 hr, respectively) were kinetically more stable than TNXI ($t_{1/2}$ of 1.6 hr) and TNXI V185T ($t_{1/2}$ of 3.8 hr). At pH 5.5, 1F1 ($t_{1/2}$ of 3.0 hr) remained more stable than TNXI ($t_{1/2}$ of 1.3 hr) and TNXI V185T ($t_{1/2}$ of 2.3 hr); 3A2 was less stable ($t_{1/2}$ of 1.7 hr).

Figure 4:
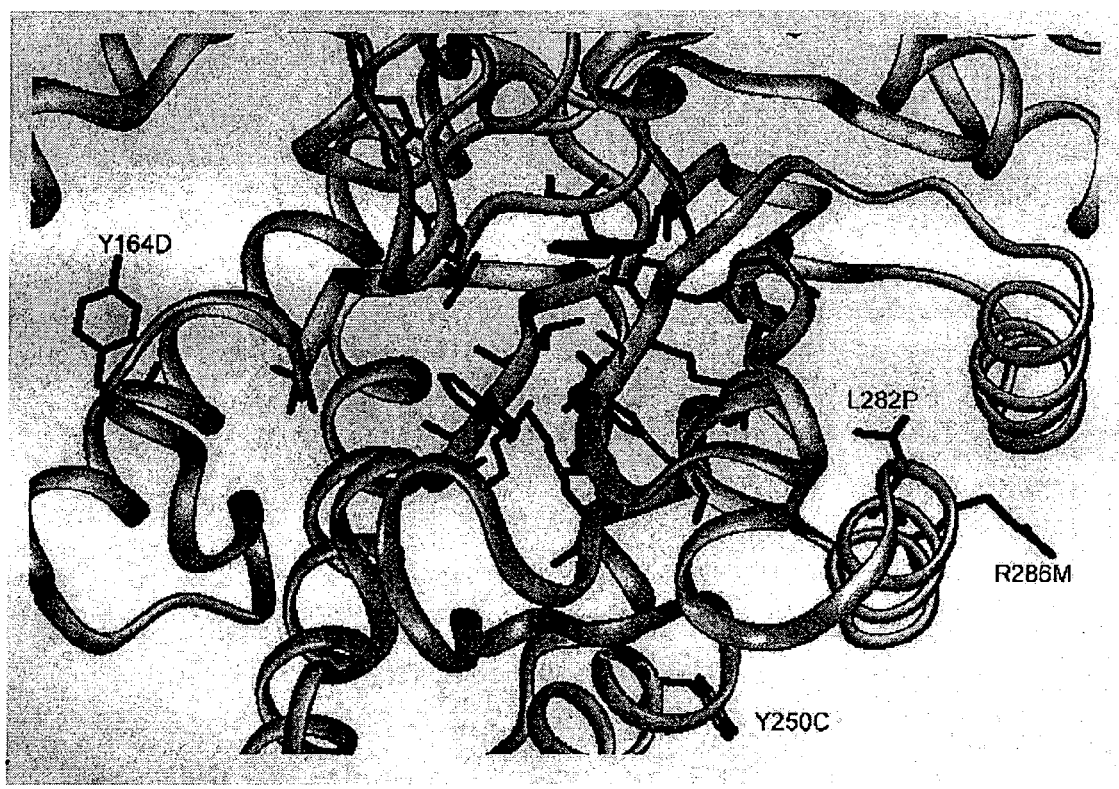
FIG. 4 is a 3D-structural model of TNXI showing all 4 mutations occurring in mutants which are obtained from Error-Prone PCR of TNXI Val185Thr and DNA shuffling, with the Leu283Pro mutation occurring in TNXI 3A2.

Amino acid substitutions in TNXI 3A2 and 1F1: The mutations present in 3A2 and 1F1 were identified by DNA sequencing. In addition to Val185Thr already present in TNXI V185T, 3A2 contained a single additional mutation, Leu282Pro. The Leu282Pro mutation is located in helix $\alpha_7$ of the $(\alpha/\beta)_8$-barrel structure, at approximately 12–14 Å from the catalytic center (FIG. 4). Helix $\alpha_7$ itself is located at the surface of a monomer and at the interface of the tight dimer. Neither Leu nor Pro's sidechain can form hydrogen bonds with neighboring residues. Whenever a proline occurs in a peptide chain, it interrupts $\alpha$-helices and creates a kink or bend (Lehninger, 1970). Detailed analysis of the Leu28Pro mutation modeled into the TNXI structure (FIG. 5) suggests that Pro282's pyrrolidine ring ($C_\gamma$, and $C_\delta$) is in close contact (in some cases ~1.7 Å) with mainchain atoms of residues Phe278 and Gln279. With van der Waal's radii of 1.87 and 1.35 Å for C and O atoms, respectively, in proteins, optimal van der Waal interactions between carbon atoms of Pro282 sidechain and the mainchain C and O atoms of residues Phe278 and Gln279 would take place at approximately 3.2 Å to 3.7 Å. The unfavorable van der Waal contacts (clashes) probably lead to local conformational rearrangements. These changes might, in turn, affect the active site structure and dynamics, the enzyme's interaction with the substrate, and probably inter-subunit interactions within the tight dimer.

Figure 6:
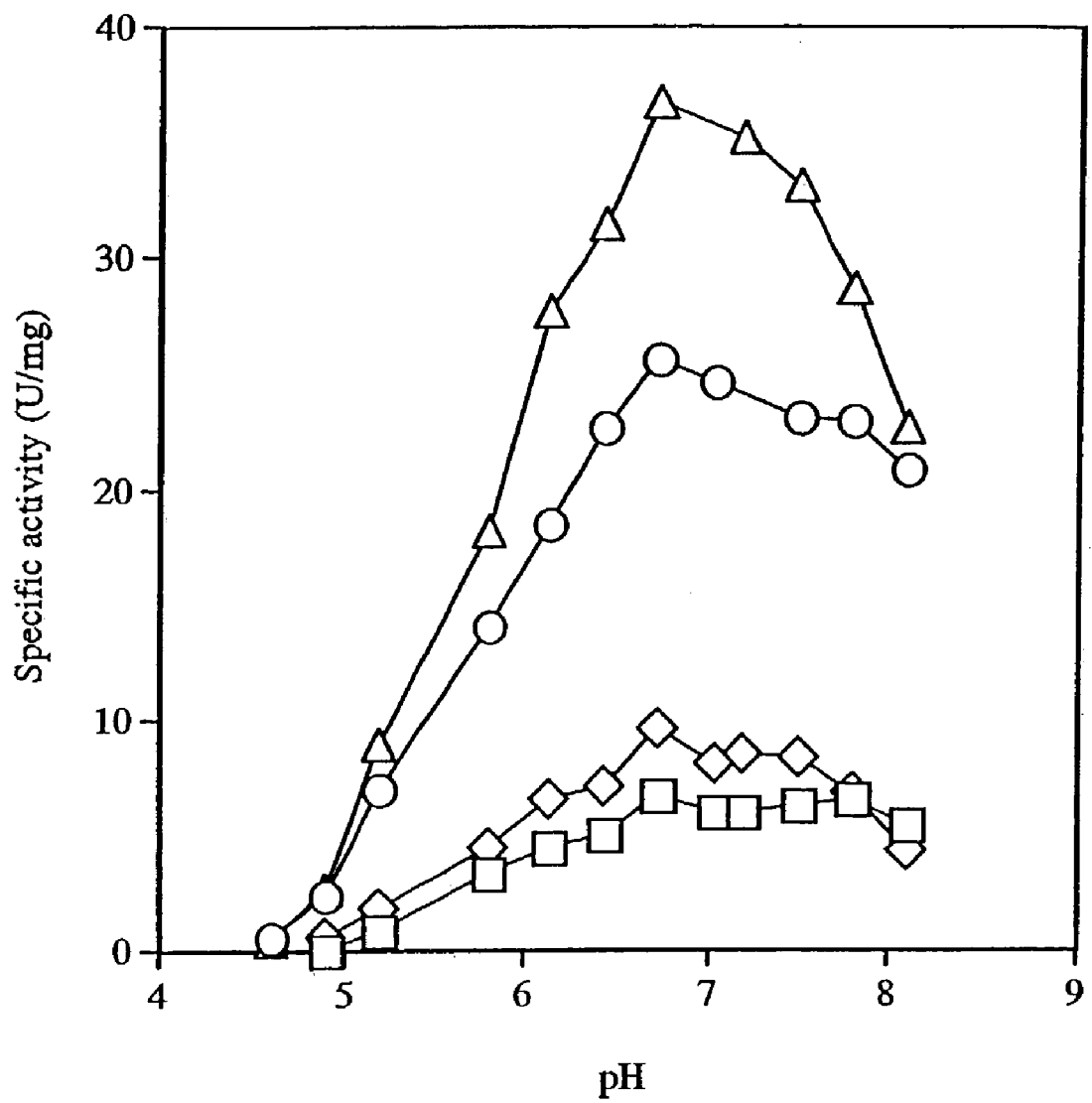
FIG. 6 is a graph showing the effect of pH on specific glucose isomerase activities of TNXI and its mutant derivatives at 80° C. (□): TNXI: (◇): TNXI V185T; (o): TNXI 3A2; (Δ) TNXI 1F1.

1F1 contains the same two mutations as 3A2, plus mutation Phe186Ser. This last mutation is located in the active site, adjacent to mutation Val185Thr (FIGS. 4 and 6). Serine's sidechain is much less bulky than that of the original Phe. Residue 186's sidechain points into the active site cavity, and it is close to the bulky sidechains of residues Tyr184, Phe228, Phe262, and Leu229. The Phe186Ser mutation probably leads to a rearrangement of the neighboring residues. This change in local packing may in turn be responsible for the large increase in low temperature activity of mutant 1F1.

Discussion

Thermostable enzymes are generally barely active at low temperature, but they are as active at their optimal growth temperature as their mesophilic counterparts (Zeikus and Brock, 1970; Varley and Pain, 1991). It was shown here that activity of a hyperthermostable enzyme at low temperature and low pH can be improved without a loss in its extreme stability. Our results have shown that the quality of the library of random TNXI mutants is sufficient to isolate mutants with increased activity at low temperature and low pH. Using two sequential rounds of random mutagenesis, we were able to obtain a TNXI mutant derivative, 1F1, showing high activity at low temperature and low pH. 1F1 is not only more active overall than its parental enzymes, but it is also more active especially at low temperature than its parental enzymes. Since 1F1 is more active at low temperature with a lower temperature optimum but more stable than the wild-type enzyme, we suggest that the molecular determinants of this enzyme's activity and thermal stability are in fact, not the same. This assumption has also been previously observed in the study of *Bacillus subtilis* p-nitrobenzyl esterase, in which the laboratory-evolved mutant enzyme had a 14° C. increase in $T_m$ but still maintained its catalytic activity at low temperature (Giver et al., 1998).

Recent studies (Aguilar et al., 1997; Zavodsky et al., 1998; Kohen et al., 1999) suggested that it might be the reduced flexibility of thermostable enzymes that impairs their catalytic activity at low temperatures. Particularly striking is the potential of single point mutations to significantly increase low temperature activity. Recent studies of psychrophilic enzymes have suggested that, despite the many differences observed between mesophilic and psychrophilic enzymes, single amino acid substitutions may be capable of conferring most psychrophilic characteristics (Somero, 1995; Feller and Gerday, 1997). Other studies using random mutagenesis and screening/selection succeeded in increasing the activity (by 3 fold at 20° C. for *Pyrococcus furiosus* β-glucosidase and by 17 fold at 37° C. for *Sulfolobus solfataricus* indolglycerol phosphate synthase) of hyperthermophilic enzymes at mesophilic temperatures with changes in temperature optima (Merz et al., 2000; Lebbink et al., 2000). One study even increased the catalytic efficiency of a mesophilic subtilisin at 10° C. by 100% (Taguchi et al., 1999). In our study, TNXI 1F1 was obtained with 4.5 and 2.2 fold increases in $v_{max}$ at 60° C. (pH 7.0) and 80° C. (pH 5.5), respectively, with only 5° C. lower optimal temperature compared to those of TNXI V185T. The Arrhenius plot of activity of TNXI and its mutants (FIG. 1B) revealed that TNXI and TNXI V185T require higher levels of activation energy for their catalytic activities than either TNXI 3A2 or 1F1. The difference is more pronounced with 1F1 with an approximately 2-fold decrease in the $E_a$ of activation compared with TNXI and TNXI V185T. The reduction of $E_a$ of activity observed in TNXI 3A2 and 1F1 suggested improved dynamics and flexibility in the active site of the enzymes even at low temperature thus their activities at low temperature are vastly enhanced. Although TNXI V185T has improved catalytic efficiency on glucose compared to TNXI due to improved glucose binding affinity and higher catalytic rate (Sriprapundh et al., 2000), its $E_a$ of activity remained similar to TNXI's suggesting that its active site dynamics and flexibility remained unchanged. This observation is in good agreement with the assumption of cold-adapted thermophilic enzymes by Lonn et al. (2002) that mutations underlying the adaptation of enzymes to temperatures lower than their optima allow a higher degree of flexibility in areas that move during catalysis. This, in turn, reduces the free energy of activation compared with the wild type enzymes. The higher flexibility in areas that move during catalysis increases the $k_{cat}$ of the reactions catalyzed by the cold-adapted enzymes. A study of lactate dehydrogenases cold-adaptation (Fields and Somero, 1998) also found that mutations that increase flexibility in regions of the enzyme involved in catalytic conformational changes may reduce energy barriers to these rate-governing shifts in conformation and thereby increase $k_{cat}$. TNXI 1F1 has higher $k_{cat}$ and $K_M$ values than TNXI V185T does. This observation was rationalized in terms of localized increases in conformational flexibility; mutations that reduce the energetic barriers between different active site conformations (thus allowing for more rapid interconversion among them) will lead to higher values of $k_{cat}$. These same mutations, however, will allow the enzyme to populate conformations that bind substrate poorly more easily, leading to increases in $K_M$. Our present study provides obvious support for this hypothesis.

Our sequential random mutagenesis and screening approach with TNXI resulted in the identification of amino acid residues or local structural conformations that are critical for thermostability, metal-binding affinity, and low temperature/low pH catalytic activity. Two mutations were identified in TNXI 1F1 in addition to V185T, namely L282P and F186S. Leu282 is at the inter subunit interface of the enzyme tight dimer. While the L282P mutation improved the enzyme's low temperature and low pH activities, the detailed analysis of the modeled 3D structure of 3A2 revealed unfavorable van der Waal contacts between Pro282's pyrrolidine ring and the enzyme's backbone structure. These unfavorable contacts probably lead to local conformational rearrangements and make the enzyme less stable (as observed in the shortened half-life at pH 5.5 and lower $T_m$ values compared to TNXI and TNXI V185T). The second mutation, F186S, is located in the active site, adjacent to Thr185. Since serine's sidechain is considerably smaller than phenylalanine's, this mutation would create a cavity or increase mobility in the active site of the enzyme resulting in a dramatic improvement of 1F1's low temperature activity. A potential extra strengthening H-bond between Ser186's sidechain and the Leu229 mainchain O (<3.2 Å) might explain the increased kinetic stability of TNXI 1F1 that even surpassed that of TNXI. Because most mutations are destabilizing, the accumulation of multiple mutations, cold-adapting or otherwise, will eventually destabilize an enzyme in the absence of selective pressure to maintain stability (Giver et al., 1998). Without such selective pressure, a stabilizing mutation may occasionally be discovered. However, such events will be uncommon, and stability will ultimately decrease due to the accumulation of multiple destabilizing mutations (Wintrode et al., 2000). There are a few evidences that demonstrated the effect of positions where mutations occur on activity and stability of laboratory and naturally evolved enzymes. A study of psychrophilic enzymes revealed that amino acid substitutions distant from the catalytic center or in the major substrate-binding site of enzymes could lead to cold-adaptation (Feller and Gerday, 1997). In the studies done by Lebbink et al. (2000), all mutants containing subunit interface substitutions were less stable and had lower temperature optima than the wild-type *Pyrococcus furiosus* β-glucosidase, suggesting that subunit interfaces also play an important role in thermoadaptation. Our results showed that even without selective pressure to maintain thermostability, it is possible to obtain a mutant thermozyme with a mutation in the active site that has comparable thermostability with the wild-type enzyme while its low temperature and low pH activity are vastly enhanced.

The only directed evolution approach (or random mutagenesis) performed on xylose isomerase reported to date was by Lonn et al. (2002). The thermophilic type I *Thermus thermophilus* XI was subjected to one round of random PCR mutagenesis and screening for xylose isomerase activity at lower temperature than optimal. Three amino acid substitutions were identified as F163L in domain I (C-terminal tail), and E372G/V379A in domain II ([α/β]$_8$ barrel). These mutant enzymes showed improved catalytic rate constants ($k_{cat}$) by up to nine times on both xylose and glucose with up to 26 times higher $K_M$ values on xylose but relatively unchanged for glucose. All enzyme variants' relative activities on xylose are higher than the wild-type at low temperatures with lower thermostability. Kinetic analysis demonstrated that the increase in the relative activity in the enzyme variants for xylose at low temperatures was indeed caused by an increase in $k_{cat}$ and not by a decrease in the $K_M$ value. This suggests that the mutant enzymes did not acquire higher affinity for the substrate than the wild-type enzyme at lower temperatures. These results as well as ours suggested that amino acid substitutions distant from the catalytic center could lead to cold adaptation. The only difference between their work and ours was that we, in fact, were able to enhance the thermostability of our mutant enzyme while increasing its activity at low temperatures.

An alignment of different XIs (not shown) revealed that neither Pro282 nor Ser186 is present in any known XI. Because it is in the active site, mutation F186S could potentially have been rationally designed based on the structures of TNXI, TNXI V185T, and 3A2 in the presence and absence of substrate, and on modeling. In contrast, mutation L282P, in the middle of an α-helix, and 12 to 14 Å from the active site was completely unpredictable, and could only be obtained through directed evolution. With a vast improvement in specific activity at 60° C., at pH 5.5, a higher catalytic efficiency on glucose than TNXI V185T in all conditions tested, and a thermostability comparable to that of TNXI V185T, 1F1 could be an interesting candidate for industrial applications. Further study of 1F1's potential usefulness in conditions used in the industrial production of high fructose syrup in comparison with a commercially available glucose isomerase is underway.

Example 6

Biochemical properties and fructose productivities of a laboratory-evolved xylose isomerase from hyperthermophilic *Thermotoga neapolitana* (TNXI 1F1) and Gensweet™ (Genencor, Rochester, N.Y.), a commercially available glucose isomerase from a genetically modified strain of *Streptomyces rubiginosus* were compared. TNXI 1F1 displayed higher catalytic efficiencies on glucose at low or high temperature and pH ranges and had greater thermal stability than Gensweet™ despite having similar temperature optima of activity. This greater thermal stability together with the superior kinetic parameters on glucose render TNXI 1F1 a genuine candidate for the industrial glucose isomerization process based on the lifetime fructose productivity estimation. At high temperature and neutral to alkaline pH, the Maillard browning reaction is a major concern in the resulting syrups. This was overcome by using TNXI 1F1 for fructose production at 90° C. and pH 5.5–6.5.

The production of high fructose corn syrup (HFCS) using immobilized glucose isomerase (GI) is considered one of the largest commercial enzymatic processes (Klibanov, 1983a; and Bhosale et al., 1996). The last step of the process is the enzymatic isomerization of glucose into a mixture typically containing 42% fructose with 51% glucose and 7% oligosaccharides (Visuri and Klibanov, 1987). A costly fructose enrichment step is then typically employed to increase the fructose concentration to 55% level to give the same sweetness level as sucrose (at the same concentration of solids) for its major use (Bucke, 1981). The enzyme-catalyzed isomerization of glucose into fructose is carried out in industrial bioreactors at 55–60° C. where the half-life of GI is on the order of several weeks. Even a modest increase in the half-life of the enzyme will substantially reduce the cost of the HFCS production (Klibanov, 1983b).

Since most industrially employed GIs exhibit temperature optima in the range of 80–90° C. (Hartley et al., 2000), only insufficient operational stability precludes their use at these higher temperatures, which would be highly beneficial. Not only thermostability of commercial enzymes is the main limiting factor of such application at high temperature, but in high substrate concentrations, Maillard browning reaction of the enzyme with reducing sugars (e.g. glucose and fructose) is also the dominant reason for enzyme inactivation. Maillard reaction was considerably faster than other inactivation mechanisms (Visuri et al., 1999). Theoretically, Maillard reaction can be retarded at low temperature or low pH. Hence the use of highly thermostable GIs at higher temperature and lower pH than the current isomerization conditions would result in a more operational stability with reduced browning reactions. The proposed process would be ideal since previous liquefaction and saccharification steps were also performed at high temperature and low pH and minimal adjustment of isomerization condition would be required.

Xylose isomerase (XI) from the hyperthermophilic eubacterium *Thermotoga neapolitana* is one of the most thermostable characterized XIs (Vieille et al., 2001). The gene encoding the enzyme was cloned, sequenced, and expressed in *Escherichia coli* (Vicille et al., 1995). Its active site has also been engineered by site-directed mutagenesis to increase its activity on glucose rather than its natural substrate, xylose (Sriprapundh et al., 2000). TNXI V185T mutant derivative is more active, more glucose efficient, and more stable than the wild-type TNXI. This enzyme's activity on glucose at low temperature and low pH was recently further improved by directed evolution resulting in the TNXI 1F1 derivative(V185T/L282P/F186S) (FIG. 19 SEQ ID NO:11 from DNA; FIG. 20 SEQ ID NO:12) with higher overall activity on glucose throughout the temperature and pH ranges compared to TNXI V185T (Sriprapundh et al., in press). Despite its higher activity at low temperature, TNXI 1F1 remains relatively as stable as TNXI V185T and more stable than the wild-type TNXI. With such vast improvement in every aspect of TNXI 1F1, it would be interesting to compare its utility against a commercially available glucose isomerase to determine whether it can be genuinely considered for industrial applications.

In this study, the effect of temperature and pH on specific activity on glucose together with kinetic parameters and thermal stability in different incubation conditions were compared between the TNXI 1F1 and Gensweet™, a commercially available glucose isomerase from a genetically modified strain of *Streptomyces rubiginosus*. Furthermore, their fructose production in various combinations of pHs and temperatures as well as lifetime fructose productivities of each enzyme under these conditions were studied.

Materials and Methods

Enzyme source: Gensweet™ SGI, a xylose isomerase derived from a genetically modified strain of *Streptomyces rubiginosus*, was provided by Dr. Jay Shetty of Genencor International (Rochester, N.Y.) as a kind gift. SDS-gel electrophoresis showed that the enzyme was pure.

Protein Purification: TNXI 1F1 was purified using the procedure of Vieille et al. (1995) followed by an additional ion-exchange chromatography step. Partially purified enzyme was applied to a Q-Sepharose column (2.5×15 cm) equilibrated with buffer A, and the enzyme was eluted using a 500 ml linear 0–300 mM NaCl gradient in buffer A. The pooled fractions from the Q-Sepharose column were concentrated in a stirred ultrafiltration cell (MW cut-off 30 kDa) (Amicon, Beverly, Mass.) and dialyzed twice against buffer A. Concentrated, homogenous enzyme was dispensed and stored frozen at −70° C.

Glucose isomerase assays: TNXI 1F1 and Gensweet™ were assayed routinely with glucose as the substrate. The enzyme (1–1.5 mg/mL) was incubated in 100 mM MOPS buffer (pH 7.0) [or 100 mM sodium acetate buffer (pH 5.5)] containing 1 mM $CoCl_2$ and 0.4 mM glucose at 80° C. for 10 min. The reaction was stopped by transferring the tube to an ice bath. The amount of fructose produced was determined by the modified resorcinol-ferric ammonium sulfate-hydrochloric acid method (Schenk and Bisswanger, 1998). To determine the effect of temperature on the activity of TNXI 1F1 and Gensweet™, the holo-enzyme was incubated in the reaction mixture at the temperatures of interest in a heated water bath (45–95° C.) or a heated oil bath (95–110° C.) for 10 min. The effect of pH on activity was determined using the routine assay described above except that the MOPS buffer was substituted with 100 mM sodium acetate buffer (pH 4.3–5.8), 100 mM PIPES buffer (pH 6.1–7.0), or 100 mM EPPS buffer (pH 7.2–8.1). All pHs were adjusted at room temperature, and the $\Delta pKa/\Delta t$'s for acetate, PIPES, and EPPS (0, −0.0085, −0.011, respectively) (USB, Cleveland, Ohio) were taken into account for the results. To determine the kinetic parameters, assays were performed in the presence of 10–1,500 mM glucose, 50 mM MOPS (pH 7.0) and 1 mM $CoCl_2$. One unit of glucose isomerase activity is defined as the amount of enzyme that produces 1 μmol of fructose per minute under the assay conditions.

Thermal inactivation assays: To obtain the apo-enzymes (metal-free enzymes), the purified enzymes were incubated overnight at 4° C. in 50 mM MOPS buffer (pH 7.0) containing 10 mM EDTA. They were then dialyzed twice against 50 mM MOPS buffer (pH 7.0) containing 2 mM EDTA, and they were finally dialyzed twice against 50 mM MOPS buffer (pH 7.0) without EDTA. $CoCl_2$ (0.5 mM) was added to the apo-enzyme and equilibrated at 4° C. overnight before the thermoinactivation was initiated. The time course of irreversible thermoinactivation was measured by incubating the enzymes (0.1–0.2 mg/ml) in either 10 mM MOPS buffer (pH 7.0) or 10 mM sodium acetate (pH 5.5) at various temperatures for different periods of time in a heated water bath. Residual glucose isomerase activity was measured as described above at 80° C. The first order rate constant, k, of irreversible thermoinactivation was obtained by linear regression in semi-log coordinates. Enzyme half-lives were calculated from the equation: $t_{(1/2)}=\ln 2/k$.

Differential Scanning Calorimetry (DSC): DSC experiments were performed on a Nanocal differential scanning calorimeter (Calorimetry Sciences Corp., Provo, Utah) using a scan rate of 1° C./min. Samples were scanned from 25° C. to 100° C. The apo-enzymes were scanned against 50 mM MOPS (pH 7.0). Enzymes containing both $Mg^{2+}$ and $Co^{2+}$ were dialyzed against buffer A, then scanned against the dialysis buffer as control.

Fructose production experiments: TNXI 1F1 and Gensweet™ (50 μg) were incubated in 1 ml reaction in capped 1.5 ml tubes containing 2.5 M glucose, 5 mM $MgSO_4$, and 50 mM of either MOPS (pH 7.0) or sodium acetate (pH 5.5) at various temperatures for up to 24 hours. The reactions were then stopped on ice and were assayed for fructose produced by the method described above. Browness of resulting syrups was monitored by maximal absorbance at 425 nm.

Modeled fructose productivity: Lifetime fructose productivity of TNXI 1F1 and Gensweet™ were estimated using the one phase inactivation mathematical model (Bandlish et al., 2002). Kinetic and inactivation data for the soluble enzymes were used to eliminate variations due to non-optimal immobilization protocols and the potential influence of mass transfer limitations on immobilized enzyme kinetics. The final equations presented a derivative of parameters for GI kinetics that also considered the equilibrium between glucose and fructose:

$$\frac{P_{life}}{[E_0]} = \frac{[Glu]}{[Glu] + K_M} \frac{[k_{cat}]}{[k_D]}$$

$$\frac{P}{[E_0]} = \frac{[Glu]}{[Glu] + K_M}[1 - \exp(-k_D t)]\frac{[k_{cat}]}{[k_D]}$$

Using these equations, enzyme productivities (kg fructose per kg enzyme) were calculated using representative data for the soluble enzymes. The calculations assumed 3 M glucose feed, a representative of an industrial HFCS production (Pedersen 1993; Godfrey and West, 1996). Enzyme productivity, P, is defined as the total amount of glucose converted to fructose per unit amount of enzyme during a period of time.

Results

Effect of temperature and pH on TNXI 1F1 and Gensweet™ activities: The effect of temperature on TNXI 1F1 and Gensweet™ glucose isomerase activities is shown in FIG. 1. Both enzymes have comparable specific activities on glucose in the temperature range of 45–75° C. The optimal temperatures of glucose isomerase activity of TNXI 1F1 and Gensweet™ are 90° C. and 85° C., respectively. Although they have relatively the same activity at low temperature, TNXI 1F1 is much more active at its optimal temperature of activity with 47.6 U/mg compared with 30.9 U/mg of Gensweet™. FIG. 2 demonstrated the effect of pH on glucose isomerase activities at 80° C. of TNXI 1F1 and Gensweet™. The two enzymes have comparable activity over the pH range of 4.6 to 8.1 and retain more than 70% of their optimal activities in the pH range of 6.1 to 8.0.

Thermal stability of TNXI 1F1 and Gensweet™: To determine the thermal stability of TNXI 1F1 and Gensweet™, the residual activities of TNXI 1F1 and Gensweet™ were measured after heat treatment at 60° C., pH 7.0 and 5.5 for various lengths of time (FIGS. 3, A and B). Investigations of the metal-free enzymes in buffer at saturated $Co^{2+}$ concentration showed that at both pHs, TNXI 1F1 is far more superior in term of thermal stability when compared to Gensweet™ with half-lives of 115.5 and 38.5 hr at pH 7.0 and 5.5, respectively, compared to 2.9 and 1.7 hr for Gensweet™. The TNXI 1F1 is more stable than Gensweet™ by 1.6 and 1.36 orders of magnitudes at 60° C., pH 7.0 and 5.5, respectively. These results suggest that although Gensweet™ and TNXI 1F1 have almost the same temperature of optimal activity ($T_{opt}$), only TNXI 1F1 has extreme thermostability. Gensweet™, on the other hand, is thermophilic but obviously not thermostable.

TNXI 1F1 and GensweetTm's melting temperatures ($T_m$) were determined by DSC in the presence and absence of metals (FIG. 4, and Table 2). With the holo-enzymes, both scans revealed one thermal transition, at 107.3° C. and 93.4° C., for the TNXI 1F1 and Gensweet™, respectively. With a higher $T_m$ of ~14° C., TNXI 1F1 holo-enzyme is much more stable than that of Gensweet™ which is in good agreement with the results obtained from inactivation experiments. DSC of apo-enzymes of both enzymes also revealed one thermal transition 78.4° C. and 76.1° C. for the TNXI 1F1 and Gensweet™, respectively. The extent of $T_m$ difference observed in apo-enzymes was not as pronounced as that in holo-enzyme forms.

Kinetic parameters of TNXI 1F1 and Gensweet™: The kinetic parameters on glucose of TNXI 1F1 and Gensweet™ were compared in different conditions (Table 1). In all comparable conditions, Gensweet™ has higher $K_M$ and $V_{max}$ than TNXI 1F1 (except at 80° C., pH 5.5 in which TNXI 1F1's $V_{max}$ is higher than that of Gensweet™). The difference in $K_M$ of Gensweet™ and TNXI 1F1 is more pronounced than that of $V_{max}$ resulting in worse catalytic efficiency ($k_{cat}/K_M$) on glucose for Gensweet™ than TNXI 1F1. The TNXI 1F1's superiority of glucose catalytic efficiency on glucose is more noted at pH 7.0 than at pH 5.5 and at higher or lower than both enzymes' optimal temperatures (85–90° C.).

Figure 5A:
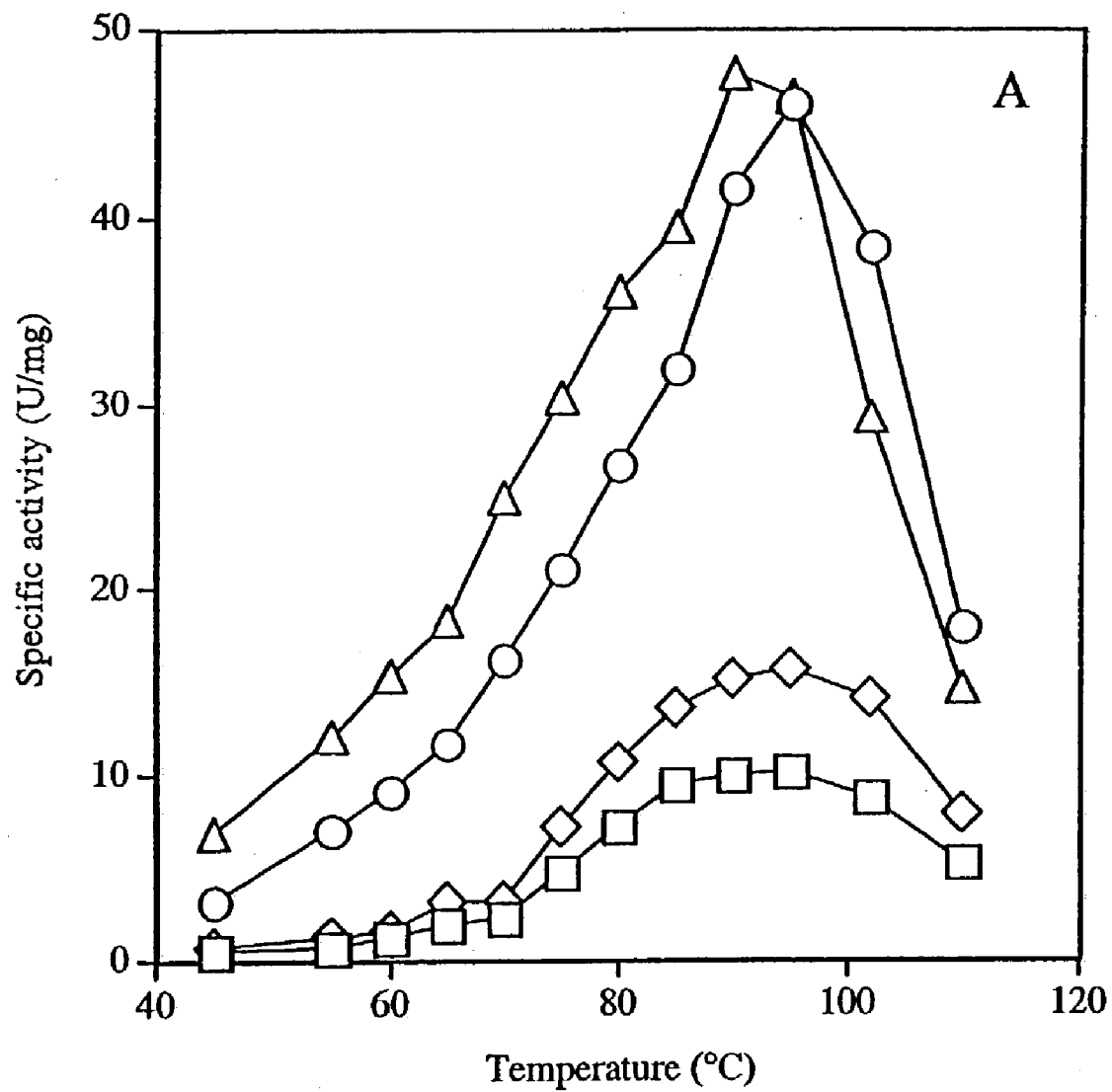
FIGS. 5A and 5B are graphs showing the effect of temperature on the specific activities of TNXI and its mutant derivative on glucose at pH 7.0. (□): TNXI: (◇): TNXI V185T; (o): TNXI 3A2; (Δ): TNXI 1F1. (A): Specific activity versus Temperature.
Figure 5B:
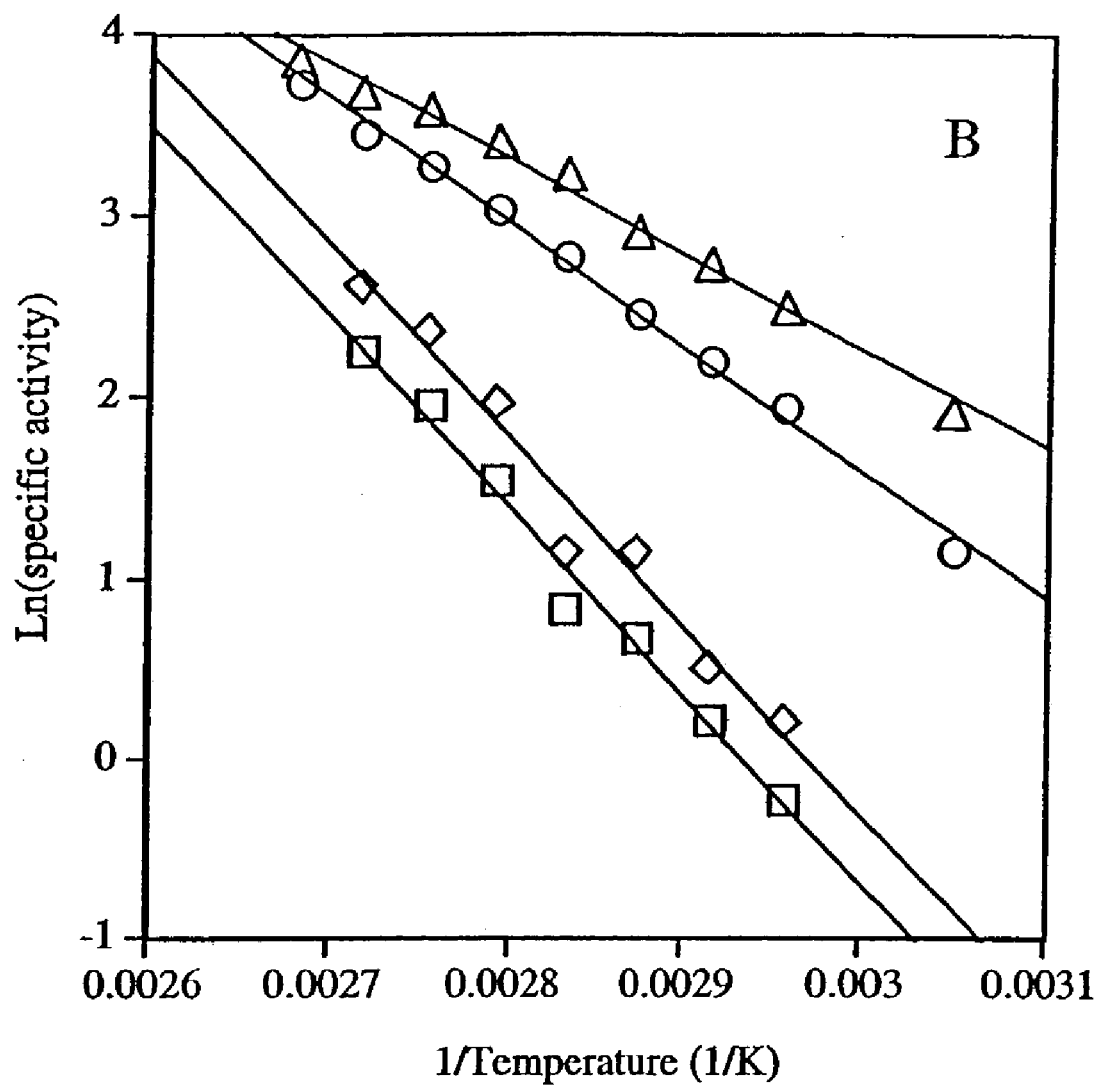

Modeled fructose productivity: Lifetime fructose productivity of both enzymes was estimated using the one phase inactivation model at various combinations of temperatures and pHs. The modeled time course of fructose productivity of TNXI 1F1 and Gensweet™ at various conditions is shown in (FIG. 5 and table 3). Fructose productivity of Gensweet™ at 80° C. cannot be generated because no residual activity was detected at 80° C. in buffer pH 7.0 and 5.5 after just 10 minutes. At 60° C., Gensweet™ produced a maximum amount of 1.3 and 0.4 kilogram (kg) fructose per gram (g) enzyme at pH 7.0 and 5.5, respectively. With lifetime fructose production of 30.5 and 4.4 kg fructose/g enzyme at pH 7.0 and 5.5, respectively, TNXI 1F1 yielded approximately 24 and 12-fold increases in fructose production compared to Gensweet™ under the same conditions. The main reason of TNXI 1F1 superior fructose productivity over Gensweet™ is mainly due to its higher thermostability. It is also important to note that the fructose production of Gensweet™ reached the maximum points before 24 hr whereas it took approximately 15 days at pH 5.5 and more than 30 days at pH 7.0 for TNXI 1F1 to reach its maximum production. At 80° C., TNXI 1F1 produced 4.5 and 2.4 kg fructose/g enzyme at pH 7.0 and 5.5, respectively. The production fructose reached the maximum point at approximately 2.5 days.

Figure 7A:
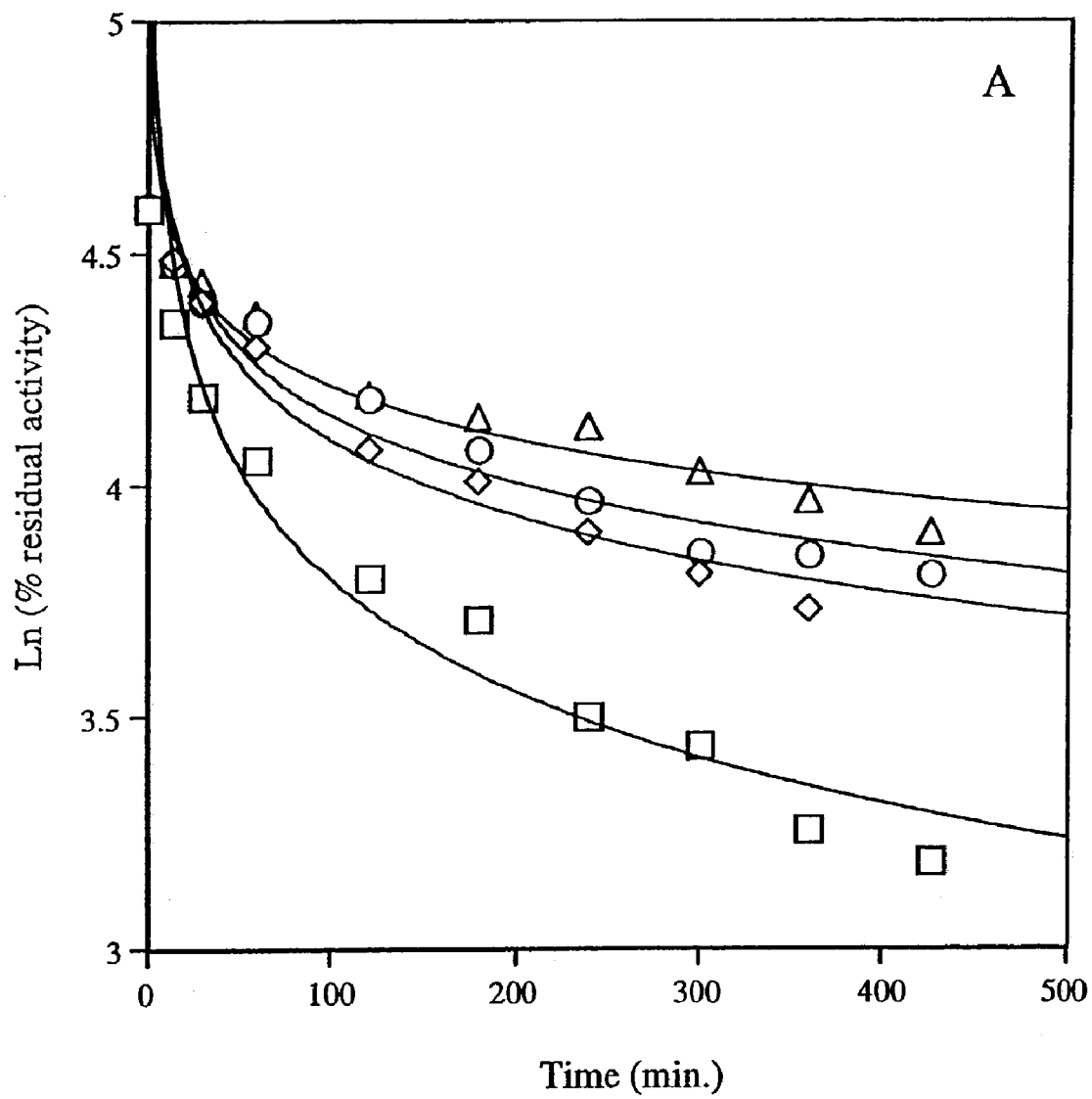
FIG. 7A is a graph showing inactivation curves of TNXI and its mutant derivatives at 80° C. (pH 7.0).
Figure 7B:
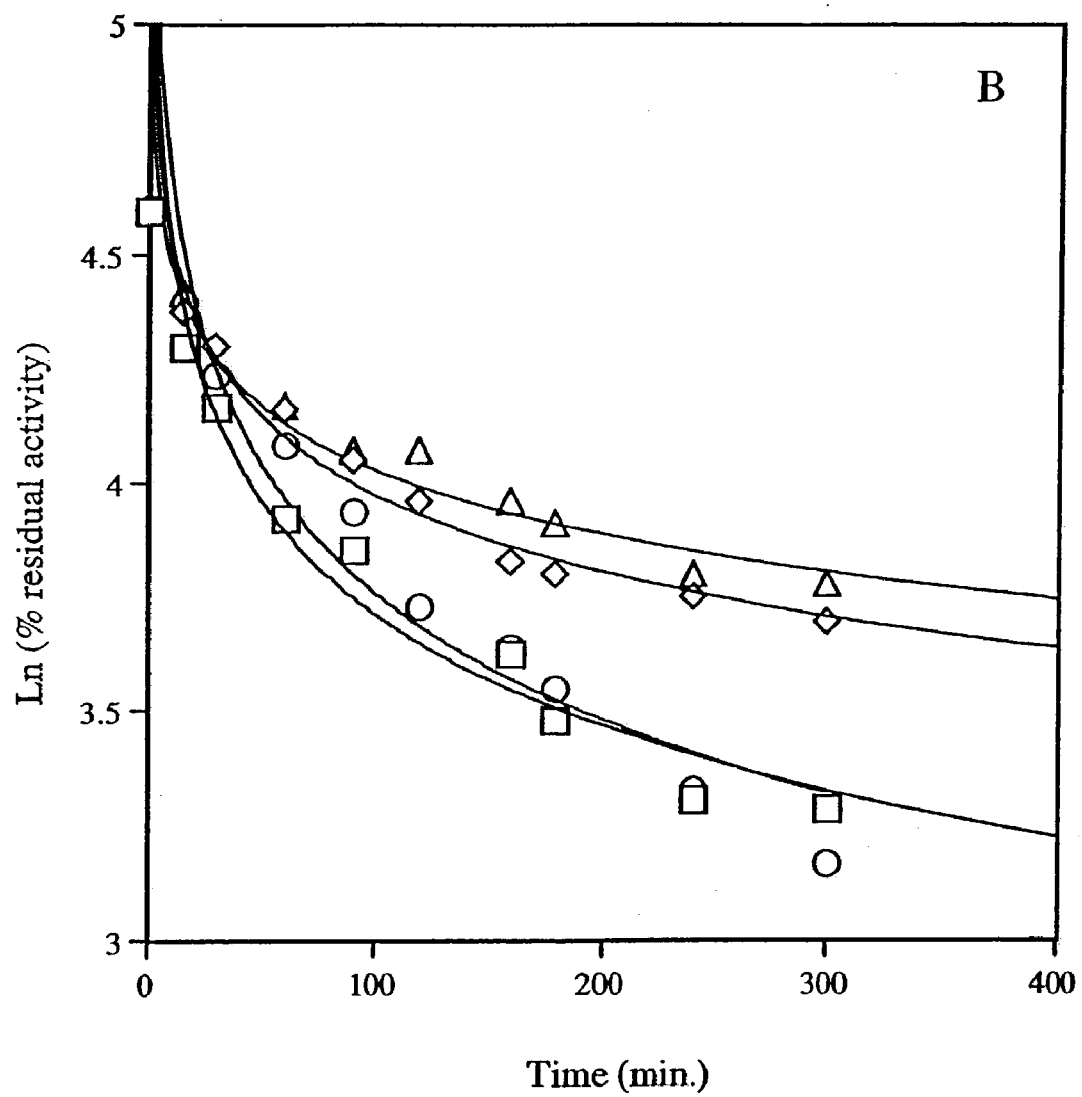
FIG. 7B is a graph showing inactivation curves of TNXI and its mutant derivatives at 80° C. (pH 5.5). The half lives of TNXI, TNXI V185T, TNXI 3A2, and TNXI 1F1 are (A) 3.9 hr, 5.0 hr, 6.4 hr, 7.7 hr and (B) 2.8 hr, 4.1 hr, 2.5 hr, and 4.8 hr, respectively. The symbols used are the same as in FIGS. 5A and 5B.
Figure 8A:
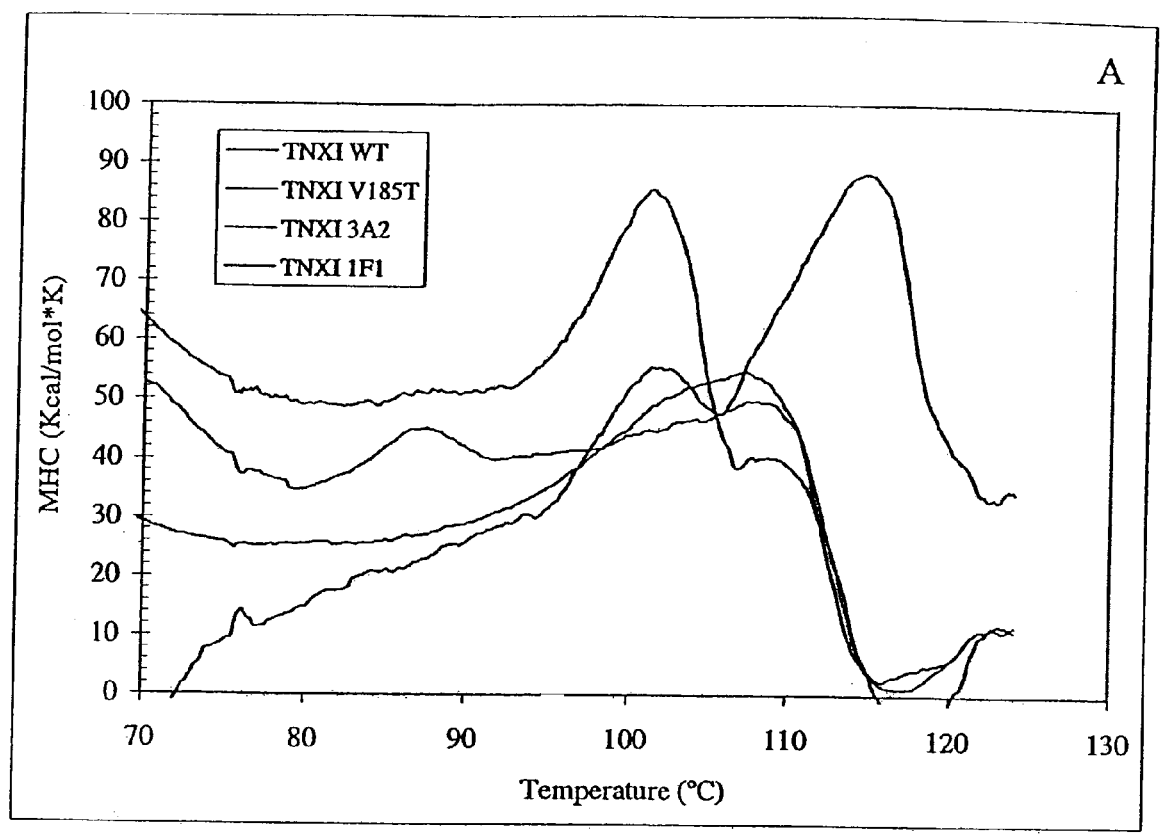
FIGS. 8A, 8B and 8C are graphs showing thermal unfolding of the apo forms of TNXI and its mutant derivatives in the presence (FIG. 8A) and the absence (FIGS. 8B and 8C) of 5 mM $MgSO_4$ and 0.5 mM $CoCl_2$ followed by DSC.
Figure 8B:
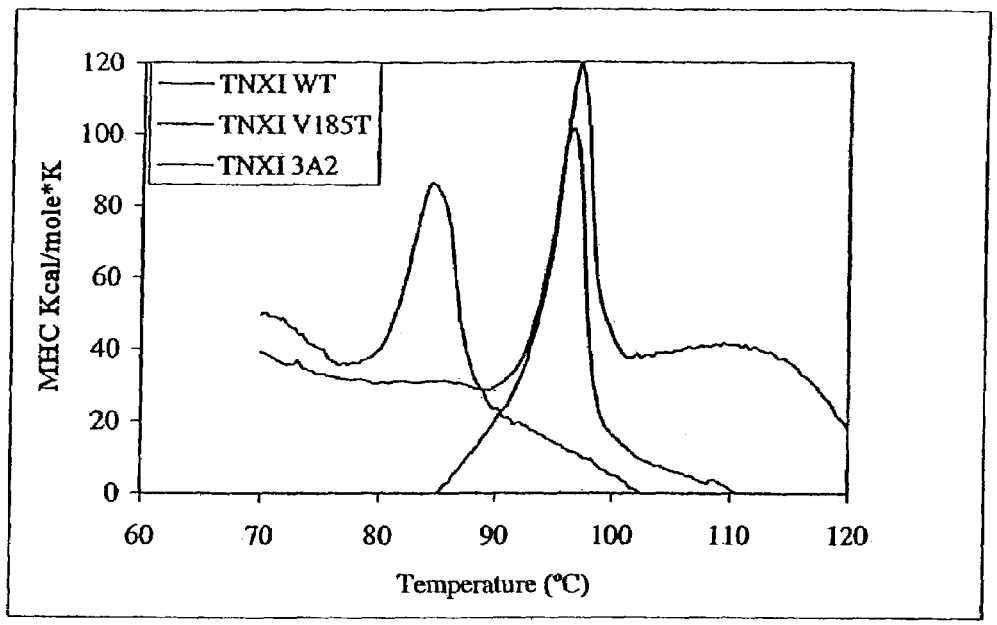
Figure 8C:
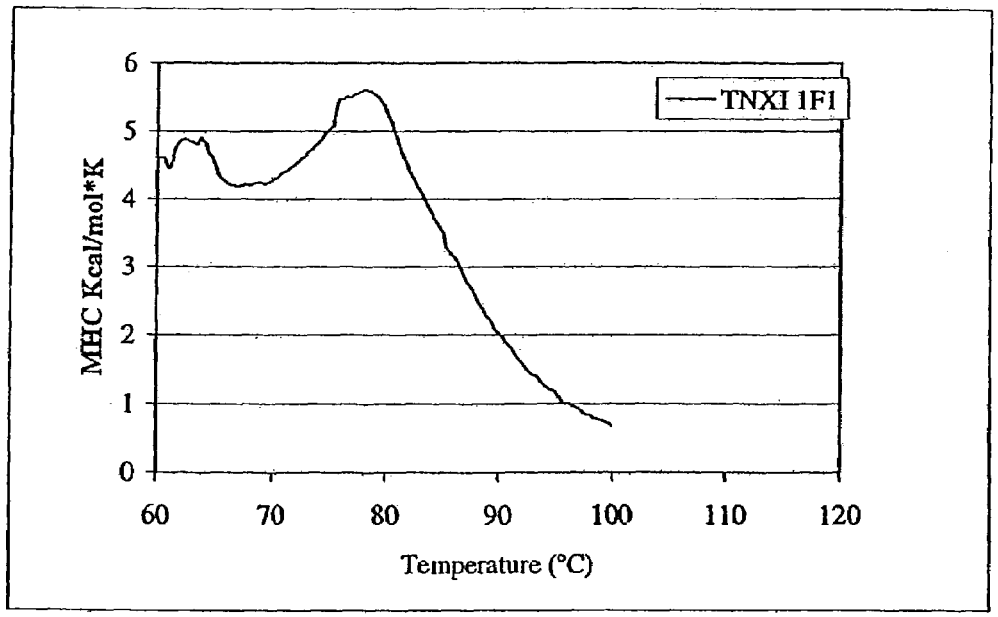
Figure 9:
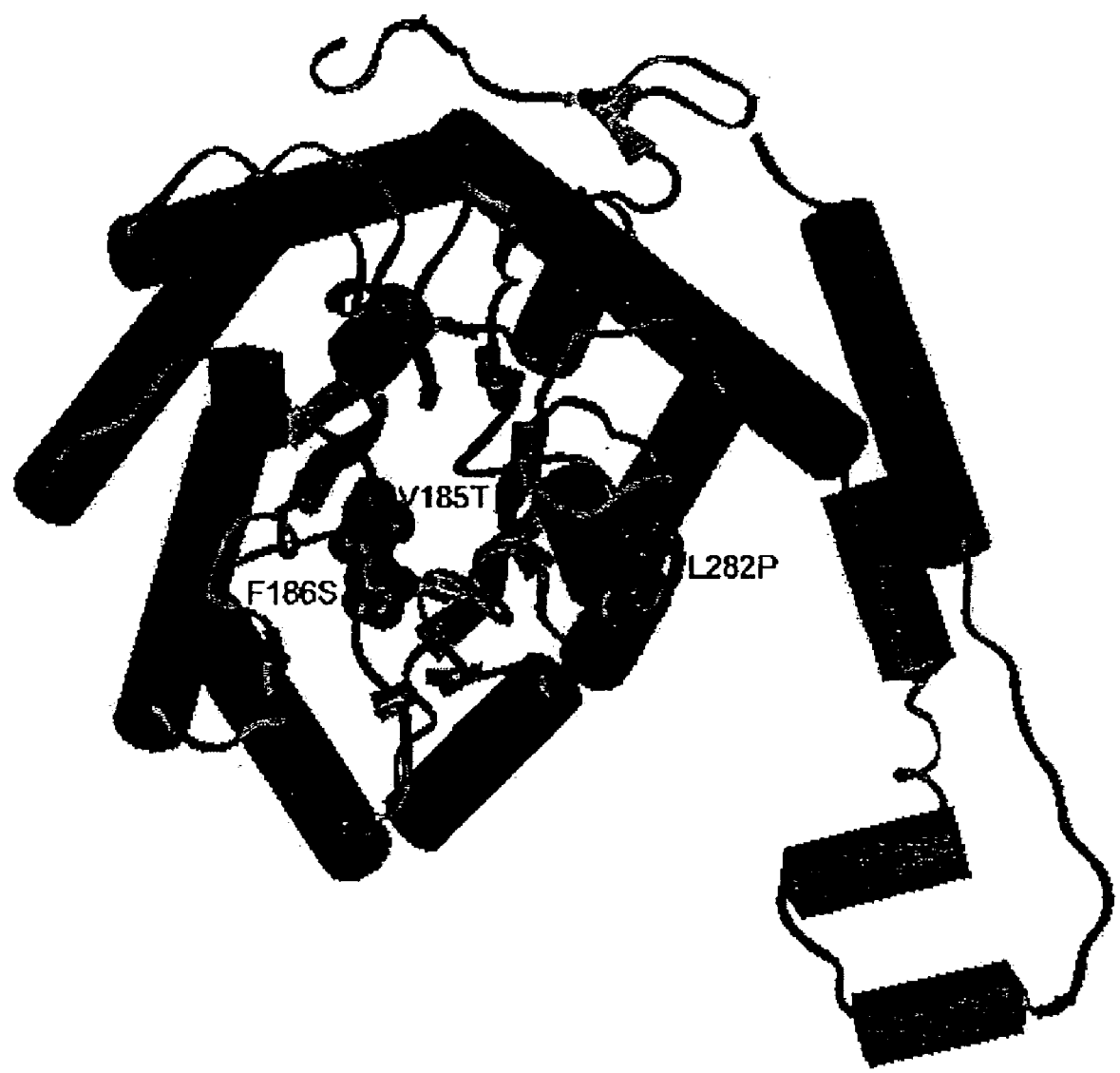
FIG. 9 is a three-dimensional model of the TNXI 1F1 monomer showing the positions of mutations V185T, F186S, and L1282P.
Figure 10:
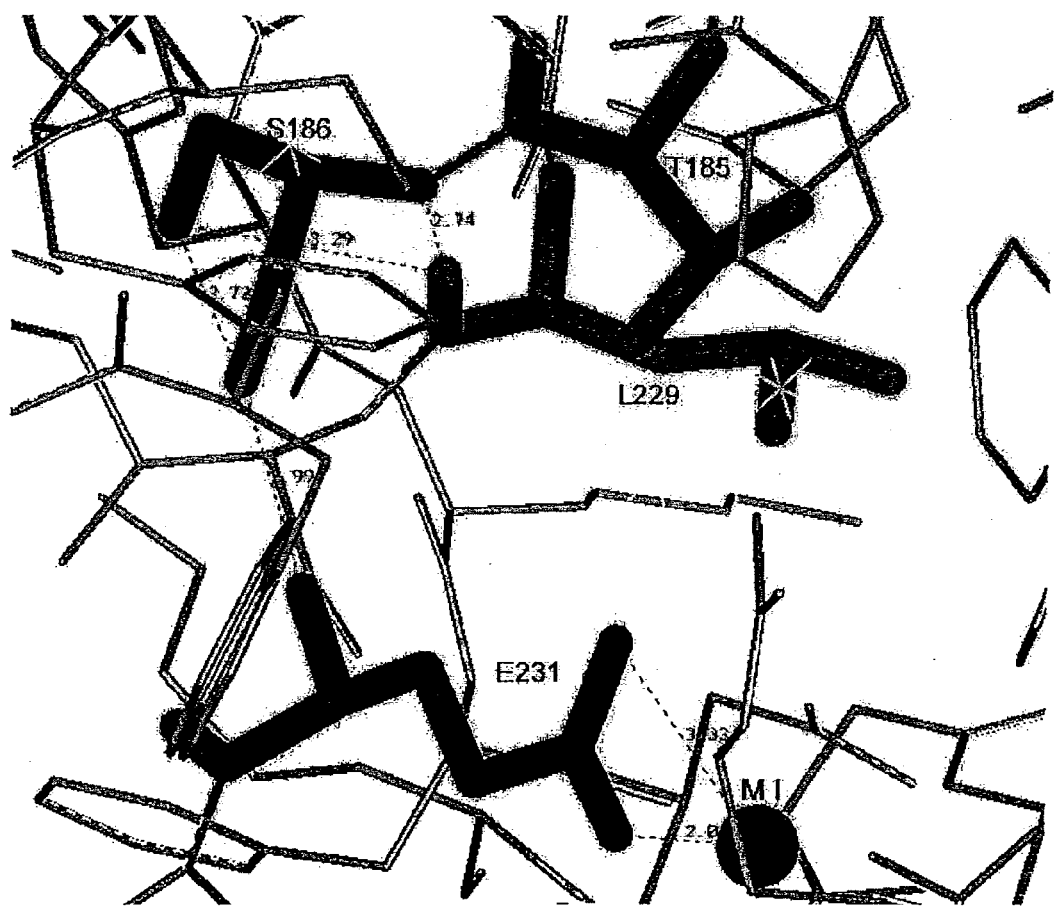
FIG. 10 is a three-dimensional model of part of the TNXI 1F1 active site showing hydrogen bonds among S186 (red), L229 (pink) and E231 (blue). E231 co-ordinates $Co^{2+}$ (purple ball) at the structural site (M1).
Figures 11A, 11B:
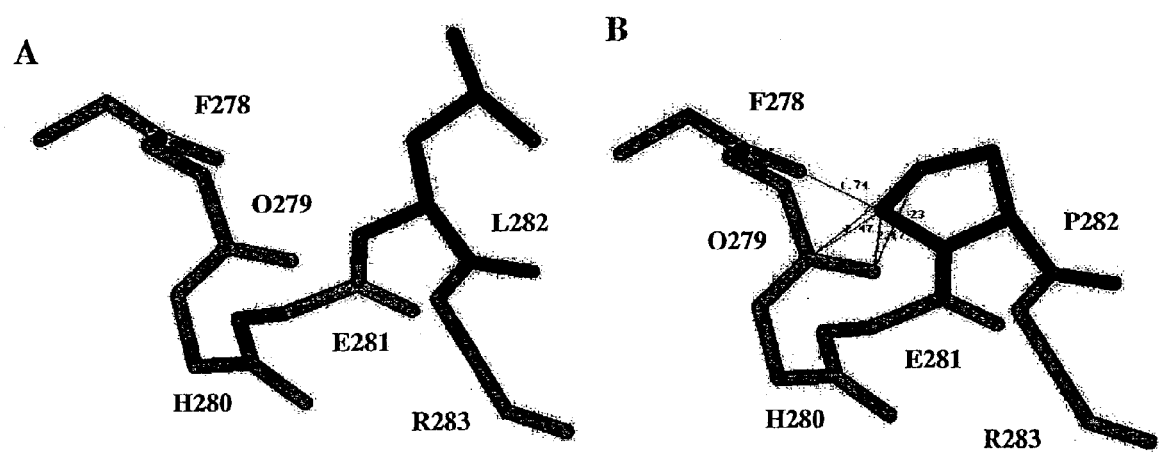
FIGS. 11A and 11B are three-dimensional models of parts of the area surrounding TNXI 3A2 and 1F1's Leu282Pro mutation. Backbone structure of residues 278–283 is shown in light green. Leu282 (A) and Pro282 (B) sidechains are shown in red.
Figure 12:
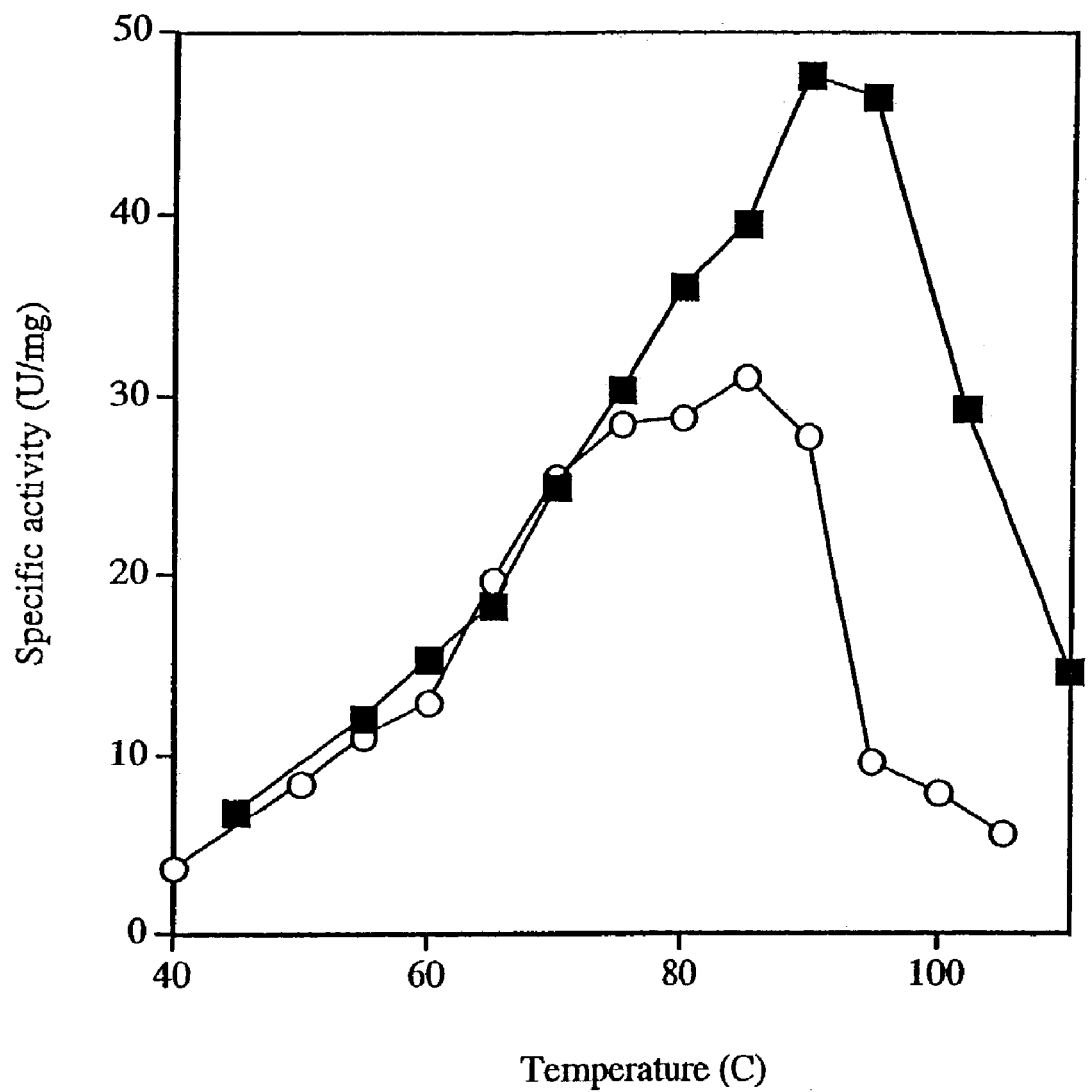
FIG. 12 is a graph showing the effect of temperature on the specific activities of (□): TNXI 1F1; (o): GENSWEET™ on glucose at pH 7.0.
Figure 13:
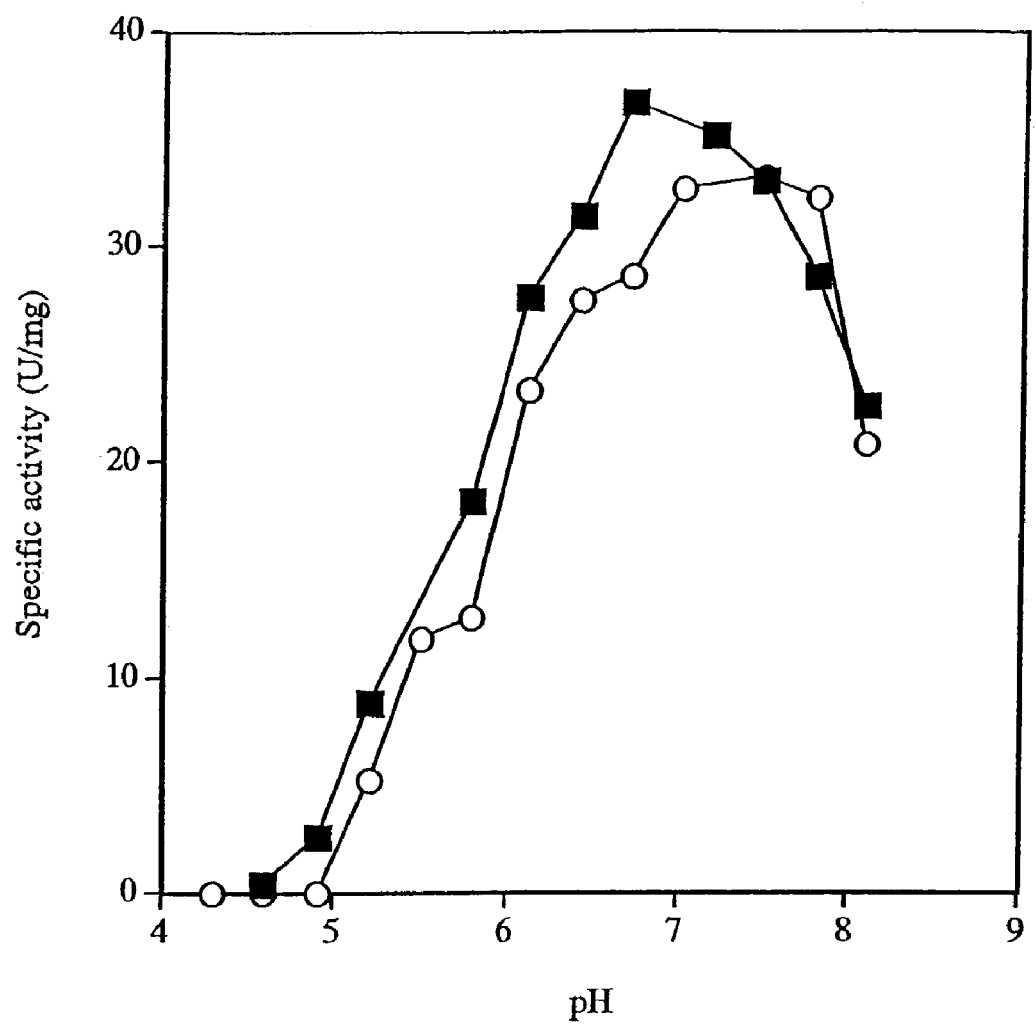
FIG. 13 is a graph showing the effect of pH on the specific activities of (□) TNXI 1F1; (o): GENSWEET™ on glucose at pH 7.0.
Figure 14A:
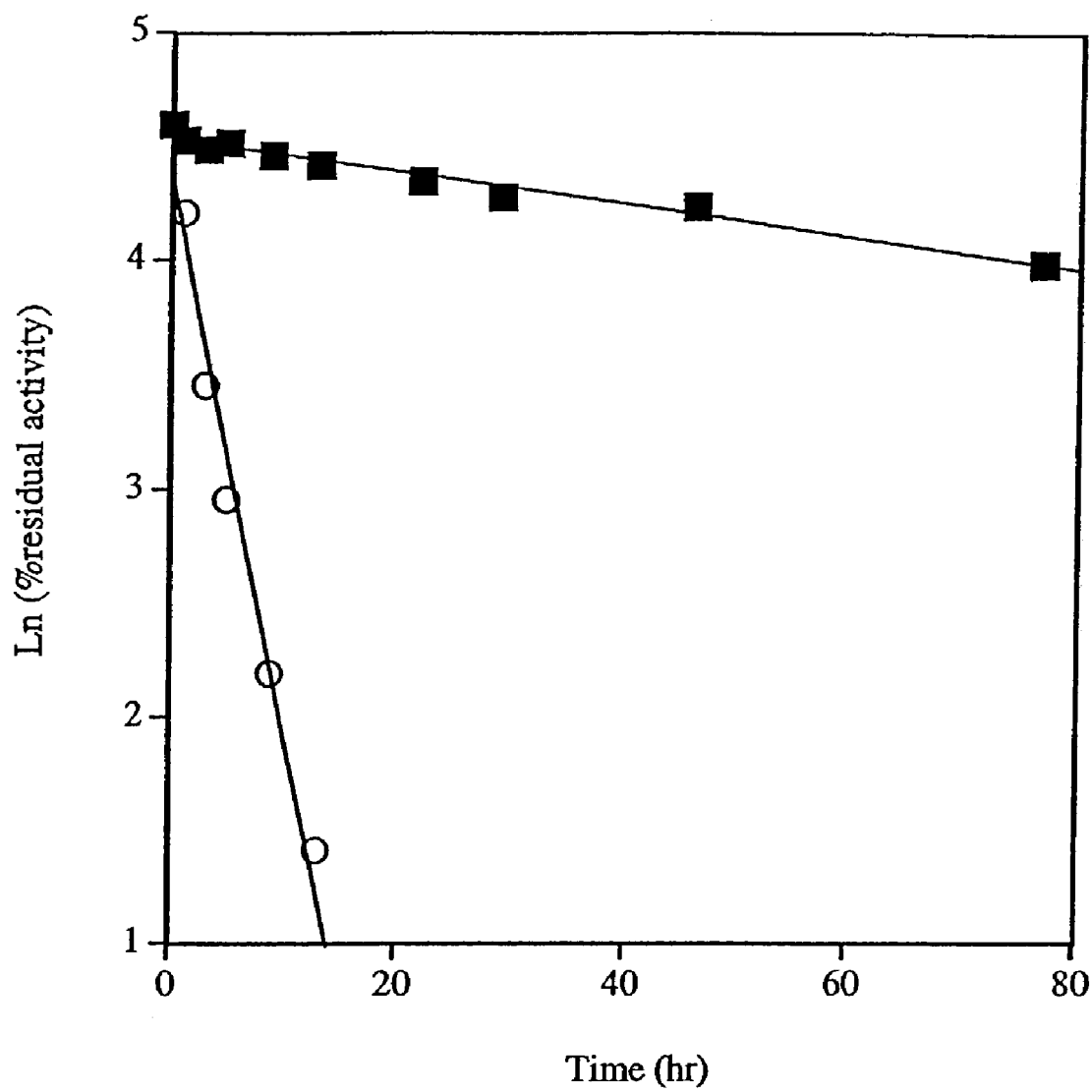
FIGS. 14A and 14B are graphs showing inactivation curves of TNXI and its mutant derivatives at 60° C. (pH 7.0) (FIG. 14A) and 60° C. (pH 5.5) (FIG. 14B). Symbols used are the same as in FIG. 1.
Figure 14B:
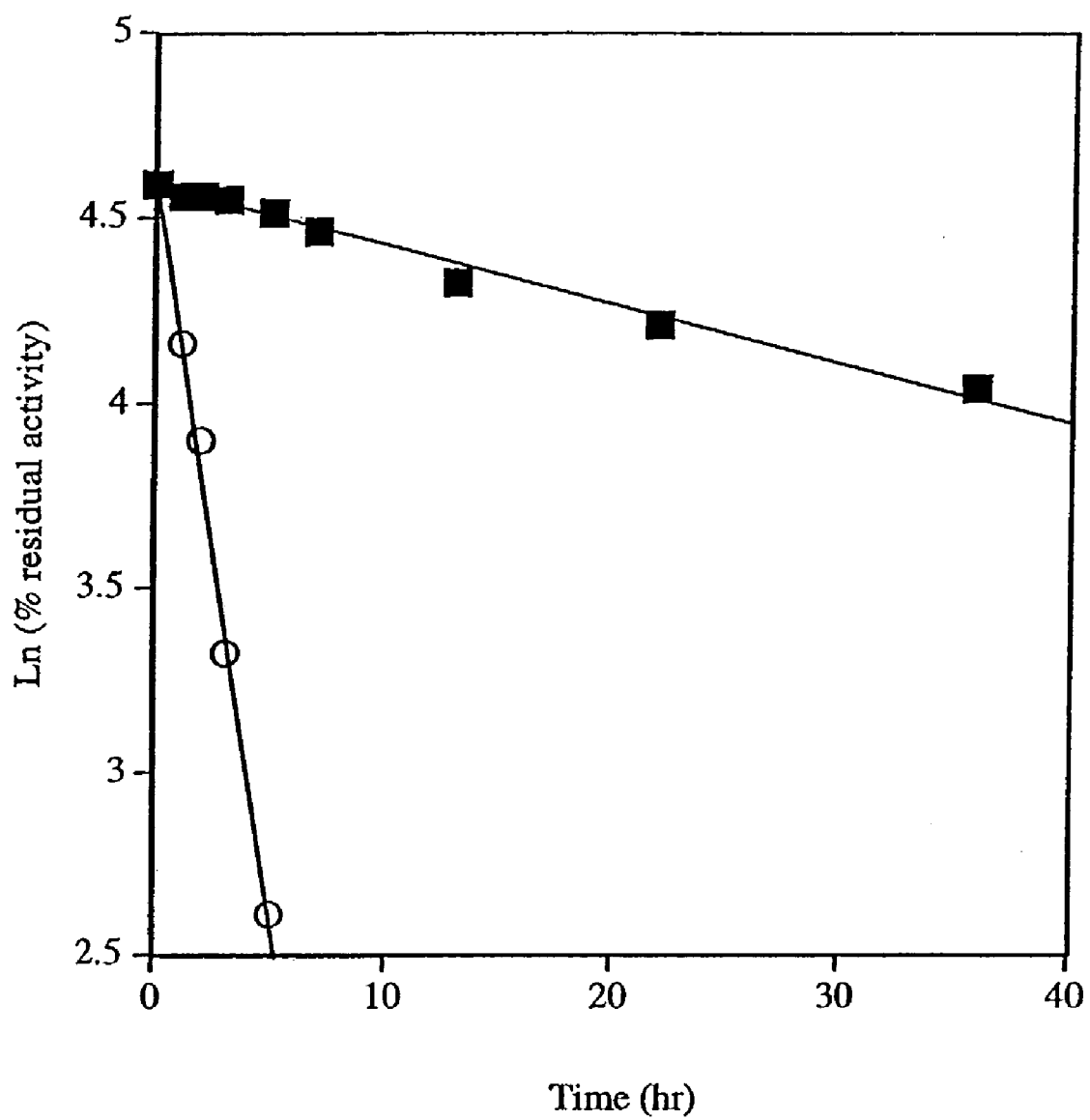
Figure 15A:
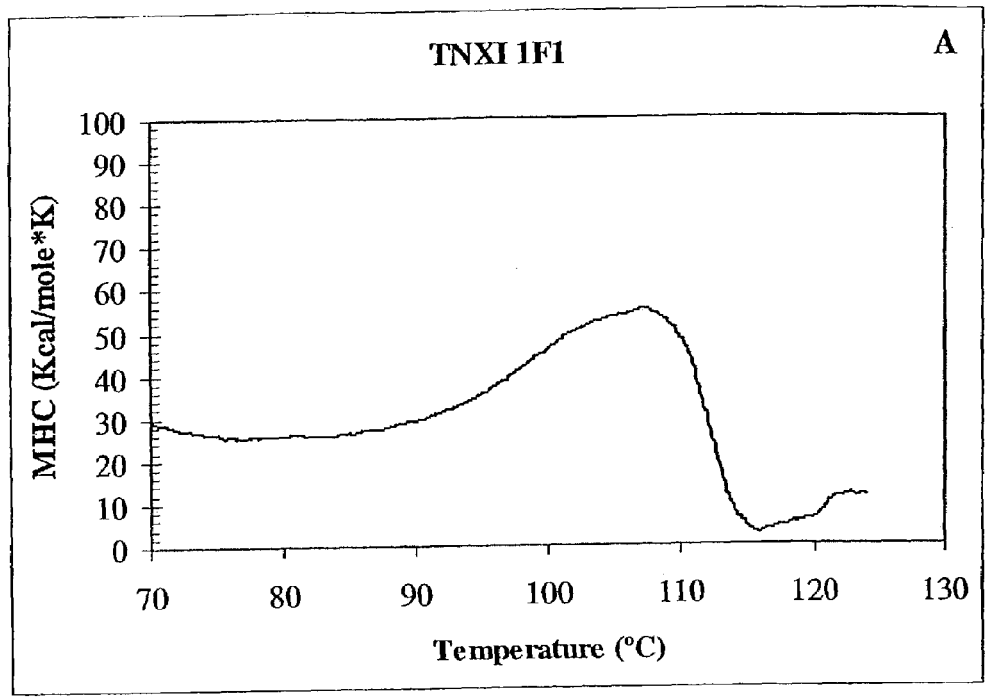
FIGS. 15A and 15B are graphs showing thermal unfolding of (FIG. 15A) TNXI F1 and (FIG. 15B) GENSWEET™ in the presence of 5 mM $MgSO_4$ and 0.5 mM $CoCl_2$ followed by DSC.
Figure 15B:
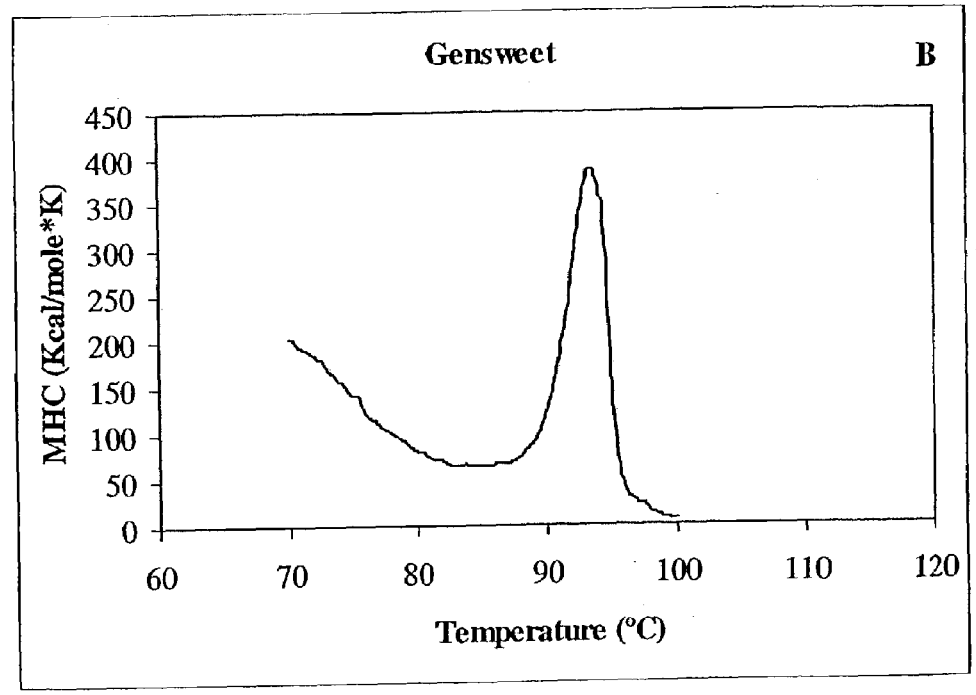
Figure 16A:
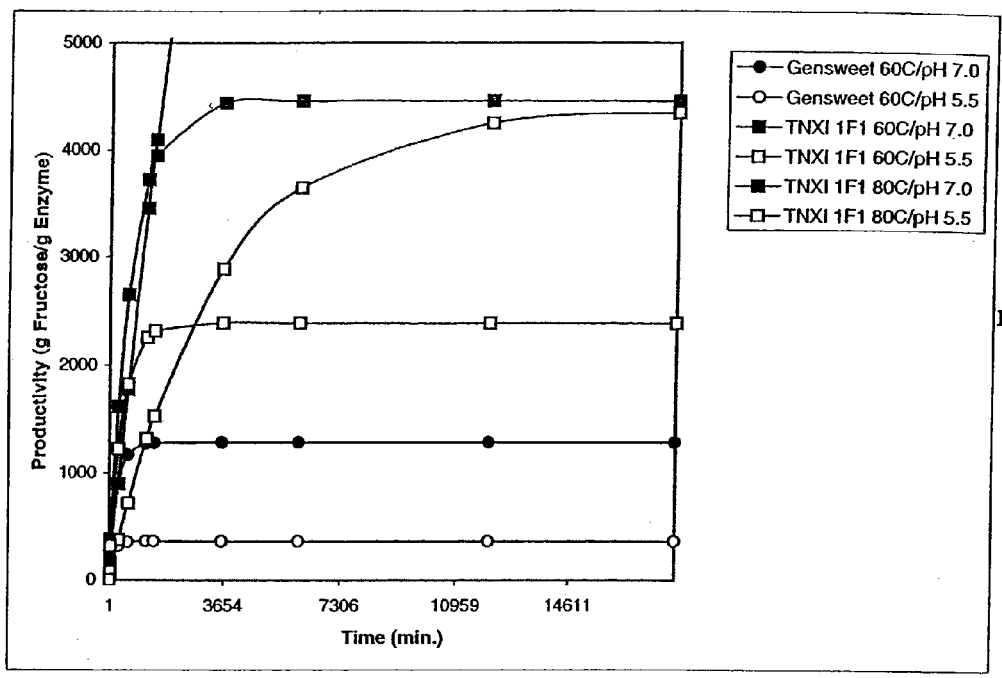
FIGS. 16A and 16B are graphs showing estimated fructose productivity of TNXI 1F1 and GENSWEET™ under different conditions.
Figure 16B:
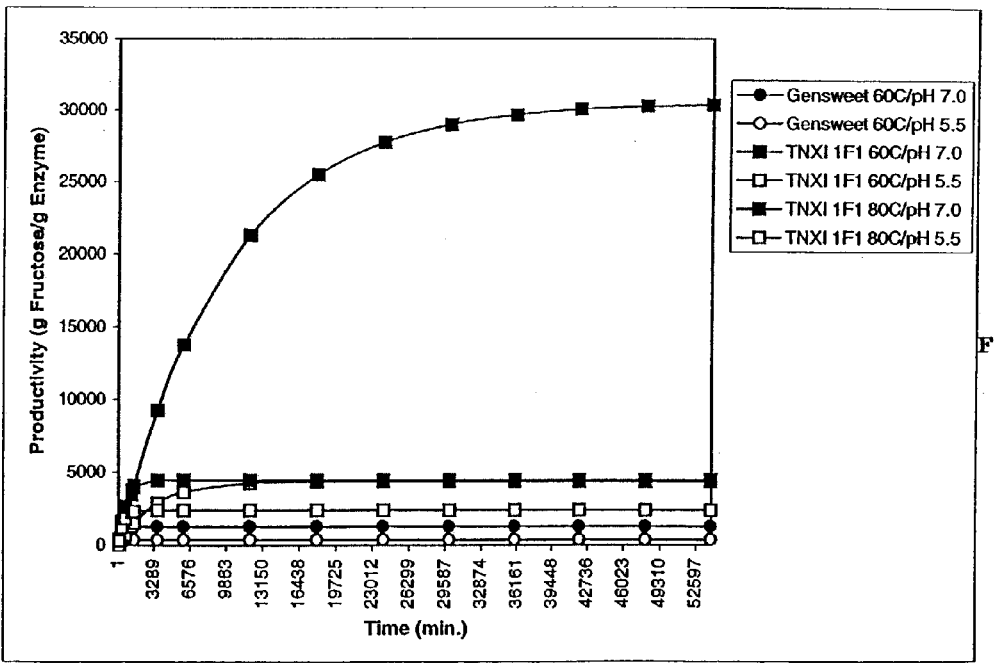
Figure 17A:
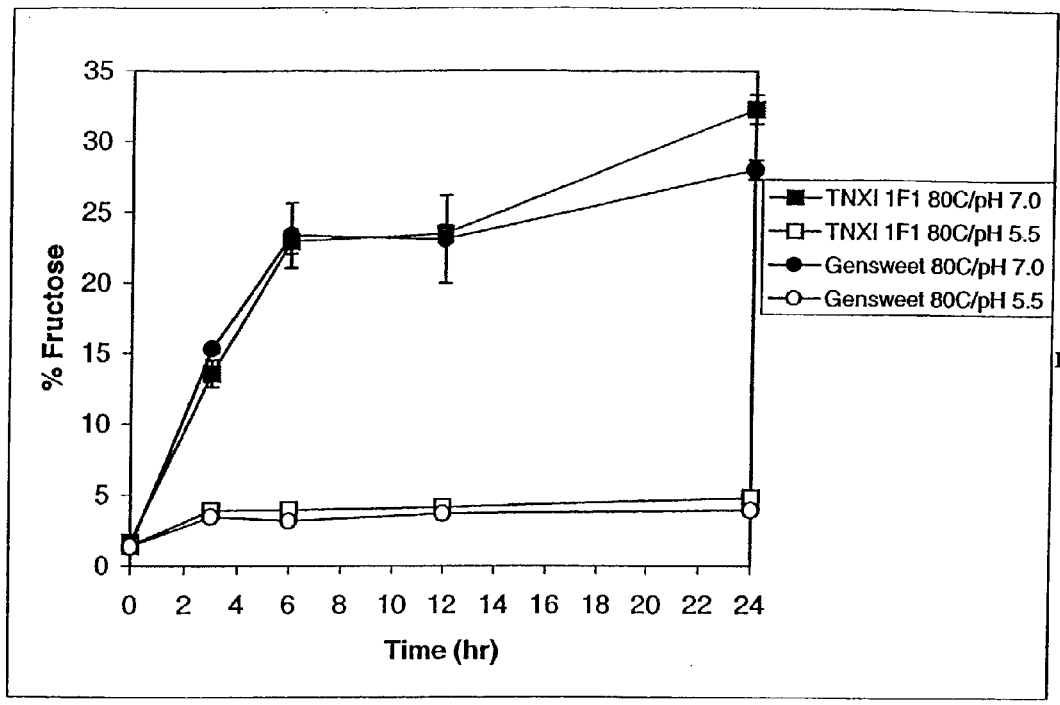
FIGS. 17A and 17B are graphs of experimental fructose conversion of TNXI 1F1 and GENSWEET™ at pH 7.0 and 5.5.
Figure 17B:
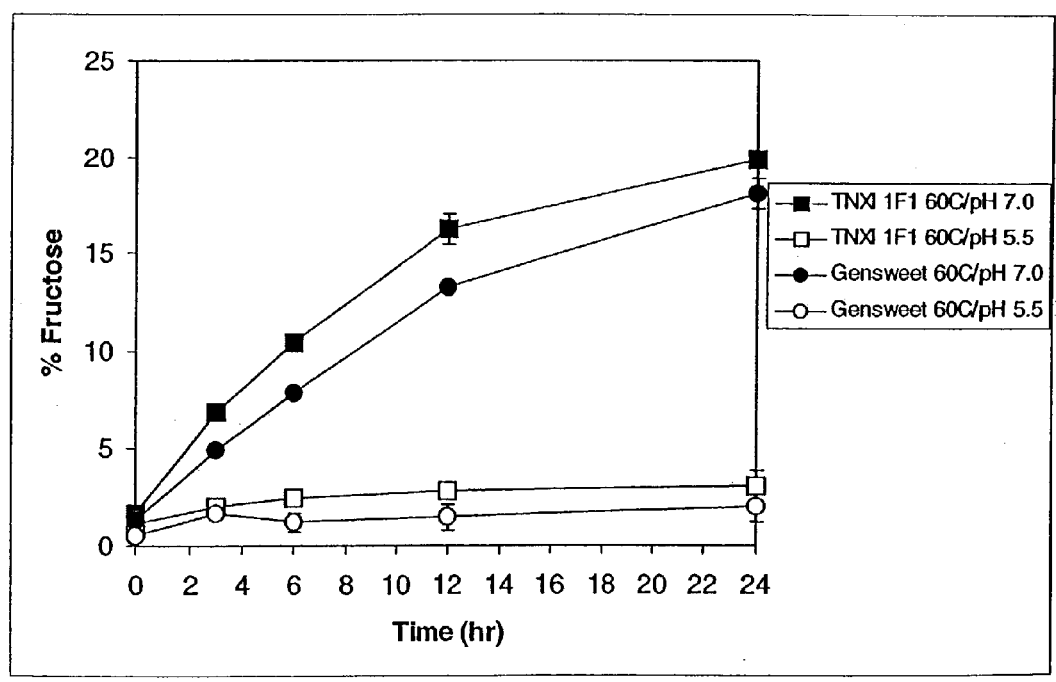
Figure 18:
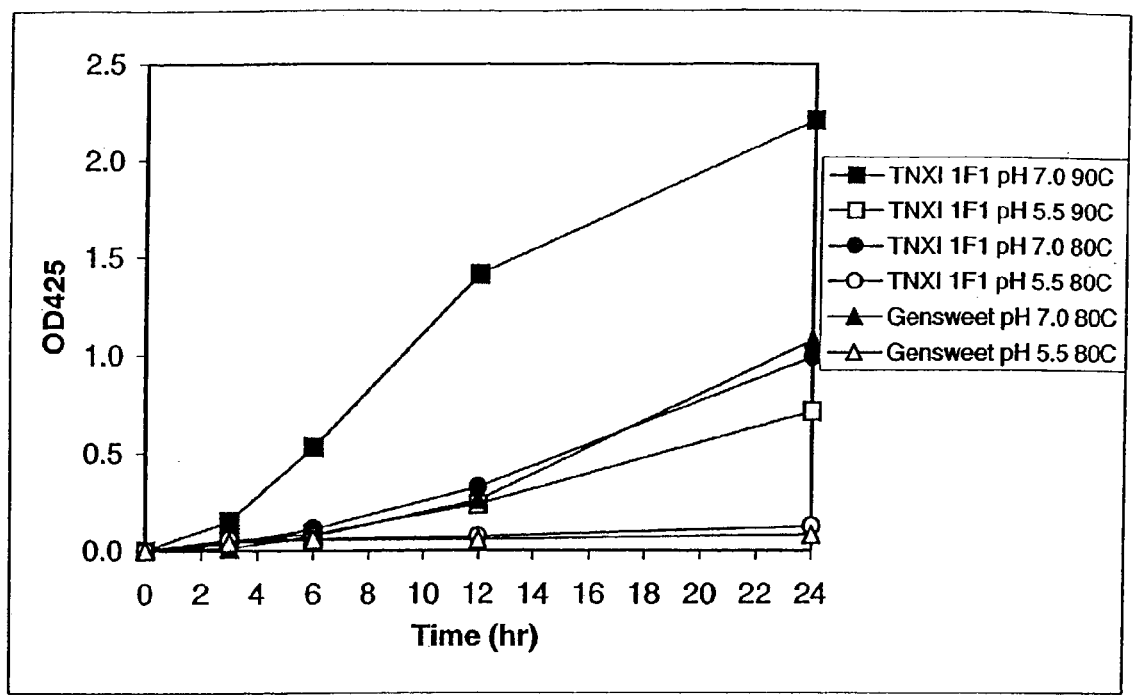
FIG. 18 shows brownness of syrups from experimental fructose conversion of TNXI 1F1 and GENSWEET™.

Fructose production experiments: Fructose production by TNXI 1 F1 vs. Gensweet™ with 45% glucose syrup at various combinations of temperatures and pHs was performed to study the effect of both temperature and pH on fructose conversion ratio (compared to glucose) and potential browning reactions of each enzyme (FIGS. 6, 7 and Table 3). To prove that higher isomerization yield of fructose may be achieved by increasing the reaction temperature, TNXI 1F1 and Gensweet™ were incubated with glucose syrups (pH 7.0 or 5.5) at 60, 80, and 90° C. for up to 24 hr. At both pHs, increases in fructose conversion was observed to be proportional to higher temperature for up to at least 24 hr in all cases with one exception. The syrup incubated with TNXI 1F1 at 90° C., pH 7.0 showed a higher conversion percentage for up to 6 hr after which the conversion rate remain relatively constant and its fructose conversion percentage was surpassed by that of the syrup incubated with TNXI 1F1 at 80° C., pH 7.0. The explanation for this event might be due to TNXI 1F1 short half-life at high temperature above 85° C. The reactions were performed at two different pHs, 7.0 and 5.5, to also investigate the feasibility of prevention of browning the syrups that occurs at high temperature and pH. The brownness of the resulting syrups was monitored at the maximum wavelength of absorbency, which is 425 nm. As expected, the brownness of the syrups was observed to be most pronounced at the highest temperature tested (90° C.) and pH (7.0). Syrups resulting from reactions at low pH (5.5) have dramatically fewer problems with browning.

Fructose conversion percentage was compared between TNXI 1F1 and Gensweet™. At 80° C., TNXI 1F1 compared favorably with Gensweet with slightly higher conversion percentage at 24 hr (32% for TNXI 1F1 vs 28% for Gensweet), which is possibly due to Gensweet's less stable nature at high temperature. However, at 60° C., TNXI 1F1 is better than Gensweet at converting glucose to fructose with higher conversion rate throughout the time course of 24 hrs.

Discussion

The initial goal of this study was to compare biochemical and kinetic parameters as well as productivities of a laboratory-evolved TNXI 1F1 and a commercially available glucose isomerase, Gensweet™ to validate whether the TNXI 1F1 can be genuinely considered for industrial glucose isomerization. Table 2 summarizes key properties of the two enzymes. Not surprisingly, TNXI 1F1 compares favorably with Gensweet™ in every aspect. The key factor that distinguishes the two enzymes was shown to be their thermal stability difference. Although TNXI 1F1 and Gensweet™ have almost the same apparent temperature optima (e.g., 90° C. and 85° C., respectively), Gensweet™ is much less thermostable than TNXI 1F1 by more than one order of magnitude at 60° C. at pH 7.0 or 5.5.

A mathematical model derived to account for the effect of temperature on reversible enzyme kinetics, inactivation rates, and the glucose-fructose chemical equilibrium (Bandlish et al., 2002) was used to estimate their lifetime fructose productivity. Because $K_M$, $k_{cat}$, and $k_D$ are based on soluble enzyme data, the effect of immobilization is not taken into account. However, these estimates provide useful information concerning the potential of the enzyme for HFCS production under optimal conditions. TNXI 1F1 has the lifetime fructose productivity at 60° C., pH 7.0 of 30.5 kg fructose/g enzyme whereas Gensweet™, which reached its maximum fructose conversion in less than a day, produced only 1.3 kg fructose/g enzyme. TNXI 1F1's estimated greater fructose productivity mainly resulted from both greater thermal stability and better kinetics compared to those of Gensweet.

Experimental fructose conversion was performed with 45% glucose syrups incubated with 50 µg of either TNXI 1F1 or Gensweet™ in various conditions to simulate industrial conditions and also to study the effect of temperature and pH on browning reactions resulting from interactions of enzymes with reducing sugars. TNXI 1F1 has a slight edge in term of fructose conversion ratio in every condition tested compared to Gensweet™ with maximal conversion observed at 80° C., pH 7.0. The browness of resulting syrups was monitored up to 24 hr at maximal absorbance of 425 nm. Browning of syrup occurs much more pronounced at 90C, pH 7.0 and can be greatly reduced by lowering the pH, lowering reaction temperature or both. It should also be note that at 60° C., browness of resulting syrup is marginal. When the enzyme concentration in the experiment was increased from 50 g to 100 g and 1 mg, not only did we see more pronounced browning, but precipitates were also observed in the resulting syrups (data not shown).

A study of a glucose isomerase from *Streptomyce rubiginosus* by Visuri et al. (1999) suggested that in an industrial process, glucose isomerase inactivation is caused mainly by a Maillard type browning reaction between the enzyme and the reactive substrates glucose and fructose resulting in inactive glycated protein complexes. It has been found that the reaction temperature can be from about 60 to about 90° C., the reaction pH can be in the range of from about 5.2 to about 8.2, and the preparation can contain from about 35 to 99% w/w dry substance glucose.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule with a nucleotide sequence encoding a polypeptide with glucose isomerase activity comprising the amino acid sequence of SEQ ID NO:2 with two or more amino acid residue changes selected from the group consisting of V186T, L283P, and F187S.

2. The nucleic acid molecule of claim 1 wherein the nucleic acid molecule encodes a polypeptide comprising the amino acid sequence of SEQ ID NO:11.

3. The nucleic acid molecule of claim 1, wherein the nucleic acid molecule encodes a polypeptide comprising the amino acid sequence of amino acids 2–444 of SEQ ID NO:4.

4. The nucleic acid molecule of claim 1, wherein the nucleic acid molecule comprises the nucleic acid sequence of nucleotides 616–1950 of SEQ ID NO:3 or SEQ ID NO:12.

5. A vector comprising the nucleic acid molecule of claim 1.

6. A vector according to claim 5 wherein the vector is selected from the group consisting of a plasmid, virus, and bacteriophage.

7. A vector according to claim 6, wherein the isolated nucleic acid molecule is inserted into the vector in proper orientation and correct reading frame and wherein the isolated nucleic acid molecule is operatively linked to a promoter sequence such that a cell transformed with the vector expresses a polypeptide with glucose isomerase activity comprising the amino acid sequence of SEQ ID NO:11 or amino acids 2–444 of SEQ ID NO:4.

8. An isolated host cell transformed with the vector of claim 7.

9. A process for producing the polypeptide comprising the amino acid sequence of SEQ ID NO:11 or amino acids 2–444 of SEQ ID NO:4 having glucose isomerase activity comprising:
(a) providing the host cell of claim 8;
(b) culturing the host cell to express the polypeptide, and
(c) recovering the polypeptide from the host cell culture.

10. The vector of claim 7, wherein the promoter is selected from the group consisting of the tac promoter, the cell wall protein (CWP) promoter, the phosphoglycerate kinase gene promoter, the alcohol dehydrogenase gene promoter, the glyceraldehyde phosphate dehydrogenase promoter, the glycerol kinase P1 gene promoter, the erythromycin resistance gene EP1 promoter and the phage T7 promoter.

11. The recombinant host cell of claim 8 wherein the host cell is a bacterial cell.

12. The host cell according to claim 8, wherein said cell is selected from the group consisting of Bacillus, Esoherichia, Saccharomyces, and Streptomyces.

13. The host cell according to claim 8, wherein said cell is a fungal cell selected from the group consisting of a yeast cell and a filamentous fungal cell.

14. The host cell according to claim 8, wherein said cell is selected from the group consisting of Aspergillus, Fusarium, and Trichoderma.

15. An isolated nucleic acid molecule comprising a nucleotide sequence encoding a polypeptide comprising the amino acid sequence of SEQ ID NO:2 with two or more amino acid residue changes selected from the group consisting of V186T, L283P, and F187S, and further comprising amino acid substitutions at one or more non-essential amino acid residues such that the polypeptide comprises an amino acid sequence that is at least 98% identical to the amino acid sequence SEQ ID NO:2, that has glucose isomerase activity at temperatures between 60° C. and 80° C. under acidic conditions at pH 6 or less, and that has a half life of about 6.4 hours at 80° C. (pH 7.0).

16. An isolated nucleic acid molecule, which comprises a nucleotide sequence coding for a fusion protein comprising a first polypeptide with glucose isomerase activity having the amino acid sequence of SEQ ID NO:2 with two or more amino acid residue changes selected from the group consisting of V186T, L283P and F187S, operably linked to a second polypeptide.

* * * * *

UNITED STATES PATENT AND TRADEMARK OFFICE
CERTIFICATE OF CORRECTION

PATENT NO. : 7,198,933 B2
APPLICATION NO. : 10/348552
DATED : April 3, 2007
INVENTOR(S) : J. Gregory Zeikus, Dinlaka Sriprapundh and Claire Vieille It is certified that error appears in the above-identified patent and that said Letters Patent is hereby corrected as shown below:

Column 33, line 33, "$CO^2+$" should be --$CO^{2+}$--.

Column 38, line 24, "for 45 see, 50°" should be --for 45 sec, 50°--.

Column 46, line 8, "(Vicille et al., 1995)" should be --(Vieille et al., 1995) --.

Column 80, line 27, "Bacillus, Esoheri-" should be --Bacillus, Escheri--.

Signed and Sealed this

Twenty-eighth Day of August, 2007

JON W. DUDAS
*Director of the United States Patent and Trademark Office*